US009994640B2

(12) United States Patent
Zhang et al.

(10) Patent No.: US 9,994,640 B2
(45) Date of Patent: *Jun. 12, 2018

(54) ANTI-CD40 ANTIBODIES

(71) Applicant: Apexigen, Inc., San Carlos, CA (US)

(72) Inventors: Yongke Zhang, Palo Alto, CA (US); Guo-Liang Yu, Hillsborough, CA (US); Weimin Zhu, San Francisco, CA (US)

(73) Assignee: Apexigen, Inc., San Carlos, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/594,367

(22) Filed: May 12, 2017

(65) Prior Publication Data

US 2017/0246297 A1  Aug. 31, 2017

Related U.S. Application Data

(62) Division of application No. 14/067,770, filed on Oct. 30, 2013, now Pat. No. 9,676,861.

(60) Provisional application No. 61/720,289, filed on Oct. 30, 2012.

(51) Int. Cl.
   *C07K 16/28* (2006.01)
   *A61K 39/395* (2006.01)
   *A61K 39/00* (2006.01)

(52) U.S. Cl.
   CPC .... *C07K 16/2878* (2013.01); *A61K 2039/505* (2013.01); *A61K 2039/545* (2013.01); *C07K 2317/24* (2013.01); *C07K 2317/34* (2013.01); *C07K 2317/73* (2013.01); *C07K 2317/732* (2013.01); *C07K 2317/75* (2013.01)

(58) Field of Classification Search
   None
   See application file for complete search history.

(56) References Cited

U.S. PATENT DOCUMENTS

| | | | |
|---|---|---|---|
| 5,182,368 A | 1/1993 | Ledbetter et al. | |
| 5,674,492 A | 10/1997 | Armitage et al. | |
| 5,675,063 A | 10/1997 | Knight | |
| 5,786,456 A | 7/1998 | Ledbetter et al. | |
| 5,801,227 A | 9/1998 | Fanslow, III et al. | |
| 6,051,228 A | 4/2000 | Aruffo et al. | |
| 6,056,959 A | 5/2000 | de Boer et al. | |
| 6,312,693 B1 | 11/2001 | Aruffo et al. | |
| 6,413,514 B1 | 7/2002 | Aruffo et al. | |
| 6,680,176 B2 | 1/2004 | Matzinger et al. | |
| 6,838,261 B1 | 1/2005 | Siegall et al. | |
| 6,843,989 B1 | 1/2005 | Siegall et al. | |
| 6,946,129 B1 | 9/2005 | Siegall et al. | |
| 7,063,845 B2 | 6/2006 | Mikayama et al. | |
| 7,172,759 B2 | 2/2007 | Thomas et al. | |
| 7,193,064 B2 | 3/2007 | Mikayama et al. | |
| 7,288,251 B2 | 10/2007 | Bedian et al. | |
| 7,338,660 B2 | 3/2008 | Bedian et al. | |
| 7,429,487 B2 | 9/2008 | Pytela et al. |
| 7,462,697 B2 | 12/2008 | Couto et al. |
| 7,498,032 B2 | 3/2009 | Siegall et al. |
| 7,537,763 B2 | 5/2009 | Mikayama et al. |
| 7,547,438 B2 | 6/2009 | Thomas et al. |
| 7,563,442 B2 | 7/2009 | Bedian et al. |
| 7,563,876 B2 | 7/2009 | Deo et al. |
| 7,618,633 B2 | 11/2009 | Bedian et al. |
| 7,626,012 B2 | 12/2009 | Bedian et al. |
| 7,666,422 B2 | 2/2010 | Siegall et al. |
| 7,820,807 B2 | 10/2010 | Thomas et al. |
| 7,824,683 B2 | 11/2010 | Siegall et al. |
| 8,303,955 B2 | 11/2012 | Presta et al. |
| 8,333,970 B2 | 12/2012 | Aukerman et al. |
| 8,337,851 B2 | 12/2012 | Aukerman et al. |
| 8,778,345 B2 | 7/2014 | Zhang et al. |
| 8,957,193 B2 | 2/2015 | Zhang et al. |
| 9,266,956 B2 | 2/2016 | Zhang et al. |
| 9,556,278 B2 | 1/2017 | Zhang et al. |
| 9,676,861 B2 | 6/2017 | Zhang et al. |
| 2003/0211100 A1 | 11/2003 | Bedian et al. |
| 2004/0110226 A1 | 6/2004 | Lazar et al. |
| 2008/0199471 A1 | 8/2008 | Bernett et al. |
| 2009/0104187 A1 | 4/2009 | Kovacevich et al. |
| 2009/0117111 A1 | 5/2009 | Aukerman et al. |
| 2009/0136485 A1 | 5/2009 | Chu et al. |
| 2009/0202531 A1 | 8/2009 | Aukerman et al. |
| 2009/0238825 A1 | 9/2009 | Kovacevich et al. |
| 2009/0297436 A1 | 12/2009 | Garcia-Martinez et al. |
| 2010/0135994 A1 | 6/2010 | Banchereau et al. |
| 2010/0234578 A1 | 9/2010 | Mikayama et al. |
| 2010/0239575 A1 | 9/2010 | Banchereau et al. |

(Continued)

FOREIGN PATENT DOCUMENTS

CN  1582165 A  2/2005
EP  0812206 B1  7/2002
(Continued)

OTHER PUBLICATIONS

Zhang Declaration under 37 CFR 1.132, filed Feb. 12, 2016 in priority U.S. Appl. No. 14/067,770.*
[Author Unknown] "Antibody therapy, Basic to clinical, Immunostimulation effect using an anti-CD40 antibody", Latest Medicine, Japan (2003). (With English Summary).
Cella et al., "Ligation of CD40 on Dendritic Cells Triggers Production of High Levels of Interleukin-12 and Enhances T Cell Stimulatory Capacity: T-T help via APC Activation," J. Exp. Med. ,184:747-752 (1996).
Chen et al., "Enhancement and destruction of antibody function by somatic mutation: unequal occurrence is controlled by V gene combinatorial associations", EMBO Journal, 14(12): 2784-2794 (1995).
Colman, P.M., "Effects of amino acid sequence changes on antibody-antigen interactions", Research in Immunology, 145(1): 33-36 (1994).
Dadgostar et al., "Cooperation of multiple signaling pathways in CD40-regulated gene expression in B lymphocytes," Proc Natl Acad Sci U S A, 99(3):1497-1502 (2002).
Declaration of Yongke Zhang, Ph.D. Under 37 C.F.R. § 1.132, executed on Jul. 1, 2013, filed with the USPTO on Sep. 9, 2013 with U.S. Appl. No. 13/458,730, 2 pages.

(Continued)

*Primary Examiner* — Phillip Gambel
(74) *Attorney, Agent, or Firm* — Cooley LLP

(57) ABSTRACT

The present invention provides high affinity anti-CD40 monoclonal antibodies and related compositions, which may be used in any of a variety of therapeutic methods for the treatment of cancer and other diseases.

9 Claims, 30 Drawing Sheets

(56) References Cited

U.S. PATENT DOCUMENTS

| | | |
|---|---|---|
| 2011/0027276 A1 | 2/2011 | Bernett et al. |
| 2011/0243932 A1 | 10/2011 | Barrett et al. |
| 2011/0293612 A1 | 12/2011 | Perrin et al. |
| 2011/0311525 A1 | 12/2011 | Herbert-Fransen et al. |
| 2012/0087927 A1 | 4/2012 | Matsushima et al. |
| 2012/0121585 A1 | 5/2012 | Heusser et al. |
| 2012/0123695 A1 | 5/2012 | Dornan et al. |
| 2012/0148578 A1 | 6/2012 | Chu et al. |
| 2012/0225014 A1 | 9/2012 | Bedian et al. |
| 2012/0225114 A1 | 9/2012 | Francois et al. |
| 2012/0263732 A1 | 10/2012 | Gladue et al. |
| 2014/0120103 A1 | 5/2014 | Zhang et al. |
| 2016/0208007 A1 | 7/2016 | Zhang et al. |
| 2017/0233483 A1 | 8/2017 | Zhang et al. |

FOREIGN PATENT DOCUMENTS

| | | |
|---|---|---|
| JP | 2006-342173 A | 12/2006 |
| WO | WO 1995/017202 A2 | 6/1995 |
| WO | WO 1996/018413 A1 | 6/1996 |
| WO | WO 1996/026735 A1 | 9/1996 |
| WO | WO 1999/042075 A2 | 8/1999 |
| WO | WO 2003/040170 A2 | 5/2003 |
| WO | WO 2003/084999 A1 | 10/2003 |
| WO | WO 2002/011763 A1 | 2/2004 |
| WO | WO 2005/063981 A1 | 7/2005 |
| WO | WO 2006/128103 A2 | 11/2006 |
| WO | WO 2007/075326 A2 | 7/2007 |
| WO | WO 2010/123012 A1 | 10/2010 |
| WO | WO 2011/120134 A1 | 10/2011 |
| WO | WO 2012/019041 A2 | 2/2012 |
| WO | WO 2012/087928 A2 | 6/2012 |
| WO | WO 2012/145673 A1 | 10/2012 |
| WO | WO 2012/149356 A2 | 11/2012 |
| WO | WO 2014/070934 A2 | 5/2014 |

OTHER PUBLICATIONS

Eliopoulos et al., "CD40 Induces Apoptosis in Carcinoma Cells through Activation of Cytotoxic Ligands of the Tumor Necrosis Factor Superfamily," Mol Cell Biol, 20(15): 5503-15 (2000).

Eliopoulos et al., "CD40-induced growth inhibition in epithelial cells is mimicked by Epstein-Barr Virus-encoded LMP1: involvement of TRAF3 as a common mediator," Oncogene,13(10):2243-54 (1996).

European Application No. 12777376.0, Extended European Search Report dated Sep. 17, 2014.

Francisco et al., "Agonistic Properties and in Vivo Antitumor Activity of the Anti-CD40 Antibody SGN-14," Cancer Res, 60: 3225-31 (2000).

French et al.. "CD40 antibody evokes a cytotoxic T-cell response that eradicates lymphoma and bypasses T-cell help," Nat Med., 5(5):548-553 (1999).

Funakoshi et al., "Inhibition of human B-cell lymphoma growth by CD40 simulation," Blood, 83(10):2787-94 (1994).

Gladue et al., "The CD40 agonist antibody CP-870,893 enhances dendritic cell and B-cell activity and promotes anti-tumor efficacy in SCID-hu mice." Cancer Immunology Immunotherapy (2011); 60(7): 1009-1017.

Gladue et al., "In vivo efficacy of the CD40 against antibody CP-870,893 against a broad range of tumor types: Impact of tumor CD40 expression, dendritic cells, and chemotherapy," J Clin Oncol,24 (18S):103s (2006).

Grewal I. S. and Flavell R. A., "CD40 and CD154 in Cell-Mediated Immunity," Annu Rev Immunol, 16:111-35 (1998).

Hess S and Engelmann H., "A Novel Function of CD40: Induction of Cell Death in Transformed Cells," J Exp Med,183(1):159-67 (1996).

Horton et al., "Fc-engineered anti-CD40 antibody enhances multiple effector functions and exhibits potent in vitro and in vivo antitumor activity against hematologic malignancies", Blood, 116(16): 3004-3012 (2010).

Hussein, et al., "A phase I multidose study of dacetuzumab (SGN-40; humanized anti-CD40 monoclonal antibody) in patients with multiple myeloma," Haematologica, 95(5): 845-848 (2010).

International Preliminary Report on Patentability for International Application No. PCT/US2012/035502 dated Oct. 29, 2013.

International Preliminary Report on Patentability for International Application No. PCT/US2013/067583 dated May 5, 2015.

International Search Report and Written Opinion for International Application No. PCT/US2012/035502 dated Nov. 7, 2012.

International Search Report and Written Opinion for International Application No. PCT/US2013/067583 dated Feb. 25, 2014.

Johnson, et al., "A Cancer Research UK phase I study evaluating safety, tolerability, and biological effects of chimeric anti-CD40 monoclonal antibody (MAb), Chi Lob 7/4," J. Clinc. Oncol. 28(15s): 1-2 (2010).

Kehry, "CD40-Mediated Signaling in B Cells Balancing Cell Survival, Growth, and Death," J Immunol, 156:2345-2348 (1996).

Khalil M. and Vonderheide R. H., "Anti-CD40 agonist antibodies: Preclinical and clinical experience," Update Cancer The, 2(2): 61-65 (2007).

Khubchandani, et al., "Dacetuzumab, a humanized mAb against CD40 for the treatment of hematological malignancies," Current Opinion in Investigational Drugs, 10(6): 579-587 (2009).

Kussie et al., "A single engineered amino acid substitution changes antibody fine specificity", The Journal of Immunology, 152(1): 146-152 (1994).

Law et al, "Preclinical Antilymphoma Activity of a Humanized Anti-CD40 Monoclonal Antibody, SGN-40," Cancer Res, 65:8331-8338 (2005).

Li et al., "Inhibitory FcY Receptor Engagement Drives Adjuvant and Anti-Tumor Activities of Agonistic CD40 Antibodies," Science, 333(6045): 1030-1034 (2011).

Long et al., "Antagonist Anti-CD40 Monoclonal Antibody, CHIR-12.12, Inhibits Growth of a Rituximab Resistant NHL Xenograft Model and Achieves Synergistic Activity When Combined with Ineffective Rituximab," IMF Oral Presentation and Abstract No. 3, Blood, 104(11, Part 1): Abst 3281 (2004).

Luqman et al, "The antileukemia activity of a human anti-CD40 antagonist antibody HCD122, on human chronic lymphocytic leukemia cells," Blood, 112:711-720 (2008).

Madhok et al., "Serum interleukin 6 levels in rheumatoid arthritis: correlations with clinical and laboratory indices of disease activity," Annals of the Rheumatic Disease, 52:232-234 (1993).

Malmborg, et al., "Affinity and epitope profiling of mouse anti-CD40 monoclonal antibodies," Scandinavian Journal of Immunology, 57(6): 517-524 (2003).

Moore et al., "Engineered Fc variant antibodies with enhanced ability to recruit complement and mediate effector functions," Landes Biosciences, mAbs 2(2): 181-189, Mar./Apr. 2010.

New Zealand Application No. 616923, First Examination Report dated Aug. 25, 2014.

O'Grady et al., "CD40 Expression in Hodgkin's Disease," Am J Pathol, 144(i): 21-26 (1994).

O'Sullivan B. and Ranjeny T, "CD40 and Dendritic Cell Function," Critical Reviews in Immunology, 23(1&2): 83-107 (2003).

Offlazoglu et al, "Macrophages and Fc-receptor interactions contribute to the antitumour activities of the anti-CD40 antibody SGN-40," Br J Cancer, 100(1):113-7 (2009).

Ohno et al., "Antigen-binding specificities of antibodies are primarily determined by seven residues of VH." Proceedings of the National Academy of Sciences (1985); 82(9): 2945-2949.

Pellat-Deceunynck et al., "Expression of CD28 and CD40 in human myeloma cells: a comparative study with normal plasma cells," Blood, 84: 2597-2603 (1994).

Pype et al., "TTRAP, a Novel Protein That Associates with CD40, Tumor Necrosis Factor (TNF) Receptor-75 and TNF Receptor-asociated Factors (TRAFs), and That Inhibits Nuclear Factor-kB Activation," J Biol Chem., 275(24):18586-93 (2000).

Rudikoff et al., "Single amino acid substitution altering antigen-binding specificity", Proc Natl Acad Sci USA, 79: 1979-1983 (1982).

(56) References Cited

OTHER PUBLICATIONS

Sakata, et al., "Differential regulation of CD40-mediated human B cell responses by antibodies directed against different CD40 epitopes," Cell Immunology, 201 (2): 109-123 (2000).

Stout, "The many roles of CD40 in cell-mediated inflammatory responses," Immunol. Today,17(10):487-492 (1996).

Tai et al., "Human Anti-CD40 Antagonist Antibody Triggers Significant Antitumor Activity against Human Multiple Myeloma," Cancer Res, 65(8):5898-5906 (2005).

Tai et al.; "Mechanisms by which SGN-40, a Humanized Anti-CD40 Antibody, Induces Cytotoxicity in Human Multiple Myeloma Cells: Clinical Implications," Cancer Res., 64(13):2846-2852 (2004).

Tong A. W. and Stone M. J., "Prospects for CD40-directed experimental theraphy of human cancer," Cancer Gene Ther., 10(1):1-13 (2003).

Tong et al., "Growth-inhibitory Effects of CD40 Ligand (CD154) and Its Endogenous Expression in Human Breast Cancer," Clin Cancer Res, 7(3):691-703 (2001).

Uckun et al., "Temporal association of CD40 antigen expression with discrete stages of human B-cell ontogeny and the efficacy of anti-CD40 immunotoxins against clonogenic B-lineage acute lymphoblastic leukemia as well as B-lineage non-hodgkins lymphoma cells," Blood, 76:2449-2456 (1990).

Van Kooten C and Banchereau J., "CD40-CD40 ligand," J Leukoc Biol, 67(1):2-17 (2000).

Van Mierlo et al., "CD40 stimulation leads to effective theraphy of CD40-tumors through induction of strong systemic cytotoxic T lymphocyte immunity," Proc Natl Acad Sci U S A., 99(8): 5561-5566 (2002).

Van Snick, "Interleukin-6: an overview," Annu. Rev. Immunol., 8:253-278 (1990).

Von Leoprechting et al., "Stimulation of CD40 on Immunogenic Human Malignant Melanomas Augments Their Cytotoxic T Lymphocyte-mediated Lysis and Induces Apoptosis," Cancer Res, 59(6):1287-94 (1999).

Vonderheide, et al., "Clinical Activity and Immune Modulation in Cancer Patients Treated With CP-870,893, a Novel CD40 Agonist Monoclonal Antibody," Journal of Clinical Oncology, 25(7): 876-883 (2007).

White et al., "Interaction with FcγRIIB Is Critical for the Agonistic Activity of Anti-CD40 Monoclonal Antibody," Journal of Immunology, 187(4): 1754-1763 (2011).

Yamasaki et al., "Cloning and Expression of the Human Interleukin-6 (BSF-2/IFN beta 2) Receptor," Science, 241:825-828 (1988).

Young et al, "CD40 and epithelial cells: across the great divide," Immunol Today, 19:502-6 (1998).

Zhang et al., "Poster Presentations—Monoclonal Antibodies 1, Abstract 2451: A novel humanized anti-CD40 RabMAb exhibits potent efficacy in preclinical models", Cancer Research 70 (8 Suppl): Abstract No. 2451 (2010).

Ziebold et al.; "Differential Effects of CD40 Stimulation on Normal and Neoplastic Cell Growth," Archivum Immunol Ther Exp (Warsz), 48: 225-233 (2000).

Hayashi, Toshiaki, et al. "Recombinant humanized anti-CD40 monoclonal antibody triggers autologous antibody-dependent cell-mediated cytotoxicity against multiple myeloma cells." British Journal of Haematology (2003); 121(4): 592-596.

\* cited by examiner

Anti-CD40 rabbit monoclonal antibody heavy chain

```
                                                                ==CDR1====

R-2  METGLRWLLLVAVLKGVQC-QQQLEESGGGLVKPEGSLTLTCKANGFSFSAN-YYMC

R-3  METGLRWLLLVAVLKGVQC--QSLEESGGDLVKPGASLTLTCTASGFSFSDS-FWIA

R-5  METGLRWLLLVAVLKGVQC-QEQLEESGGDLVKPGASLTLTCKASGFDLSST-YYMC

R-6  METGLRWLLLVAVLKGVQC-QEQLVESGGGLVQPGGSLTLTGTASGFSFSSS-YSMC

R-7  METGLRWLLLVAVLKGVQC-QEQLEESGGDLVKPEGSLTLTCTASGFSFGSG-YYMC

R-8  METGLRGLLLVAVLKGVQC---QSLEESGGDLVKPGASLTLTCTASGFSFSS--TYVC

R-9  METGLRWLLLVAVLKGVQC---QSLEESGGDLVKPGASLTLTCTASRFSFSS--TYMC

R-10 METGLRWLLLVAVLKGVQC-QEQLVESGGGLVKPGASLAVTCKASGFSFSRG-YYMC

R-12 METGLRWLLLVAVLKGVQC--QSLEESGGDLVKPGASLTLTCTASGFSFSDS-FWIA

R-16 METGLRWLLLVAVLKGVQC--QSLEESGGGLVKPGGTLTLTCKASGFSLNY--YWPC

R-18 METGLRWLLLVAVLKGVQC---QSLEESGGDLVKPGASLTLTCTASGIDFSSY-YYMC

R-20 METGLRWLLLVAVLKGVQC-QEQLEESGGDLVKPEGSLTLTCTASGFSFGSG-YYMC

R-24 METGLRWLLLVAVLKGVQC---QSLEESGGDLVKPGASLTLTCTASGFSFSRG-YYIC

R-26 METGLRWLLLVAVLKGVQC-QEQLVESGGDLVQPEGSLTLTSTASGFSLSSS-YFMC

R-30 METGLRWLLLVAVLKGVQC--QSLEESGGDLVKPGASLTLTCTASGFSFSDS-FWIA

R-33 METGLRWLLLVAVLKGVQC--QSLEESGGDLVKPGASLTLTCTASGFSFSSS-YWIC
```

FIG. 16A

Anti-CD40 rabbit monoclonal antibody heavy chain

========CDR2======

R-2  WVRQAPGKGLELIA<u>CIYA--SSGSTWYASWAKG</u>RFTISKSTSLNTVTLQMTSLTVAD

R-3  WVRQAPGKGLEWIG<u>CIHAL-SSGSTYYANWARG</u>RFTISKTSST-TVTLQMNSLTAAD

R-5  WVRQAPGKGLEWIG<u>CIY---ATGGTYYASWAKG</u>RFTISKTSPT-TVTLQMPSLTAAD

R-6  WVRQAPGKGLEWIG<u>CIDT--GRGYTYHASGAKG</u>RFTFSKTSST-TVTLQMTSLTAAD

R-7  WVRQAPGKGLEWIG<u>CIYV--GHDSLYYAGWARG</u>RFTISKTSST-TVTLQMTSLTAAD

R-8  WVRQAPGKGLEWIA<u>CIYT--GDGTNYSASWAKG</u>RFTISKPSST-TVTLQMTSLTPAD

R-9  WVRQAPGKGLEWIA<u>CTYTG-SSGGTYYASWAKG</u>RFTISQTSST-TVTLQLTGLTPAD

R-10 WVRQAPGKGLEWIA<u>CIGA--GSGNTYYATWTKG</u>RATISKTSWT-TVSLEMTSLTGAD

R-12 WVRQAPGKGLEWIG<u>CIHAL-SSGSTYYANWARG</u>RFTISKTSST-TVTLQMNSLTAAD

R-16 WVRQAPGKGLEWVA<u>CLNGG-DSDTTVYARWAKG</u>RFTISKASST-TVTLQMTSLTAAD

R-18 WVRQAPGKGLEWIG<u>CIYA--GSGSTYYASWAKG</u>RFTISKTSST-TVTLQMTSLTAAD

R-20 WVRQAPGKGLEWIG<u>CIYV--GHDSLYYAGWARG</u>RFTISKTSST-TVTLQMTSLTAAD

R-24 WVRQAPGKGLEWIA<u>CIGA--GSGGTYFASWAKG</u>RFSISRTSST-TVTLQMTSLTAAD

R-26 WVRQAPGKGLEWIA<u>CISAG-SSGHTYYASWAKG</u>RFTVSKTSST-TVTLQMTSLTAAD

R-30 WVRQAPGKGLEWIG<u>CIHAL-SSGSTYYANWARG</u>RFTISKTSST-TVTLQMNSLTAAD

R-33 WVRQAPGKGLEWIA<u>CINTG-SSVTTVYARWAKG</u>RFTISKASST-TVTLQMTSLTAAD

*FIG. 16B*

Anti-CD40 rabbit monoclonal antibody heavy chain

========CDR3========

R-2    TATYFCARSGGYAAY----------DLWGPGTLVTVSS

R-3    TATYFCARSYAGYADYNVATGL---NLWGPGTLVTVSS

R-5    TATYFCARDIVGDNIYYF--------NFWGPGTLVTVSS

R-6    TATYFCARSSYVRYDNRNYGF-----NLWGPGTLVTVSS

R-7    TATYFCARGASITNSYF---------SLWGPGTLVTVSS

R-8    TATYFCARPDITYGFAI---------NFWGPGTLVTVSS

R-9    TATYFCARPDVGFDFAI---------NFWGPGTLVTVSS

R-10   TATYFCAREDPGNDDYGYAD------NLWGPGTLVTVSS

R-12   TATYFCARSYAGYADYNVATGL---NLWGPGTLVTVSS

R-16   TATYFCARYIIPGYHF----------NLWGPGTLVTVSS

R-18   TATYFCARSGYNDGSYY---------NLWGPGTLVTVSS

R-20   TATYFCARGASITNSYF---------SLWGPGTLVTVSS

R-24   TATYFCAREDAGNDDYGYAR------NLWGPGTLVTVSS

R-26   TATYFCARASADVGDY----------SLWGPGTLVTVSS

R-30   TATYFCARSYAGYADYNVATGL---NLWGPGTLVTVSS

R-33   TATYFCARYIIPGYNF----------NLWGPGTLVTVSS

*FIG. 16C*

Anti-CD40 rabbit monoclonal antibody heavy chain

```
                                                              ==CDR1====
R-35   METGLRWLLLVAVLKGVQC--QSLEESGGDLVKPGASLTLTCTASGFSFSGT-YWIC

R-36   METGLRWLLLVAVLKGVQC-QQQLVESGGGLVKPGASLTLTCKASGFSFSST-YWIC 19-21  METGLRWLLLVAVLKGVQC--QSLEESGGRLVTPGTPLTLTCTVSGFDLSS--NAMN 19-35  METGLRWLLLVAVLKGVQC--QSLEESGGRLITPGTPLTLTCTVSGFSLSS--YAVN 19-41  METGLRWLLLVAVLKGVQC--QSLEESGGRLVTPGTPLTLTCTVSGFSLST--YDMT 19-45  METGLRWLLLVAVLKGVQC--QSVEESGGRLVTPGTPLTLNCTVSGFSLSS--YDMN 19-57  METGLRWLLLVAVLKGVQS--QSVEESGGRLITPGTPLTLTCTISGFSLSS--YAVD 19-59  METGLRWLLLVAVLKGVQC--QSVEESGGRLVTPGTPLTLTCTVSGFSLS--DYVMR
```

FIG. 16D

Anti-CD40 rabbit monoclonal antibody heavy chain

========CDR2=====

R-35  WVRQAPGKGLEWIACIYAG-ASGNSYYANWAQGRFIISKRSST-AVTLQMTSLTAAD

R-36  WVRQAPGKGLEWIGCINSD-DSGTNVYANWAKGRFTISKASST-TVTLQMTSLTAAD 19-21 WVRQAPGKGLEWIGYITIS---GSAGYASWAKGRFTISKTSTT--VDLKISSPTTED 19-35 WVRQAPGKGLEYIGLIATG---GGTFYTNWARGRLTISKTSTT--VDLKMPSPQTED 19-41 WVRQAPGKGLEWLGLINTI---GSAYYASWASGRFTISKTSTS--VTLKMTSPTTED 19-45 WVRQAPGKGLEWIGVIWNN---GEIFYASWAKGRFTISKTSTT--VDLKITSPSTED 19-57 WVRQAPGKGLEYIGIIATG---GGTYYTNWAKGRFTISKTSTT--VDLKMTSPQPED 19-59 WVRQAPGKGLEWIGVISSA---GNTYYATWAKDRFTISKTSTT--VDLRIASPTTED

*FIG. 16E*

Anti-CD40 rabbit monoclonal antibody heavy chain

========CDR3========

| | |
|---|---|
| R-35 | TATYFCARSYTGYADYNVATGL---NLWGPGTLVTVSS |
| R-36 | TATYFCARYPIPGYHF--------NLWGPGTLVTVSS |
| 19-21 | TATYFCARGYNTMA-----------IWGPGTLVTVSS |
| 19-35 | TATYFCVRGYPGSSDF--------NIWGPGTLVTVSS |
| 19-41 | TATYFCVRGVPGYSSSF-------NIWGPGTLVTVSS |
| 19-45 | TATYFCAGDADGGVVSYF------HVWGPGTLVTVSS |
| 19-57 | TATYFCVRGYPGSSDF--------NIWGPGTLVTVSS |
| 19-59 | TATYFCARIWRPDDPTNS------DIWGPGTLVTVSS |

*FIG. 16F*

Anti-CD40 rabbit monoclonal antibody light chain

| | |
|---|---|
| R-2 | MDTRAPTQLLGLLLLWLPGATF-AAVLTQTPSPVSAAVGGTVSISC |
| R-3 | MDTRAPTQLLGLLLLWLPGARC-DVVMTQTPSSASAAVGGTVTTKC |
| R-5 | MDTRAPTQLLGLLLLWLPGARC-ALVMTQTPSSVSAAVGGTVTINC |
| R-6 | MDTRAPTQLLGLLLLWLPGARCADIVMTQTPASVEAAVGGTITINC |
| R-7 | MDTRAPTQLLGLLLLWLPGVTF-AIEMTQTPFSVSEPVGGTVTIKC |
| R-8 | MDTRAPTQLLGLLLLWLPGARSADIVMTQTPSSASEPVGGTVTIKC |
| R-9 | MDTRAPTQLLGLLLLWLPGARCADIVMTQTPSSASEPVGGTVTIKC |
| R-10 | MDTRAPTQLLGLLLLWLPGARCADIVMTQTPSSVSAAVGGTVTIKC |
| R-12 | MDTRAPTQLLGLLLLWLPGARC-DVVMTQTPSSASAAVGGTVTIKC |
| R-16 | MDTRAPTQLLGLLLLWLPGARC-AYDMTQTPASVSAAVGDTVTIKC |
| R-18 | MDTRAPPQLLGLLLLWLPGARCADIVMTQTPSSVEAAVGGTVTIKC |
| R-20 | MDTRAPTQLLGLLLLWLPGVTF-AIEMTQTPFSVSEPVGGTVTIKC |
| R-24 | MDTRAPTQLLGLLLLWLPGARCADIVMTQTPASVSAAVGGTVTINC |
| R-26 | MDTRAPTQLLGLLLLWLPGARC-DVMMTQTPASVSAPVGGTVTIKC |
| R-30 | MDTRAPTQLLGLLLLWLPGARC-DVVMTQTPSSASAAVGGTVTIKC |
| R-33 | MDTRAPTQLLGLLLLWLPGARC-AYDMTQTPASVEVAVGGTVTINC |

*FIG. 16G*

Anti-CD40 rabbit monoclonal antibody light chain

```
      ====CDR1========                ==CDR2=

R-2   QSSKSVYNN----NWLSWYQQKPGQPPKLLIYRASTLASGVPSRFRGSGSGTEFTLT

R-3   QASQSIG------SYLAWYQQKPGQRPKLLIYAASNLASGVPSRFKGSRSGTEYTLT

R-5   QASQTIS------NELSWYQQKPGQPPKLLIYLASTLASGVPSRFKGSGSGTQFTLT

R-6   QASESIS------SWLSWYQQKPGQRPKLLIYYTSNLASGVPSRFKGSGAGTDFTLT

R-7   QASEDIF------SNLGWYQQKPGQPPKLLIYAASNLESGVPSRFKGSGSGTDFTLT

R-8   QASQSIS------SRLAWYQQKPGQPPKLLIYRASTLASGVPSRFKGSGSGTEFTLT

R-9   QASQSIS------SRLAWYQQKPGQPPKLLIYRASTLASGVSSRFKGSGSGTQFTLT

R-10  QASETIY------TLLAWYQQKPGQPPKLLIYRASTLESGVPSRFQGSGSGTEFTLT

R-12  QASQSIG------SYLAWYQQKPGQRPKLLIYAASNLASGVPSRFKGSRSGTEYTLT

R-16  QASQSIS------SYLYWYQQKPGQPPKLLIYQASKLASGVPSRFKGSGSGTEYTLT

R-18  QASQSIY------TWLAWYQQKPGQPPKLLIYKASTLASGVPSRFKGSGSGTDYTLT

R-20  QASEDIF------SNLGWYQQKPGQPPKLLIYAASNLESGVPSRFKGSGSGTDFTLT

R-24  QASESAY------TLLAWYQQKPGQPPKLLIYGASILESGVPSRFKGSGSGTDFTLT

R-26  QASQSIS------TYLAWYQQKPGQPPKLLIYYASTLASGVSSRFEGSRSVTEYTLT

R-30  QASQSIG------SYLAWYQQKPGQRPKLLIYAASNLASGVPSRFKGSRSGTEYTLT

R-33  QASQSIS------SYLYWYQQKPGQPPKLLIYDASKLASGVPSRFKGSGSGTQFTLT
```

*FIG. 16H*

Anti-CD40 rabbit monoclonal antibody light chain

=====CDR3=====

```
R-2    ISDVVCDDAATYYCAGYESVNTDG---HAFGGGTEVVVK

R-3    ISGVQREDAATYYCLGSFTGSD-----TTFGGGTELEIL

R-5    ISDLECADAATYYCQQGYTYSSVD---NVFGGGTEVVVK

R-6    ISDLECADAATYYCQSNYGSSSSTY--YGFGGGTEVVVK

R-7    INDLECDDAATYYCQSAYYSSSY----LAFGGGTEVVVK

R-8    ISDLECADAATYYCQCTGYGIS-----WPIGGGTEVVVK

R-9    ISDLECADAATYYCQCTGYTIS-----WPFGGGTEVVVK

R-10   ISDLECADAATYYCQSHYFDSSSGYG-NTFGGGTEVVVK

R-12   ISGVQREDAATYYCLGSFTGSD-----TTFGGGTELEIL

R-16   ISDLECADVATYYCQQGYSHINVD---NIFGGGFQVVVK

R-18   ISDLECDDAATYYCQRYSWNGSYG---VSFGGGTEVVVR

R-20   INDLECDDAATYYCQSAYYSSSY----LAFGGGTEVVVK

R-24   ISDLECADAATYYCQSHYFGSSSGYA-NTFGGGTEVVVK

R-26   ISDLECADAATYYCQSTYYGNG-----HPFGGGTEVVVK

R-30   ISGVQREDAATYYCLGSFTGSD-----TTFGGGTELEIL

R-33   ITGVECADAATYYCQQGYSHINVD---NIFGGGTEVVVK
```

*FIG. 16I*

Anti-CD40 rabbit monoclonal antibody light chain

R-35    MDTRAPTQLLGLLLLWLPGARC-ALVMTQTPSSTSAAVGGTVTIKC

R-36    MDTRAPTQLLGLLLLWLPGARC-AYDMTQTPASVEVAVGGTVTIKC 19-21   MDTRAPTQLLGLLLLWLPGATF-AQVLTQTPSPVSAPVGGTVTINC 19-35                       ALAPGARC-AVVLTQTPASVSAAVGGTVSISC 19-41   MDTRAPTQLLGLLLLWLPGATF-AIVMTQTPSSKSVAVGDTVTINC 19-45   MDTRAPTQLLGLLLLWLPGARC-AYDMTQTPASVEVAVGGTVTIKC 19-57   MDTRAPTQLLGLLLLWLPGARC-AVVLTQTPASVSAAVGGTVSISC 19-59   MDTRAPTQLLGLLLLWLPGARC-DVVMTQTPSSTSAAVGGTVTIKC

FIG. 16J

Anti-CD40 rabbit monoclonal antibody light chain

```
          ====CDR1========          ===CDR2=

R-35      QASQSIG------SYLAWYQQKPGQRPKLLIYAASNLASGDPSRFSASRSGTEY

R-36      QASQNIY------GYLFWYQQKPGQPPNLLIAEASKLPSGVPSRFKGSGSGTEY 19-21     QSSQNVLIN----NRLAWYQQKPGQPPKLLIYDASKLASGVPSRFKGSGSGTQF 19-35     QSSKSVYNK----HHLAWLQQKPGQPPKLLIYYASTLASGVPSRFRGSGSGTQF 19-41     QASESVDSN----KRLAWYQQKPGQPPKLLIYTASTLASGVPSRFKGSGSGTEF 19-45     QASQTIY------TYLAWYLQKPGQPPKLLIYEASKLASGVSSRFEGSGSGTQF 19-57     QSSKSVYNK----NHLAWLQQKPGQPPKLLIYYTSTPASGVPSRFRGSGSGTQL 19-59     QASESIS------SSLAWYQQKPGQPPKLLIYYASDLASGVPSRFSGSRSGTEY
```

FIG. 16K

Anti-CD40 rabbit monoclonal antibody light chain

```
                     =====CDR3=====

R-35    TLTISGVQREDAATYYCLGSFTGSD-----TTFGGGTELEIL

R-36    SLTISGVECADAATYYCQQSYSHINVD---NIFGGGTEVVVK 19-21   TLTISGVQCDDAATYYCQAGYSSGDG----NAFGGGTEVVVK 19-35   TLTISDVQCDDAATYYCAGGYPSDSD----NTFGGGTEVVVE 19-41   TLTISDVVCDDAATYYCAGYKATTTDA---SAFGGGTEVVVK 19-45   TLTISGVQCDDAATYYCQQGYNSRHVD---NVFGGGTEVVVK 19-57   TLTISDVQCDDAATYYCAGGYNSDSD----NTFGGGTEVVVE 19-59   TLTISGVQREDAATYYCLGGYATAAYR---TAFGGGTELEILC
```

FIG. 16L

ANTI-CD40 ANTIBODIES

CROSS REFERENCE TO RELATED APPLICATIONS

This application is a divisional of U.S. patent application Ser. No. 14/067,770, filed on Oct. 30, 2013, which claims the benefit under 35 U.S.C. § 119(e) of U.S. Provisional Application No. 61/720,289 filed, on Oct. 30, 2012, where these applications are herein incorporated by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is APEX_016_02US_ST25.txt. The text file is 93 KB, was created on May 12, 2017 and is being submitted electronically via EFS-Web.

BACKGROUND

Technical Field

The present invention relates generally to anti-CD40 antibodies, compositions and methods of using same. Such antibodies are useful, for example, in methods for treating a variety of oncological diseases.

Description of the Related Art

The majority of leukemias and lymphomas originate from malignant transformation of B-lineage cells. The expression of cell surface B-lineage-restricted antigens such as CD20 makes it an attractive target for antibody therapy. Antibody therapeutics have dramatically changed the management of patients with non-Hodgkin lymphoma (NHL) and chronic lymphocytic leukemia (CLL). Since the approval of rituximab, the antibody alone or in combination with chemotherapy has remarkably improved response rates, long-term outcomes, and quality of life (Chinn P, Braslawsky G, White C, et al. Antibody therapy of non-Hodgkin's B-cell lymphoma. Cancer Immunol Immunother 2003; 52:257-280; Rastetter W, Molina A, White C A. Rituximab: Expanding role in therapy for lymphomas and autoimmune diseases. Annu Rev Med 2004; 55:477-503). However, a substantial number of patients exhibit either primary or acquired resistance to rituximab, suggesting that current approaches targeting CD20 have limitations in clinical outcomes, and there is a need for improvement by developing novel immunotherapeutics for B cell lymphoma and leukemia with distinct mechanisms of action (Stolz C, Schuler M. Molecular mechanisms of resistance to Rituximab and pharmacologic strategies for its circumvention. Leukemia and lymphoma. 2009; 50(6):873-885; Bello C, Sotomayor E M. Monoclonal antibodies for B-cell lymphomas: Rituximab and beyond. Hematology Am Soc Hematol Educ Program 2007; 233-242; Dupire S, Coiffier B. Targeted treatment and new agents in diffuse large B cell lymphoma. Int J Hematol 2010; Jun. 18 (online)), such as the anti-CD40 mAb, APX005.

The Role of CD40 in the Regulation of Immune Responses

Full activation of T cells requires two distinct but synergistic signals. The first signal, delivered through the T-cell antigen receptor, is provided by antigen and MHC complex on APCs and is responsible for the specificity of the immune response. The secondary, or costimulatory, signal is through the interaction of CD28 with B7-1 (CD80)/B7-2 (CD86), and CD40 with CD40L, which are required to mount a full scale T cell response. In the absence of costimulatory signals, T cells may undergo unresponsiveness (anergy) or programmed cell death (apoptosis) upon antigen stimulation.

CD40, a member of the TNF receptor (TNFR) superfamily, is expressed primarily on B cells and other antigen-presenting cells (APCs) such as dendritic cells and macrophages. CD40 ligand (CD40L) is expressed primarily by activated T cells.

CD40 and CD40L interaction serves as a costimulatory signal for T cell activation. CD40-CD40L engagement on resting B cells induces proliferation, immunoglobulin class switching, antibody secretion, and also has a role in the development of germinal centers and the survival of memory B cells, all of which are essential to humoral immune responses (Kehry M R. J Immunol 1996; 156: 2345-2348). Binding of CD40L to CD40 on dendritic cells induces DC maturation as manifested by increasing expression of co-stimulatory molecules such as B7 family (CD80, CD86) and production of proinflammatory cytokines such as interleukin 12. These lead to potent T cell responses (Stout, R. D., J. Suttles. 1996. Immunol. Today 17:487-492; Brendan O'Sullivan, Ranjeny Thomas. Critical Reviews in Immunology 2003; 23: 83-107; Cella, M., D. Scheidegger, K. Palmer-Lehmann, P. Lane, A. Lanzavecchia, G. Alber. J. Exp. Med. 1996; 184:747-452).

CD40 signal transduction activates multiple pathways including NF-KappaB (Nuclear Factor-KappaB), MAPK (Mitogen-Activated Protein Kinase) and STAT3 (Signal Transducers and Activators of Transcription-3) (Pype S, et al. J Biol Chem. 2000 Jun. 16; 275(24):18586-93) that regulate gene expression through activation of Activating Proteins, c-Jun, ATF2 (Activating Transcription Factor-2) and Rel transcription factors (Dadgostar H, et al. Proc Natl Acad Sci USA. 2002 Feb. 5; 99(3):1497-502). The TNFR-receptor associated factor adaptor proteins (e.g., TRAF1, TRAF2, TRAF3, TRAF5, and TRAF6) interact with this receptor and serve as mediators of the signal transduction. Depending on the particular cell type, CD40 engagement results in a particular gene expression pattern. Genes activated in response to CD40 signaling include numerous cytokines and chemokines (IL-1, IL-6, IL-8, IL-10, IL-12, TNF-Alpha, and Macrophage Inflammatory Protein-1Alpha (MIP1Alpha). In certain cell types, activation of CD40 may result in production of cytotoxic radicals (Dadgostar et al., Supra), COX2 (Cyclooxygenase-2), and production of NO (Nitric Oxide).

The Role of CD40 in Tumors

CD40 is not only expressed by normal immune cells but also by many malignant cells. In particular, CD40 is overexpressed in B-lineage NHLs, chronic lymphocytic leukemias (CLLs), hairy cell leukemias (HCLs), Hodgkin's disease (Uckun F M, Gajl-Peczalska K, Myers D E, et al. Blood 1990; 76:2449-2456; O'Grady J T, Stewart S, Lowrey J, et al. Am J Pathol 1994; 144: 21-26), multiple myeloma (Pellat-Deceunynck C, Bataille R, Robillard N, Harousseau J L, Rapp M J, Juge-Morineau N, Wijdenes J, Amiot M. Blood. 1994; 84(8):2597-603), as well as in carcinomas of the bladder, kidney, ovary, cervix, breast, lung, nasopharynx, and malignant melanoma (Young L S, Eliopoulos A G, Gallagher N J, et al. Immunol Today 1998; 19:502-6; Ziebold J L, Hixon J, Boyd A, et al. Arch Immunol Ther Exp (Warsz) 2000; 48: 225-33; Gladue R, Cole S, Donovan C, et al. J Clin Oncol 2006; 24 (18S):103s).

Ligation of CD40 on the surface of tumor cells, which in many cases, mediates a direct cytotoxic effect, results in tumor regression through apoptosis and necrosis (Grewal I S, Flavell R A. Annu Rev Immunol 1998; 16:111-35; van Kooten C, Banchereau J. J Leukoc Biol 2000; 67(1):2-17). Although the exact functions of CD40 in tumor cells are unclear (Tong A W, Stone M J. Cancer Gene Ther. 2003 10(1):1-13), engagement of CD40 in vitro inhibits the growth of solid tumor cells and high-grade B cell lymphoma cells (Magi Khalil and Robert H. Vonderheide. Update Cancer Ther 2007; 2(2): 61-65; Young L S, Eliopoulos A G, Gallagher N J, Dawson C W. Immunol Today 1998; 19(11): 502-6; Funakoshi S, Longo D L, Beckwith M, et al. Blood 1994; 83(10):2787-94; Hess S, Engelmann H. J Exp Med 1996; 183(1):159-67; Eliopoulos A G, Dawson C W, Mosialos G, et al. Oncogene 1996; 13(10):2243-54; von Leoprechting A, van der Bruggen P, Pahl H L, Aruffo A, Simon J C. Cancer Res 1999; 59(6):1287-94). These effects contrast with proliferation induced after engagement of CD40 on non-neoplastic B cells and dendritic cells.

In addition to direct tumor inhibition, activation of CD40 signaling rescues the function of antigen-presenting cells in tumor-bearing hosts and triggers or restores active immune responses against tumor-associated antigens. CD40 agonists have been reported to overcome T-cell tolerance in tumor-bearing mice, evoke effective cytotoxic T-cell responses against tumor-associated antigens, and enhance the efficacy of antitumor vaccines (Eliopoulos A G, Davies C, Knox P G, et al. Mol Cell Biol 2000; 20(15): 5503-15; Tong A W, Papayoti M H, Netto G, et al. Clin Cancer Res 2001; 7(3):691-703).

CD40 as Molecular Target

CD40 is overexpressed on a wide range of malignant cells. The roles of CD40 in tumor inhibition and stimulation of the immune system make CD40 an attractive target for an antibody-based immunotherapy (van Mierlo G J, den Boer A T, Medema J P, et al. Proc Natl Acad Sci USA. 2002; 99(8): 5561-5566; French R R, Chan H T, Tutt A L, Glennie M J. Nat Med. 1999; 5(5):548-553). Anti-CD40 antibodies may act against cancer cells via multiple mechanisms: (i) antibody effector function such as ADCC, (ii) a direct cytotoxic effect on the tumor cells, and (iii) activation of anti-tumor immune responses.

Anti-CD40 Therapeutic Antibodies in Development

Several anti-CD40 antibodies have been reported to have potential as anti-tumor therapeutics. CP-870,893 is a fully human IgG$_2$ CD40 agonist antibody developed by Pfizer. It binds CD40 with a K$_D$ of $3.48 \times 10^{-10}$ M, but does not block binding of CD40L (see e.g., U.S. Pat. No. 7,338,660). CP-870893 has not shown ADCC effects; possibly due to its IgG2 isotype. Thus, this antibody acts as a CD40 agonist (i.e., does not affect CD40L binding), induces proapoptotic signaling, and activates DCs and immune surveillance. However, this antibody does not mediate ADCC.

HCD122 is a fully human IgG1 CD40 antagonist antibody developed by Novartis. It binds to CD40 with a K$_D$ of $5.1 \times 10^{-10}$ M, blocks CD40 binding to CD40L, inhibits CD40-ligand induced signaling and biological effects on B cells and certain primary CLL and MM cells (Tai Y T, et al. Cancer Res. 2005 Jul. 1; 65(13):5898-906; Luqman M, Klabunde S, et al: Blood 112:711-720, 2008). The major mechanism of action for its anti-tumor effect in vivo is ADCC (Long L, et al. 2005 IMF Oral Presentation and Abstract No. 3; Blood 2004, 104(11, Part 1): Abst 3281). Due to its antagonist feature, this antibody may not directly induce CD40-mediated anti-tumor immune response.

SGN-40 is a humanized IgG1 antibody developed by Seattle Genetics from mouse antibody clone S2C6, which was generated using a human bladder carcinoma cell line as the immunogen. It binds to CD40 with a K$_D$ of $1.0 \times 10^{-9}$ M and works through enhancing the interaction between CD40 and CD40L, thus exhibiting a partial agonist effect (Francisco J A, et al., Cancer Res, 60: 3225-31, 2000). SGN-40 delivers proliferation inhibitory and apoptosis signals to a panel of B lymphoma lines originated from high-grade non-Hodgkin's lymphoma and MM cells (Tai Y T, Catley L P, Mitsiades C S, et al. Cancer Res 2004; 64(8):2846-2852). In vitro and in vivo studies suggest that both apoptotic signaling and antibody effector function via ADCC contribute to antitumor activity of SGN-40 (Law C L, Gordon K A, Collier J, et al: Cancer Res 2005; 65:8331-8338). A Recent study suggested that the anti-tumour activity of SGN-40 significantly depends on Fc interactions with the effector cells and that macrophages are the major effectors contributing to its therapeutic activities (Oflazoglu E, et al. Br J Cancer. 2009 Jan. 13; 100(1):113-7. Epub 2008 Dec. 9). Since SGN-40 is a partial agonist and requires CD40L expressed on T cells, SGN-40 may have limited ability to fully boost the anti-tumor immune response.

Accordingly, there remains a need in the art for novel immunotherapeutics that target CD40 and that act as agonist for this target, activate dendritic cells and immune surveillance and which activate ADCC, thereby providing improved anti-cancer properties.

BRIEF SUMMARY

One aspect of the present disclosure provides an isolated antibody, or an antigen-binding fragment thereof, that binds to human CD40, comprising (i) a heavy chain variable region comprising the VHCDR1 region set forth in SEQ ID NO:3, the VHCDR2 region set forth in SEQ ID NO:4, and the VHCDR3 region set forth SEQ ID NO:5; and (ii) a light chain variable region comprising the VLCDR1 region set forth in SEQ ID NO:6, the VLCDR2 region set forth in SEQ ID NO:7, and the VLCDR3 region set forth in SEQ ID NO: 8; or a variant of said antibody, or an antigen-binding fragment thereof, comprising heavy and light chain variable regions identical to the heavy and light chain variable regions of (i) and (ii) except for up to 8 amino acid substitutions in said CDR regions. In one embodiment of the antibodies disclosed herein, the heavy chain variable region comprises the amino acid sequence set forth in SEQ ID NO:1. In a further embodiment, the light chain variable region comprises the amino acid sequence set forth in SEQ ID NO:2.

Another aspect of the present disclosure provides an isolated antibody, or an antigen-binding fragment thereof, that binds to human CD40, comprising a heavy chain variable region comprising the amino acid sequence set forth in SEQ ID NO:1. In one embodiment of this aspect, the isolated antibody, or antigen-binding fragment thereof comprises a light chain variable region which comprises an amino acid sequence having at least 90% identity to the amino acid sequence set forth in SEQ ID NO:2. In a further embodiment of this aspect, the isolated antibody, or an antigen-binding fragment thereof comprises a light chain variable region which comprises the amino acid sequence set forth in SEQ ID NO:2.

Yet a further aspect of the present disclosure provides an isolated antibody, or an antigen-binding fragment thereof, that binds to human CD40, comprising a light chain variable region comprising the amino acid sequence set forth in SEQ ID NO:2. In one embodiment of this aspect, the isolated antibody, or antigen binding fragment thereof comprises a heavy chain variable region which comprises an amino acid sequence having at least 90% identity to the amino acid sequence set forth in SEQ ID NO:1.

In certain embodiments, the isolated antibodies as disclosed herein are humanized. Illustrative humanized antibody variable regions are set forth in the VH region amino acid sequence of SEQ ID NO:9 and the VL region amino acid sequence of SEQ ID NO:10.

In one embodiment, an isolated antibody disclosed herein may be single chain antibody, a ScFv, a univalent antibody lacking a hinge region, a minibody, a Fab, a Fab' fragment, or a F(ab')$_2$ fragment. In certain embodiments, the antibodies herein are whole antibodies.

In another embodiment, the isolated antibodies as described herein comprise a human IgG constant domain, such as, but not limited to an IgG1 CH1 domain or an IgG1 Fc region.

A further embodiment of the disclosure provides an isolated antibody, or an antigen-binding fragment thereof, that competes with the anti-CD40 antibodies described herein for binding to human CD40.

In one aspect of this disclosure, the isolated antibody, or antigen-binding fragment thereof, that binds CD40, binds with a KD of 0.96 nM or lower. In a further embodiment, the isolated antibody, or antigen-binding fragment thereof, that binds CD40, binds with a Kd of between 1.1 nM and 0.90 nM. In a further embodiment, the isolated antibody, or antigen-binding fragment thereof, that binds CD40, binds with a Kd of about 1.2, 1.1, 1.0, 0.99, 0.98, 0.97, 0.96, 0.95, 0.94, 0.93, 0.92, 0.91, 0.90, 0.85, or about 0.80 nM. In another embodiment, the antibody binds CD40 with a Kd of about 2.5, 2.4, 2.3, 2.2, 2.1, 2.0, 1.9, 1.8, 1.7, 1.6, 1.5, 1.4, or 1.3 nM.

In a further aspect, the invention provides an isolated antibody, or antigen-binding fragment thereof as described herein, wherein the isolated antibody, or antigen-binding fragment thereof: blocks binding of CD40 to CD40L; is a CD40 agonist; activates antigen presenting cells; stimulates cytokine release from antigen presenting cells; induces tumor cell apoptosis; inhibits tumor cell proliferation; kills tumor cells via induction of effector functions selected from the group consisting of antibody dependent cellular cytotoxicity, complement dependent cytotoxicity, and antibody dependent cellular phagocytosis; stimulates anti-tumor T cell responses; reduces established tumors; inhibits rituximab-resistant tumors; or a combination of any one or more of the aforementioned.

Another aspect of the present invention provides an isolated antibody, or an antigen binding fragment thereof, that binds to CD40, comprising: (i) a heavy chain variable region comprising the VH CDR1, the VHCDR2, and VHCDR3 of any one of the VH regions shown in FIG. 16; and (ii) a light chain variable region comprising the VLCDR1, the VLCDR2, and the VLCDR3 region of the corresponding VL region of any one of the VL regions shown in FIG. 16; or a variant of said antibody, or an antigen binding fragment thereof, comprising heavy and light chain variable regions identical to the heavy and light chain variable regions of (i) and (ii) except for up to 8 amino acid substitutions in said CDR regions.

Yet another aspect of the present invention provides an isolated antibody, or an antigen binding fragment thereof that binds to CD40, comprising a heavy chain variable region comprising any one of the VH regions shown in FIG. 16. In one embodiment such an antibody further comprises a light chain variable region comprising an amino acid sequence having at least 90% identity to the corresponding VL region as shown in FIG. 16. In another embodiment, such an antibody or antigen binding fragment thereof further comprises the corresponding light chain variable region as shown in FIG. 16.

Yet another aspect of the present invention provides an isolated antibody, or an antigen binding fragment thereof that binds to CD40, comprising a light chain variable region comprising any one of the VL regions shown in FIG. 16. In one embodiment such an antibody further comprises a heavy chain variable region comprising an amino acid sequence having at least 90% identity to the corresponding VH region as shown in FIG. 16. In another embodiment, such an antibody or antigen binding fragment thereof further comprises the corresponding heavy chain variable region as shown in FIG. 16.

The present disclosure also provides isolated polynucleotides encoding the isolated antibodies, or antigen-binding fragments thereof as disclosed herein.

The present disclosure also provides compositions comprising a physiologically acceptable carrier and a therapeutically effective amount of an anti-CD40 antibody or antigen-binding fragment thereof as described herein.

Another aspect of the present disclosure provides a method for treating a patient having a cancer, comprising administering to the patient a composition comprising a physiologically acceptable carrier and a therapeutically effective amount of an anti-CD40 antibody or antigen-binding fragment thereof as described herein, thereby treating the cancer. In certain embodiments, the cancer is associated with aberrant CD40 expression. In further embodiments, the cancer is selected from the group consisting of non-Hodgkin's lymphomas, Hodgkin's lymphoma, chronic lymphocytic leukemias, hairy cell leukemias, acute lymphoblastic leukemias, multiple myeloma, carcinomas of the pancreas, colon, gastric intestine, prostate, bladder, kidney, ovary, cervix, breast, lung, nasopharynx, malignant melanoma and rituximab resistant NHL and leukemias.

Another aspect of the present disclosure provides a method for treating a patient having cancer and/or autoimmune disease, and/or inflammatory disease, comprising administering to the patient a composition comprising a physiologically acceptable carrier and a therapeutically effective amount of an anti-CD40 antibody or antigen-binding fragment thereof as described herein, thereby treating the patient having autoimmune and inflammatory diseases.

Another aspect of the present disclosure provides a method for ameliorating the symptoms in a patient having cancer, and/or autoimmune disease and/or inflammatory disease, comprising administering to the patient a composition comprising a physiologically acceptable carrier and a therapeutically effective amount of an anti-CD40 antibody or antigen-binding fragment thereof as described herein, thereby ameliorating the symptoms in the patient having cancer, and/or autoimmune and/or inflammatory diseases.

Another aspect of the present disclosure provides isolated antibody, or an antigen-binding fragment thereof, that binds to human CD40, comprising a heavy chain variable region comprising the amino acid sequence set forth in SEQ ID NO:11. In one embodiment, the isolated antibody, or an antigen-binding fragment thereof, that binds to human CD40, comprises a heavy chain variable region comprising the amino acid sequence set forth in SEQ ID NO:11 and comprises a light chain variable region which comprises an amino acid sequence having at least 90% identity to the amino acid sequence set forth in SEQ ID NO:22 or a light chain comprising the amino acid sequence set forth in SEQ ID NO:22. In certain embodiments, an isolated antibody described herein comprises the light chain as set forth in SEQ ID NO:22 and comprises a heavy chain variable region which comprises an amino acid sequence having at least 90% identity to the amino acid sequence set forth in SEQ ID NO:11.

A further aspect of the present disclosure provides an isolated antibody, or an antigen-binding fragment thereof, that binds to human CD40, comprising a heavy chain variable region comprising the amino acid sequence set forth in SEQ ID NO:13. In one embodiment, the antibody comprises a heavy chain variable region comprising the amino acid sequence set forth in SEQ ID NO:13 and a light chain variable region which comprises an amino acid sequence having at least 90% identity to the amino acid sequence set forth in SEQ ID NO:24. In one embodiment, the light chain comprises the amino acid sequence set forth in SEQ ID NO:24.

A further aspect of the present disclosure provides an isolated antibody, or an antigen-binding fragment thereof, that binds to human CD40, comprising a light chain variable region comprising the amino acid sequence set forth in SEQ ID NO:24. In one embodiment, the antibody comprises a light chain variable region comprising the amino acid sequence set forth in SEQ ID NO:24 and a heavy chain variable region which comprises an amino acid sequence having at least 90% identity to the amino acid sequence set forth in SEQ ID NO:13.

In certain aspects, the isolated antibody, or antigen-binding fragment thereof, that binds CD40 comprises a heavy chain variable region which comprises the amino acid sequence set forth in SEQ ID NO:17. In one embodiment, the isolated antibody that binds CD40 comprises a heavy chain variable region comprising the amino acid sequence set forth in SEQ ID NO:17 and a light chain variable region which comprises an amino acid sequence having at least 90% identity to the amino acid sequence set forth in SEQ ID NO:28. In one embodiment, the light chain variable region comprises the amino acid sequence set forth in SEQ ID NO:28.

Another aspect of the disclosure provides an isolated antibody, or an antigen-binding fragment thereof, that binds to human CD40, comprising a light chain variable region comprising the amino acid sequence set forth in SEQ ID NO:28. In one embodiment, the isolated antibody, or an antigen-binding fragment thereof, that binds to human CD40, comprises a light chain variable region comprising the amino acid sequence set forth in SEQ ID NO:28 and a heavy chain variable region which comprises an amino acid sequence having at least 90% identity to the amino acid sequence set forth in SEQ ID NO:17.

Another aspect of the disclosure provides an isolated antibody, or an antigen-binding fragment thereof, that binds to human CD40, comprising a heavy chain variable region comprising the amino acid sequence set forth in SEQ ID NO:19. In one embodiment, the isolated antibody, or an antigen-binding fragment thereof, that binds to human CD40, comprises a heavy chain variable region comprising the amino acid sequence set forth in SEQ ID NO:19 and a light chain variable region which comprises an amino acid sequence having at least 90% identity to the amino acid sequence set forth in SEQ ID NO:30. In one particular embodiment, the light chain variable region comprises the amino acid sequence set forth in SEQ ID NO:30.

Yet a further aspect of the present disclosure provides an isolated antibody, or an antigen-binding fragment thereof, that binds to human CD40, comprising a light chain variable region comprising the amino acid sequence set forth in SEQ ID NO:30. In one embodiment, the isolated antibody, or an antigen-binding fragment thereof, that binds to human CD40, comprises a light chain variable region comprising the amino acid sequence set forth in SEQ ID NO:30 and a heavy chain variable region which comprises an amino acid sequence having at least 90% identity to the amino acid sequence set forth in SEQ ID NO:19.

Another aspect of the present disclosure provides an isolated antibody, or an antigen-binding fragment thereof, that binds to human CD40, comprising a heavy chain variable region that comprises heavy chain variable region CDRs and a light chain variable region that comprises corresponding light chain variable region CDRs, wherein the CDRs are as shown in FIG. 16.

Another aspect of the present invention provides an isolated antibody, or antigen-binding fragment thereof, that binds to a CD40 epitope set forth in any one or more of SEQ ID NOs: 196, 197, 199 and 202. In one particular embodiment, the isolated antibody, or antigen binding fragment thereof binds to the CD40 epitope set forth in SEQ ID NO: 202. In another embodiment, an isolated antibody, or anti-gen-binding fragment thereof, that binds to the CD40 epitopes set forth in SEQ ID NOs: 196, 197, 199 or 202, does not comprise the CDRs set forth in SEQ ID NOs:3-8. In one embodiment, the isolated antibody that binds to a CD40 epitope set forth in any one or more of SEQ ID NOs: 196, 197, 199 and 202, comprises (i) a heavy chain variable region comprising the VHCDR1 region set forth in SEQ ID NO:3, the VHCDR2 region set forth in SEQ ID NO:4, and the VHCDR3 region set forth SEQ ID NO:5; and (ii) a light chain variable region comprising the VLCDR1 region set forth in SEQ ID NO:6, the VLCDR2 region set forth in SEQ ID NO:7, and the VLCDR3 region set forth in SEQ ID NO:8; or a variant of said antibody, or an antigen-binding fragment thereof, comprising heavy and light chain variable regions identical to the heavy and light chain variable regions of (i) and (ii) except for up to 8 amino acid substitutions in said CDR regions; said isolated antibody, or an antigen-binding fragment thereof, further comprising an Fc region modified such that the isolated antibody, or an antigen binding fragment thereof, has increased binding affinity to FcγRIIB, increased ADCC, or increased anti-CD40 agonist activity, or a combination thereof, as compared to said isolated antibody, or an antigen binding fragment thereof, comprising an unmodified version of said Fc region. In this regard, the Fc region may comprise a S267E mutation.

The present disclosure also provides isolated polynucleotides encoding the isolated antibodies, or antigen-binding fragments thereof, that bind to a CD40 epitope set forth in any one or more of SEQ ID NOs: 196, 197, 199 and 202; expression vectors comprising the isolated polynucleotide, and isolated host cells comprising such vector.

The present disclosure also provides compositions comprising a physiologically except a carrier and a therapeutically effective amount of the isolated antibodies, or antigen binding fragment thereof, that bind to a CD40 epitope set forth in any one or more of SEQ ID NOs: 196, 197, 199 and 202.

The present invention further provides methods for treating or ameliorating cancer in a patient comprising administering to the patient the compositions comprising the antibodies that bind to a CD40 epitope set forth in any one or more of SEQ ID NOs: 196, 197, 199 and 202, as described herein. In this regard, the cancer may be non-Hodgkin's lymphomas, Hodgkin's lymphoma, chronic lymphocytic leukemias, hairy cell leukemias, acute lymphoblastic leukemias, multiple myeloma, carcinomas of the bladder, kidney ovary, cervix, breast, lung, nasopharynx, malignant melanoma or rituximab resistant NHL or leukemias.

The present invention also provides methods for ameliorating symptoms of autoimmune disease or inflammatory disease in a patient by administering to the patient the compositions comprising the antibodies that bind to a CD40 epitope set forth in any one or more of SEQ ID NOs: 196, 197, 199 and 202.

BRIEF DESCRIPTION OF THE SEQUENCES

SEQ ID NO:1 is the amino acid sequence of the VH region of the R-8 rabbit anti-CD40 antibody.

SEQ ID NO:2 is the amino acid sequence of the VL region of the R-8 rabbit anti-CD40 antibody.

SEQ ID NO:3 is the amino acid sequence of the VHCDR1 region of the R-8 rabbit anti-CD40 antibody.

SEQ ID NO:4 is the amino acid sequence of the VHCDR2 region of the R-8 rabbit anti-CD40 antibody.

SEQ ID NO:5 is the amino acid sequence of the VHCDR3 region of the R-8 rabbit anti-CD40 antibody.

SEQ ID NO:6 is the amino acid sequence of the VLCDR1 region of the R-8 rabbit anti-CD40 antibody.

SEQ ID NO:7 is the amino acid sequence of the VLCDR2 region of the R-8 rabbit anti-CD40 antibody.

SEQ ID NO:8 is the amino acid sequence of the VLCDR3 region of the R-8 rabbit anti-CD40 antibody.

SEQ ID NO:9 is the amino acid sequence of the VH region of APX005, the humanized version of the R-8 rabbit anti-CD40 antibody, without a signal peptide.

SEQ ID NO:10 is the amino acid sequence of the VL region of APX005, the humanized version of the R-8 rabbit anti-CD40 antibody, without a signal peptide.

SEQ ID NOs:11-21 and 33-44 are heavy chain amino acid sequences of rabbit anti-CD40 antibody candidates that showed functional activity (see FIG. 16).

SEQ ID NOs:22-32 and 45-56 are light chain amino acid sequences of rabbit anti-CD40 antibody candidates that showed functional activity (see FIG. 16).

SEQ ID NOs:57-79 are the VHCDR1 amino acid sequences for the anti-CD40 antibodies shown in FIG. 16.

SEQ ID NOs:80-102 are the VHCDR2 amino acid sequences for the anti-CD40 antibodies shown in FIG. 16.

SEQ ID NOs:103-125 are the VHCDR3 amino acid sequences for the anti-CD40 antibodies shown in FIG. 16.

SEQ ID NOs:126-148 are the VLCDR1 amino acid sequences for the anti-CD40 antibodies shown in FIG. 16.

SEQ ID NOs:149-171 are the VLCDR2 amino acid sequences for the anti-CD40 antibodies shown in FIG. 16.

SEQ ID NOs:172-194 are the VLCDR3 amino acid sequences for the anti-CD40 antibodies shown in FIG. 16.

SEQ ID NO:195 is the amino acid sequence of the human IgG1 heavy chain constant region comprising an Fc region with a S267E substitution.

SEQ ID NO: 196 is amino acids 92-107 of human CD40, identified as an epitope bound by the APX005 antibody.

SEQ ID NO: 197 is amino acids 125-144 of human CD40, identified as an epitope bound by the APX005 antibody.

SEQ ID NO:198 is the amino acid sequence of human CD40.

SEQ ID NO: 199 is the amino acid sequence of a CD40 CLIPS peptide, from residue 84-102 of CD40.

SEQ ID NO:200 is the amino acid sequence of residues 84-102 of CD40 with serine substitutions for the cysteine residues at position 91 and 96.

SEQ ID NO:201 is the amino acid residues 122-125 of human CD40.

SEQ ID NO:202 is the amino acid residues 92-102 of human CD40 bound by the APX005 antibody.

BRIEF DESCRIPTION OF THE DRAWINGS

FIG. 16A-16L is a sequence alignment of rabbit anti-CD40 heavy (FIGS. 16A-16F) and light chain (FIGS. 16G-16L) antibody sequences. Heavy and light chain CDRs 1-3 are underlined. SEQ ID NOs are as follows: Heavy chain: R-3 and R-6: SEQ ID NOs:11, 12; R-8: SEQ ID NO:1; R-9, -16, -18, -24, -33, -36, 19-21, -45, -59: SEQ ID NOs:13-21, respectively; R-2, R-5, R-7, R-10, R-12, R-20, R-26, R-30, R-35, 19-35, 19-41, 19-57: SEQ ID Nos:33-44, respectively. Light chain: R-3 and R-6: SEQ ID NOs:22 and 23; R-8: SEQ ID NO:2; R-9, -16, -18, -24, -33, -36, 19-21, -45, -59: SEQ ID NOs:24-32, respectively; R-2, R-5, R-7, R-10, R-12, R-20, R-26, R-30, R-35, 19-35, 19-41, 19-57: SEQ ID Nos:45-56, respectively. The amino acid sequences include the VH and VL signal peptide. The R-8 VHCDR and VLCDR amino acid sequences are set forth in SEQ ID Nos:3-8. The VHCDR amino acid sequences and the VLCDR amino acid sequences for the remaining antibodies are set forth in SEQ ID Nos:57-125 and SEQ ID Nos:126-194, respectively.

DETAILED DESCRIPTION

Figure 1A:
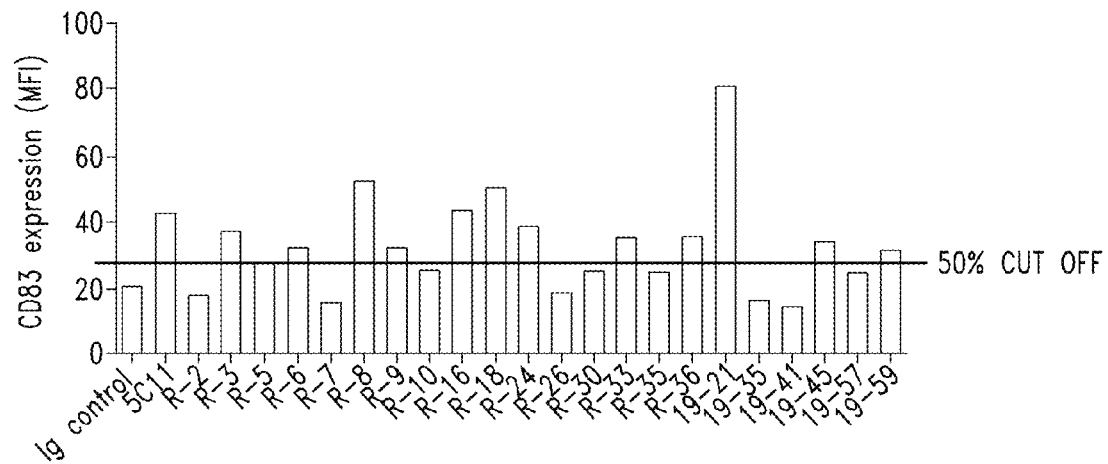
FIG. 1A-1D show the results of screening agonist antibodies by measuring DC maturation and T cell activation as described in Example 1. 1A: CD83 expression; 1B: CD80 expression; 1C: CD86 expression; 1D: T cell proliferation in a mixed lymphocyte reaction.

The present disclosure relates to antibodies and antigen-binding fragments thereof the specifically bind to CD40 in particular antibodies having specific epitopic specificity and functional properties. One embodiment of the invention encompasses specific humanized antibodies and fragments thereof capable of binding to CD40 and functions as a CD40 agonist by inducing/enhancing CD40-mediated downstream cell signaling and biological effects. In more specific embodiments of the invention, the antibodies described herein specifically bind to CD40 with very high affinity, such as an affinity of at least between 980 and 950 picomolar, at least between 970 and 950 picomolar, and in certain embodiments with an affinity of 960 picomolar. The antibodies described herein, among other attributes, induce CD40 signaling in tumor cells, activate dendritic cells and immune surveillance, activate antibody dependent cellular cytotoxicity (ADCC) against tumor cells, block binding of CD40 to CD40L; have CD40 agonistic activity; activate antigen presenting cells; stimulate cytokine release from antigen presenting cells; induce tumor cell apoptosis; Inhibit tumor cell proliferation; kill tumor cells via induction of effector functions including but not limited to ADCC, CDC and ADCP; stimulate anti-tumor T cell responses; reduce established tumors; and inhibit rituximab-resistant tumors. The antibodies described herein may have or induce a combination of any one or more of these attributes or activities.

Embodiments of the invention pertain to the use of anti-CD40 antibodies or antigen-binding fragments thereof for the diagnosis, assessment and treatment of diseases and disorders associated with CD40 or aberrant expression thereof. The subject antibodies are used in the treatment or prevention of cancers including, but not limited to, non-Hodgkin's lymphomas, Hodgkin's lymphoma, chronic lymphocytic leukemias, hairy cell leukemias, acute lymphoblastic leukemias, multiple myeloma, carcinomas of the bladder, kidney ovary, cervix, breast, lung, nasopharynx, malignant melanoma and rituximab resistant NHL and leukemias, autoimmune diseases and inflammatory diseases among other diseases.

The practice of the present invention will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., *Current Protocols in Molecular Biology* or *Current Protocols in Immunology*, John Wiley & Sons, New York, N.Y. (2009); Ausubel et al., *Short Protocols in Molecular Biology*, 3$^{rd}$ ed., Wiley & Sons, 1995; Sambrook and Russell, *Molecular Cloning: A Laboratory Manual* (3rd Edition, 2001); Maniatis et al. *Molecular Cloning: A Laboratory Manual* (1982); *DNA Cloning: A Practical Approach*, vol. I & II (D. Glover, ed.); *Oligonucleotide Synthesis* (N. Gait, ed., 1984); *Nucleic Acid Hybridization* (B. Hames & S. Higgins, eds., 1985); *Transcription and Translation* (B. Hames & S. Higgins, eds., 1984); *Animal Cell Culture* (R. Freshney, ed., 1986); Perbal, *A Practical Guide to Molecular Cloning* (1984) and other like references.

As used in this specification and the appended claims, the singular forms "a," "an" and "the" include plural references unless the content clearly dictates otherwise.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Each embodiment in this specification is to be applied mutatis mutandis to every other embodiment unless expressly stated otherwise.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. These and related techniques and procedures may be generally performed according to conventional methods well known in the art and as described in various general and more specific references that are cited and discussed throughout the present specification. Unless specific definitions are provided, the nomenclature utilized in connection with, and the laboratory procedures and techniques of, molecular biology, analytical chemistry, synthetic organic chemistry, and medicinal and pharmaceutical chemistry described herein are those well-known and commonly used in the art. Standard techniques may be used for recombinant technology, molecular biological, microbiological, chemical syntheses, chemical analyses, pharmaceutical preparation, formulation, and delivery, and treatment of patients.

Embodiments of the present invention relate to antibodies that bind to CD40. In particular, the antibodies described herein specifically bind to CD40 with unexpectedly high affinity, enhance CD40 signaling activity, activate the immune system, activate ADCC and have therapeutic utility for the treatment of diseases associated with aberrant expression CD40.

Sequences of illustrative antibodies, or antigen-binding fragments, or complementarity determining regions (CDRs) thereof, are set forth in SEQ ID NOs:1-194.

As is well known in the art, an antibody is an immunoglobulin molecule capable of specific binding to a target, such as a carbohydrate, polynucleotide, lipid, polypeptide, etc., through at least one epitope recognition site, located in the variable region of the immunoglobulin molecule. As used herein, the term encompasses not only intact polyclonal or monoclonal antibodies, but also fragments thereof (such as dAb, Fab, Fab', F(ab')$_2$, Fv), single chain (ScFv), synthetic variants thereof, naturally occurring variants, fusion proteins comprising an antibody portion with an antigen-binding fragment of the required specificity, humanized antibodies, chimeric antibodies, and any other modified configuration of the immunoglobulin molecule that comprises an antigen-binding site or fragment (epitope recognition site) of the required specificity. "Diabodies", multivalent or multispecific fragments constructed by gene fusion (WO94/13804; P. Holliger et al., Proc. Natl. Acad. Sci. USA 90 6444-6448, 1993) are also a particular form of antibody contemplated herein. Minibodies comprising a scFv joined to a CH3 domain are also included herein (S. Hu et al., Cancer Res., 56, 3055-3061, 1996). See e.g., Ward, E. S. et al., Nature 341, 544-546 (1989); Bird et al., Science, 242, 423-426, 1988; Huston et al., PNAS USA, 85, 5879-5883, 1988); PCT/US92/09965; WO94/13804; P. Holliger et al., Proc. Natl. Acad. Sci. USA 90 6444-6448, 1993; Y. Reiter et al., Nature Biotech, 14, 1239-1245, 1996; S. Hu et al., Cancer Res., 56, 3055-3061, 1996.

The term "antigen-binding fragment" as used herein refers to a polypeptide fragment that contains at least one CDR of an immunoglobulin heavy and/or light chains that binds to the antigen of interest, in particular to CD40. In this regard, an antigen-binding fragment of the herein described antibodies may comprise 1, 2, 3, 4, 5, or all 6 CDRs of a VH and VL sequence set forth herein from antibodies that bind CD40. An antigen-binding fragment of the CD40-specific antibodies described herein is capable of binding to CD40. In certain embodiments, an antigen-binding fragment or an antibody comprising an antigen-binding fragment, prevents or inhibits CD40L binding to the CD40. In certain embodiments, the antigen-binding fragment binds specifically to and/or enhances or modulates the biological activity of human CD40. Such biological activity includes, but is not limited to, cell signaling, activation of dendritic cells, The term "antigen" refers to a molecule or a portion of a molecule capable of being bound by a selective binding agent, such as an antibody, and additionally capable of being used in an animal to produce antibodies capable of binding to an epitope of that antigen. An antigen may have one or more epitopes.

The term "epitope" includes any determinant, preferably a polypeptide determinant, capable of specific binding to an immunoglobulin or T-cell receptor. An epitope is a region of an antigen that is bound by an antibody. In certain embodiments, epitope determinants include chemically active surface groupings of molecules such as amino acids, sugar side chains, phosphoryl or sulfonyl, and may in certain embodiments have specific three-dimensional structural characteristics, and/or specific charge characteristics. In certain embodiments, an antibody is said to specifically bind an antigen when it preferentially recognizes its target antigen in a complex mixture of proteins and/or macromolecules. An antibody is said to specifically bind an antigen when the equilibrium dissociation constant is $\leq 10^{-7}$ or $10^{-8}$ M. In some embodiments, the equilibrium dissociation constant may be $\leq 10^{-9}$ M or $\leq 10^{-10}$ M.

In certain embodiments, antibodies and antigen-binding fragments thereof as described herein include a heavy chain and a light chain CDR set, respectively interposed between a heavy chain and a light chain framework region (FR) set which provide support to the CDRs and define the spatial relationship of the CDRs relative to each other. As used herein, the term "CDR set" refers to the three hypervariable regions of a heavy or light chain V region. Proceeding from the N-terminus of a heavy or light chain, these regions are denoted as "CDR1," "CDR2," and "CDR3" respectively. An antigen-binding site, therefore, includes six CDRs, comprising the CDR set from each of a heavy and a light chain V region. A polypeptide comprising a single CDR, (e.g., a CDR1, CDR2 or CDR3) is referred to herein as a "molecular recognition unit." Crystallographic analysis of a number of antigen-antibody complexes has demonstrated that the amino acid residues of CDRs form extensive contact with bound antigen, wherein the most extensive antigen contact is with the heavy chain CDR3. Thus, the molecular recognition units are primarily responsible for the specificity of an antigen-binding site.

As used herein, the term "FR set" refers to the four flanking amino acid sequences which frame the CDRs of a CDR set of a heavy or light chain V region. Some FR residues may contact bound antigen; however, FRs are primarily responsible for folding the V region into the antigen-binding site, particularly the FR residues directly adjacent to the CDRs. Within FRs, certain amino residues and certain structural features are very highly conserved. In this regard, all V region sequences contain an internal disulfide loop of around 90 amino acid residues. When the V regions fold into a binding-site, the CDRs are displayed as projecting loop motifs which form an antigen-binding surface. It is generally recognized that there are conserved structural regions of FRs which influence the folded shape of the CDR loops into certain "canonical" structures—regardless of the precise CDR amino acid sequence. Further, certain FR residues are known to participate in non-covalent interdomain contacts which stabilize the interaction of the antibody heavy and light chains.

The structures and locations of immunoglobulin variable domains may be determined by reference to Kabat, E. A. et al., Sequences of Proteins of Immunological Interest. 4th Edition. US Department of Health and Human Services. 1987, and updates thereof, now available on the Internet (immuno.bme.nwu.edu).

A "monoclonal antibody" refers to a homogeneous antibody population wherein the monoclonal antibody is comprised of amino acids (naturally occurring and non-naturally occurring) that are involved in the selective binding of an epitope. Monoclonal antibodies are highly specific, being directed against a single epitope. The term "monoclonal antibody" encompasses not only intact monoclonal antibodies and full-length monoclonal antibodies, but also fragments thereof (such as Fab, Fab', F(ab')$_2$, Fv), single chain (ScFv), variants thereof, fusion proteins comprising an antigen-binding portion, humanized monoclonal antibodies, chimeric monoclonal antibodies, and any other modified configuration of the immunoglobulin molecule that comprises an antigen-binding fragment (epitope recognition site) of the required specificity and the ability to bind to an epitope. It is not intended to be limited as regards the source of the antibody or the manner in which it is made (e.g., by hybridoma, phage selection, recombinant expression, transgenic animals, etc.). The term includes whole immunoglobulins as well as the fragments etc. described above under the definition of "antibody".

The proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the F(ab')$_2$ fragment which comprises both antigen-binding sites. An Fv fragment for use according to certain embodiments of the present invention can be produced by preferential proteolytic cleavage of an IgM, and on rare occasions of an IgG or IgA immunoglobulin molecule. Fv fragments are, however, more commonly derived using recombinant techniques known in the art. The Fv fragment includes a non-covalent $V_H$::$V_L$ heterodimer including an antigen-binding site which retains much of the antigen recognition and binding capabilities of the native antibody molecule. Inbar et al. (1972) *Proc. Nat. Acad. Sci. USA* 69:2659-2662; Hochman et al. (1976) *Biochem* 15:2706-2710; and Ehrlich et al. (1980) *Biochem* 19:4091-4096.

In certain embodiments, single chain Fv or scFV antibodies are contemplated. For example, Kappa bodies (111 et al., *Prot. Eng.* 10: 949-57 (1997); minibodies (Martin et al., *EMBO J* 13: 5305-9 (1994); diabodies (Holliger et al., *PNAS* 90: 6444-8 (1993); or Janusins (Traunecker et al., *EMBO J* 10: 3655-59 (1991) and Traunecker et al., *Int. J. Cancer Suppl.* 7: 51-52 (1992), may be prepared using standard molecular biology techniques following the teachings of the present application with regard to selecting antibodies having the desired specificity. In still other embodiments, bispecific or chimeric antibodies may be made that encompass the ligands of the present disclosure. For example, a chimeric antibody may comprise CDRs and framework regions from different antibodies, while bispecific antibodies may be generated that bind specifically to CD40 through one binding domain and to a second molecule through a second binding domain. These antibodies may be produced through recombinant molecular biological techniques or may be physically conjugated together.

A single chain Fv (sFv) polypeptide is a covalently linked $V_H$::$V_L$ heterodimer which is expressed from a gene fusion including $V_H$- and $V_L$-encoding genes linked by a peptide-encoding linker. Huston et al. (1988) *Proc. Nat. Acad. Sci. USA* 85(16):5879-5883. A number of methods have been described to discern chemical structures for converting the naturally aggregated—but chemically separated-light and heavy polypeptide chains from an antibody V region into an sFv molecule which will fold into a three dimensional structure substantially similar to the structure of an antigen-binding site. See, e.g., U.S. Pat. Nos. 5,091,513 and 5,132,405, to Huston et al.; and U.S. Pat. No. 4,946,778, to Ladner et al.

In certain embodiments, a CD40 binding antibody as described herein is in the form of a diabody. Diabodies are multimers of polypeptides, each polypeptide comprising a first domain comprising a binding region of an immunoglobulin light chain and a second domain comprising a binding region of an immunoglobulin heavy chain, the two domains being linked (e.g. by a peptide linker) but unable to associate with each other to form an antigen binding site: antigen binding sites are formed by the association of the first domain of one polypeptide within the multimer with the second domain of another polypeptide within the multimer (WO94/13804).

A dAb fragment of an antibody consists of a VH domain (Ward, E. S. et al., *Nature* 341, 544-546 (1989)).

Where bispecific antibodies are to be used, these may be conventional bispecific antibodies, which can be manufactured in a variety of ways (Holliger, P. and Winter G. *Current Opinion Biotechnol.* 4, 446-449 (1993)), e.g. prepared chemically or from hybrid hybridomas, or may be any of the bispecific antibody fragments mentioned above. Diabodies and scFv can be constructed without an Fc region, using only variable domains, potentially reducing the effects of anti-idiotypic reaction.

Bispecific diabodies, as opposed to bispecific whole antibodies, may also be particularly useful because they can be readily constructed and expressed in *E. coli*. Diabodies (and many other polypeptides such as antibody fragments) of appropriate binding specificities can be readily selected using phage display (WO94/13804) from libraries. If one arm of the diabody is to be kept constant, for instance, with a specificity directed against antigen X, then a library can be made where the other arm is varied and an antibody of appropriate specificity selected. Bispecific whole antibodies may be made by knobs-into-holes engineering (J. B. B. Ridgeway et al., *Protein Eng.*, 9, 616-621, 1996).

In certain embodiments, the antibodies described herein may be provided in the form of a UniBody®. A UniBody® is an IgG4 antibody with the hinge region removed (see GenMab Utrecht, The Netherlands; see also, e.g., US20090226421). This proprietary antibody technology creates a stable, smaller antibody format with an anticipated longer therapeutic window than current small antibody formats. IgG4 antibodies are considered inert and thus do not interact with the immune system. Fully human IgG4 antibodies may be modified by eliminating the hinge region of the antibody to obtain half-molecule fragments having distinct stability properties relative to the corresponding intact IgG4 (GenMab, Utrecht). Halving the IgG4 molecule leaves only one area on the UniBody® that can bind to cognate antigens (e.g., disease targets) and the UniBody® therefore binds univalently to only one site on target cells. For certain cancer cell surface antigens, this univalent binding may not stimulate the cancer cells to grow as may be seen using bivalent antibodies having the same antigen specificity, and hence UniBody® technology may afford treatment options for some types of cancer that may be refractory to treatment with conventional antibodies. The small size of the UniBody® can be a great benefit when treating some forms of cancer, allowing for better distribution of the molecule over larger solid tumors and potentially increasing efficacy.

In certain embodiments, the antibodies of the present disclosure may take the form of a Nanobody®. Nanobodies® are encoded by single genes and are efficiently produced in almost all prokaryotic and eukaryotic hosts e.g. *E. coli* (see e.g. U.S. Pat. No. 6,765,087), molds (for example *Aspergillus* or *Trichoderma*) and yeast (for example *Saccharomyces, Kluyvermyces, Hansenula* or *Pichia* (see e.g. U.S. Pat. No. 6,838,254). The production process is scalable and multi-kilogram quantities of Nanobodies® have been produced. Nanobodies® may be formulated as a ready-to-use solution having a long shelf life. The Nanoclone® method (see, e.g., WO 06/079372) is a proprietary method for generating Nanobodies against a desired target, based on automated high-throughput selection of B-cells.

In certain embodiments, the anti-CD40 antibodies or antigen-binding fragments thereof as disclosed herein are humanized. This refers to a chimeric molecule, generally prepared using recombinant techniques, having an antigen-binding site derived from an immunoglobulin from a non-human species and the remaining immunoglobulin structure of the molecule based upon the structure and/or sequence of a human immunoglobulin. The antigen-binding site may comprise either complete variable domains fused onto constant domains or only the CDRs grafted onto appropriate framework regions in the variable domains. Epitope binding sites may be wild type or modified by one or more amino acid substitutions. This eliminates the constant region as an immunogen in human individuals, but the possibility of an immune response to the foreign variable region remains (LoBuglio, A. F. et al., (1989) *Proc Natl Acad Sci USA* 86:4220-4224; Queen et al., *PNAS* (1988) 86:10029-10033; Riechmann et al., *Nature* (1988) 332:323-327). Illustrative methods for humanization of the anti-CD40 antibodies disclosed herein include the methods described in U.S. Pat. No. 7,462,697. Illustrative humanized antibodies according to certain embodiments of the present invention comprise the humanized sequences provided in SEQ ID NOs:9 and 10.

Another approach focuses not only on providing human-derived constant regions, but modifying the variable regions as well so as to reshape them as closely as possible to human form. It is known that the variable regions of both heavy and light chains contain three complementarity-determining regions (CDRs) which vary in response to the epitopes in question and determine binding capability, flanked by four framework regions (FRs) which are relatively conserved in a given species and which putatively provide a scaffolding for the CDRs. When nonhuman antibodies are prepared with respect to a particular epitope, the variable regions can be "reshaped" or "humanized" by grafting CDRs derived from nonhuman antibody on the FRs present in the human antibody to be modified. Application of this approach to various antibodies has been reported by Sato, K., et al., (1993) *Cancer Res* 53:851-856. Riechmann, L., et al., (1988) *Nature* 332:323-327; Verhoeyen, M., et al., (1988) *Science* 239:1534-1536; Kettleborough, C. A., et al., (1991) *Protein Engineering* 4:773-3783; Maeda, H., et al., (1991) *Human Antibodies Hybridoma* 2:124-134; Gorman, S. D., et al., (1991) *Proc Natl Acad Sci USA* 88:4181-4185; Tempest, P. R., et al., (1991) *Bio/Technology* 9:266-271; Co, M. S., et al., (1991) *Proc Natl Acad Sci USA* 88:2869-2873; Carter, P., et al., (1992) *Proc Natl Acad Sci USA* 89:4285-4289; and Co, M. S. et al., (1992) *J Immunol* 148:1149-1154. In some embodiments, humanized antibodies preserve all CDR sequences (for example, a humanized mouse antibody which contains all six CDRs from the mouse antibodies). In other embodiments, humanized antibodies have one or more CDRs (one, two, three, four, five, six) which are altered with respect to the original antibody, which are also termed one or more CDRs "derived from" one or more CDRs from the original antibody.

In certain embodiments, the antibodies of the present disclosure may be chimeric antibodies. In this regard, a chimeric antibody is comprised of an antigen-binding fragment of an anti-CD40 antibody operably linked or otherwise fused to a heterologous Fc portion of a different antibody. In certain embodiments, the heterologous Fc domain is of human origin. In other embodiments, the heterologous Fc domain may be from a different Ig class from the parent antibody, including IgA (including subclasses IgA1 and IgA2), IgD, IgE, IgG (including subclasses IgG1, IgG2, IgG3, and IgG4), and IgM. In further embodiments, the heterologous Fc domain may be comprised of CH2 and CH3 domains from one or more of the different Ig classes. As noted above with regard to humanized antibodies, the anti-CD40 antigen-binding fragment of a chimeric antibody may comprise only one or more of the CDRs of the antibodies described herein (e.g., 1, 2, 3, 4, 5, or 6 CDRs of the antibodies described herein), or may comprise an entire variable domain (VL, VH or both).

In certain embodiments, a CD40-binding antibody comprises one or more of the CDRs of the antibodies described herein. In this regard, it has been shown in some cases that the transfer of only the VHCDR3 of an antibody can be performed while still retaining desired specific binding (Barbas et al., *PNAS* (1995) 92: 2529-2533). See also, McLane et al., *PNAS* (1995) 92:5214-5218, Barbas et al., *J. Am. Chem. Soc.* (1994) 116:2161-2162.

Marks et al (*Bio/Technology,* 1992, 10:779-783) describe methods of producing repertoires of antibody variable domains in which consensus primers directed at or adjacent to the 5' end of the variable domain area are used in conjunction with consensus primers to the third framework region of human VH genes to provide a repertoire of VH variable domains lacking a CDR3. Marks et al further describe how this repertoire may be combined with a CDR3 of a particular antibody. Using analogous techniques, the CDR3-derived sequences of the presently described antibodies may be shuffled with repertoires of VH or VL domains lacking a CDR3, and the shuffled complete VH or VL domains combined with a cognate VL or VH domain to provide an antibody or antigen-binding fragment thereof that binds CD40. The repertoire may then be displayed in a suitable host system such as the phage display system of WO92/01047 so that suitable antibodies or antigen-binding fragments thereof may be selected. A repertoire may consist of at least from about $10^4$ individual members and upwards by several orders of magnitude, for example, to about from $10^6$ to $10^8$ or $10^{10}$ or more members. Analogous shuffling or combinatorial techniques are also disclosed by Stemmer (Nature, 1994, 370:389-391), who describes the technique in relation to a β-lactamase gene but observes that the approach may be used for the generation of antibodies.

A further alternative is to generate novel VH or VL regions carrying one or more CDR-derived sequences of the herein described invention embodiments using random mutagenesis of one or more selected VH and/or VL genes to generate mutations within the entire variable domain. Such a technique is described by Gram et al (1992, Proc. Natl. Acad. Sci., USA, 89:3576-3580), who used error-prone PCR. Another method which may be used is to direct mutagenesis to CDR regions of VH or VL genes. Such techniques are disclosed by Barbas et al., (1994, Proc. Natl. Acad. Sci., USA, 91:3809-3813) and Schier et al (1996, J. Mol. Biol. 263:551-567).

In certain embodiments, a specific VH and/or VL of the antibodies described herein may be used to screen a library of the complementary variable domain to identify antibodies with desirable properties, such as increased affinity for CD40. Such methods are described, for example, in Portolano et al., J. Immunol. (1993) 150:880-887; Clarkson et al., Nature (1991) 352:624-628.

Other methods may also be used to mix and match CDRs to identify antibodies having desired binding activity, such as binding to CD40. For example: Klimka et al., *British Journal of Cancer* (2000) 83: 252-260, describe a screening process using a mouse VL and a human VH library with CDR3 and FR4 retained from the mouse VH. After obtaining antibodies, the VH was screened against a human VL library to obtain antibodies that bound antigen. Beiboer et al., J. Mol. Biol. (2000) 296:833-849 describe a screening process using an entire mouse heavy chain and a human light chain library. After obtaining antibodies, one VL was combined with a human VH library with the CDR3 of the mouse retained. Antibodies capable of binding antigen were obtained. Rader et al., PNAS (1998) 95:8910-8915 describe a process similar to Beiboer et al above.

These just-described techniques are, in and of themselves, known as such in the art. The skilled person will, however, be able to use such techniques to obtain antibodies or antigen-binding fragments thereof according to several embodiments of the invention described herein, using routine methodology in the art.

Also disclosed herein is a method for obtaining an antibody antigen binding domain specific for CD40 antigen, the method comprising providing by way of addition, deletion, substitution or insertion of one or more amino acids in the amino acid sequence of a VH domain set out herein a VH domain which is an amino acid sequence variant of the VH domain, optionally combining the VH domain thus provided with one or more VL domains, and testing the VH domain or VH/VL combination or combinations to identify a specific binding member or an antibody antigen binding domain specific for CD40 and optionally with one or more desired properties. The VL domains may have an amino acid sequence which is substantially as set out herein. An analogous method may be employed in which one or more sequence variants of a VL domain disclosed herein are combined with one or more VH domains.

An epitope that "specifically binds" or "preferentially binds" (used interchangeably herein) to an antibody or a polypeptide is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to a CD40 epitope is an antibody that binds one CD40 epitope with greater affinity, avidity, more readily, and/or with greater duration than it binds to other CD40 epitopes or non-CD40 epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

Immunological binding generally refers to the non-covalent interactions of the type which occur between an immunoglobulin molecule and an antigen for which the immunoglobulin is specific, for example by way of illustration and not limitation, as a result of electrostatic, ionic, hydrophilic and/or hydrophobic attractions or repulsion, steric forces, hydrogen bonding, van der Waals forces, and other interactions. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" ($K_{on}$) and the "off rate constant" ($K_{off}$) can be determined by calculation of the concentrations and the actual rates of association and dissociation. The ratio of $K_{off}/K_{on}$ enables cancellation of all parameters not related to affinity, and is thus equal to the dissociation constant $K_d$. See, generally, Davies et al. (1990) *Annual Rev. Biochem.* 59:439-473.

In certain embodiments, the anti-CD40 antibodies described herein have an affinity of about 100, 150, 155, 160, 170, 175, 180, 185, 190, 191, 192, 193, 194, 195, 196, 197, 198 or 199 picomolar, and in some embodiments, the antibodies may have even higher affinity for CD40.

The term "immunologically active", with reference to an epitope being or "remaining immunologically active", refers to the ability of an antibody (e.g., anti-CD40 antibody) to bind to the epitope under different conditions, for example, after the epitope has been subjected to reducing and denaturing conditions.

An antibody or antigen-binding fragment thereof according to certain preferred embodiments of the present application may be one that competes for binding to CD40 with any antibody described herein which both (i) specifically binds to the antigen and (ii) comprises a VH and/or VL domain disclosed herein, or comprises a VH CDR3 disclosed herein, or a variant of any of these. Competition between antibodies may be assayed easily in vitro, for example using ELISA and/or by tagging a specific reporter molecule to one antibody which can be detected in the presence of other untagged antibodies, to enable identification of specific antibodies which bind the same epitope or an overlapping epitope. Thus, there is provided herein a specific antibody or antigen-binding fragment thereof, comprising a human antibody antigen-binding site which competes with an antibody described herein that binds to CD40.

In this regard, as used herein, the terms "competes with", "inhibits binding" and "blocks binding" (e.g., referring to inhibition/blocking of binding of CD40L to CD40 or referring to inhibition/blocking of binding of an anti-CD40 antibody to CD40) are used interchangeably and encompass both partial and complete inhibition/blocking. Inhibition and blocking are also intended to include any measurable decrease in the binding of CD40L to CD40 when in contact with an anti-CD40 antibody as disclosed herein as compared to the ligand not in contact with an anti-CD40 antibody, e.g., the blocking of CD40L to CD40 by at least about 10%, 20%, 30%, 40%, 50%, 60%, 65%, 70%, 75%, 80%, 85%, 90%, 91%, 92%, 93%, 94%, 95%, 96%, 97%, 98%, 99%, or 100%.

The constant regions of immunoglobulins show less sequence diversity than the variable regions, and are responsible for binding a number of natural proteins to elicit important biochemical events. In humans there are five different classes of antibodies including IgA (which includes subclasses IgA1 and IgA2), IgD, IgE, IgG (which includes subclasses IgG1, IgG2, IgG3, and IgG4), and IgM. The distinguishing features between these antibody classes are their constant regions, although subtler differences may exist in the V region.

The Fc region of an antibody interacts with a number of Fc receptors and ligands, imparting an array of important functional capabilities referred to as effector functions. For IgG the Fc region comprises Ig domains CH2 and CH3 and the N-terminal hinge leading into CH2. An important family of Fc receptors for the IgG class are the Fc gamma receptors (FcγRs). These receptors mediate communication between antibodies and the cellular arm of the immune system (Raghavan et al., 1996, Annu Rev Cell Dev Biol 12:181-220; Ravetch et al., 2001, Annu Rev Immunol 19:275-290). In humans this protein family includes FcγRI (CD64), including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158) and FcγRIIIb (including allotypes FcγRIIIb-NA1 and FcγRIIIb-NA2) (Jefferis et al., 2002, Immunol Lett 82:57-65). These receptors typically have an extracellular domain that mediates binding to Fc, a membrane spanning region, and an intracellular domain that may mediate some signaling event within the cell. These receptors are expressed in a variety of immune cells including monocytes, macrophages, neutrophils, dendritic cells, eosinophils, mast cells, platelets, B cells, large granular lymphocytes, Langerhans' cells, natural killer (NK) cells, and T cells. Formation of the Fc/FcγR complex recruits these effector cells to sites of bound antigen, typically resulting in signaling events within the cells and important subsequent immune responses such as release of inflammation mediators, B cell activation, endocytosis, phagocytosis, and cytotoxic attack.

The ability to mediate cytotoxic and phagocytic effector functions is a potential mechanism by which antibodies destroy targeted cells. The cell-mediated reaction wherein nonspecific cytotoxic cells that express FcγRs recognize bound antibody on a target cell and subsequently cause lysis of the target cell is referred to as antibody dependent cell-mediated cytotoxicity (ADCC) (Raghavan et al., 1996, Annu Rev Cell Dev Biol 12:181-220; Ghetie et al., 2000, Annu Rev Immunol 18:739-766; Ravetch et al., 2001, Annu Rev Immunol 19:275-290). The cell-mediated reaction wherein nonspecific cytotoxic cells that express FcγRs recognize bound antibody on a target cell and subsequently cause phagocytosis of the target cell is referred to as antibody dependent cell-mediated phagocytosis (ADCP). All FcγRs bind the same region on Fc, at the N-terminal end of the Cg2 (CH2) domain and the preceding hinge. This interaction is well characterized structurally (Sondermann et al., 2001, J Mol Biol 309:737-749), and several structures of the human Fc bound to the extracellular domain of human FcγRIIIb have been solved (pdb accession code 1E4K) (Sondermann et al., 2000, Nature 406:267-273.) (pdb accession codes 111 S and 1IIX)(Radaev et al., 2001, J Biol Chem 276:16469-16477.)

The different IgG subclasses have different affinities for the FcγRs, with IgG1 and IgG3 typically binding substantially better to the receptors than IgG2 and IgG4 (Jefferis et al., 2002, Immunol Lett 82:57-65). All FcγRs bind the same region on IgG Fc, yet with different affinities: the high affinity binder FcγRI has a Kd for IgG1 of $10^{-8}$ $M^{-1}$, whereas the low affinity receptors FcγRII and FcγRIII generally bind at $10^{-6}$ and $10^{-5}$ respectively. The extracellular domains of FcγRIIIa and FcγRIIIb are 96% identical; however FcγRIIIb does not have a intracellular signaling domain. Furthermore, whereas FcγRI, FcγRIIa/c, and FcγRIIIa are positive regulators of immune complex-triggered activation, characterized by having an intracellular domain that has an immunoreceptor tyrosine-based activation motif (ITAM), FcγRIIb has an immunoreceptor tyrosine-based inhibition motif (ITIM) and is therefore inhibitory. Thus the former are referred to as activation receptors, and FcγRIIb is referred to as an inhibitory receptor. The receptors also differ in expression pattern and levels on different immune cells. Yet another level of complexity is the existence of a number of FcγR polymorphisms in the human proteome. A particularly relevant polymorphism with clinical significance is V158/F158 FcγRIIIa. Human IgG1 binds with greater affinity to the V158 allotype than to the F158 allotype. This difference in affinity, and presumably its effect on ADCC and/or ADCP, has been shown to be a significant determinant of the efficacy of the anti-CD20 antibody rituximab (Rituxan®, a registered trademark of IDEC Pharmaceuticals Corporation). Patients with the V158 allotype respond favorably to rituximab treatment; however, patients with the lower affinity F158 allotype respond poorly (Cartron et al., 2002, Blood 99:754-758). Approximately 10-20% of humans are V158/V158 homozygous, 45% are V158/F158 heterozygous, and 35-45% of humans are F158/F158 homozygous (Lehrnbecher et al., 1999, Blood 94:4220-4232; Cartron et al., 2002, Blood 99:754-758). Thus 80-90% of humans are poor responders, that is, they have at least one allele of the F158 FcγRIIIa.

The Fc region is also involved in activation of the complement cascade. In the classical complement pathway, C1 binds with its C1q subunits to Fc fragments of IgG or IgM, which has formed a complex with antigen(s). In certain embodiments of the invention, modifications to the Fc region comprise modifications that alter (either enhance or decrease) the ability of a CD40-specific antibody as described herein to activate the complement system (see e.g., U.S. Pat. No. 7,740,847). To assess complement activation, a complement-dependent cytotoxicity (CDC) assay may be performed (See, e.g., Gazzano-Santoro et al., J. Immunol. Methods, 202:163 (1996)).

Thus in certain embodiments, the present invention provides anti-CD40 antibodies having a modified Fc region with altered functional properties, such as reduced or enhanced CDC, ADCC, or ADCP activity, or enhanced binding affinity for a specific FcγR or increased serum half-life. Other modified Fc regions contemplated herein are described, for example, in issued U.S. Pat. Nos. 7,317,091; 7,657,380; 7,662,925; 6,538,124; 6,528,624; 7,297,775; 7,364,731; Published U.S. Applications US2009092599; US20080131435; US20080138344; and published International Applications WO2006/105338; WO2004/063351; WO2006/088494; WO2007/024249.

In one embodiment, one or more substitutions in the Fc may increase the binding affinity to FcγRIIB, enhance cross-linking of CD40 molecules and lead to stronger CD40 activation by an anti-CD40 antibody. In one embodiment, the present invention provides anti-CD40 antibodies having a modified Fc region at position 267 (EU numbering; see e.g., Edelman, G. M. et al., 1969 Proc. Natl. Acad. USA, 63, 78-85; see also the ImMunoGeneTics (IMGT) database website at imgt.org/IMGTScientificChart/Numbering). In one embodiment, an anti-CD40 antibody herein comprises a modified Fc comprising a S267E substitution (Li Fu, Ravetch J V. 2011 Science 333:1030; see also J. Immunol. 2011, 187:1754-1763; mAbs 2010, 2:181-189). The amino acid sequence of a heavy chain constant region comprising an illustrative modified Fc is set forth in SEQ ID NO:195.

Thus, in certain embodiments, antibody variable domains with the desired binding specificities are fused to immunoglobulin constant domain sequences. In certain embodiments, the fusion is with an Ig heavy chain constant domain, comprising at least part of the hinge, $C_H2$, and $C_H3$ regions. It is preferred to have the first heavy-chain constant region ($C_H1$) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant effect on the yield of the desired chain combination.

Antibodies of the present invention (and antigen-binding fragments and variants thereof) may also be modified to include an epitope tag or label, e.g., for use in purification or diagnostic applications. There are many linking groups known in the art for making antibody conjugates, including, for example, those disclosed in U.S. Pat. No. 5,208,020 or EP Patent 0 425 235 B1, and Chari et al., Cancer Research 52: 127-131 (1992). The linking groups include disulfide groups, thioether groups, acid labile groups, photolabile groups, peptidase labile groups, or esterase labile groups, as disclosed in the above-identified patents, disulfide and thio-ether groups being preferred.

In another contemplated embodiment, a CD40-specific antibody as described herein may be conjugated or operably linked to another therapeutic compound, referred to herein as a conjugate. The conjugate may be a cytotoxic agent, a chemotherapeutic agent, a cytokine, an anti-angiogenic agent, a tyrosine kinase inhibitor, a toxin, a radioisotope, or other therapeutically active agent. Chemotherapeutic agents, cytokines, anti-angiogenic agents, tyrosine kinase inhibitors, and other therapeutic agents have been described above, and all of these aforementioned therapeutic agents may find use as antibody conjugates.

In an alternate embodiment, the antibody is conjugated or operably linked to a toxin, including but not limited to small molecule toxins and enzymatically active toxins of bacterial, fungal, plant or animal origin, including fragments and/or variants thereof. Small molecule toxins include but are not limited to saporin (Kuroda K, et al., The Prostate 70:1286-1294 (2010); Lip, W L. et al., 2007 Molecular Pharmaceutics 4:241-251; Quadros E V., et al., 2010 Mol Cancer Ther; 9(11); 3033-40; Polito L., et al. 2009 British Journal of Haematology, 147, 710-718), calicheamicin, maytansine (U.S. Pat. No. 5,208,020), trichothene, and CC1065. Toxins include but are not limited to RNase, gelonin, enediynes, ricin, abrin, diptheria toxin, cholera toxin, gelonin, *Pseudomonas* exotoxin (PE40), *Shigella* toxin, *Clostridium perfringens* toxin, and pokeweed antiviral protein.

In one embodiment, an antibody or antigen-binding fragment thereof of the disclosure is conjugated to one or more maytansinoid molecules. Maytansinoids are mitototic inhibitors that act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533. Immunoconjugates containing maytansinoids and their therapeutic use are disclosed, for example, in U.S. Pat. Nos. 5,208,020, 5,416,064 and European Patent EP 0 425 235 B1. Liu et al., Proc. Natl. Acad. Sci. USA 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay.

Antibody-maytansinoid conjugates are prepared by chemically linking an antibody to a maytansinoid molecule without significantly diminishing the biological activity of either the antibody or the maytansinoid molecule. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

Another conjugate of interest comprises an antibody conjugated to one or more calicheamicin molecules. The calicheamicin family of antibiotics is capable of producing double-stranded DNA breaks at sub-picomolar concentrations. Structural analogues of calicheamicin that may also be used (Hinman et al., 1993, Cancer Research 53:3336-3342; Lode et al., 1998, Cancer Research 58:2925-2928) (U.S. Pat. No. 5,714,586; U.S. Pat. No. 5,712,374; U.S. Pat. No. 5,264,586; U.S. Pat. No. 5,773,001). Dolastatin 10 analogs such as auristatin E (AE) and monomethylauristatin E (MMAE) may find use as conjugates for the presently disclosed antibodies, or variants thereof (Doronina et al., 2003, Nat Biotechnol 21(7):778-84; Francisco et al., 2003 Blood 102(4):1458-65). Useful enzymatically active toxins include but are not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecenes. See, for example, PCT WO 93/21232. The present disclosure further contemplates embodiments in which a conjugate or fusion is formed between a CD40-specific antibody as described herein and a compound with nucleolytic activity, for example a ribonuclease or DNA endonuclease such as a deoxyribonuclease (DNase).

In an alternate embodiment, a herein-disclosed antibody may be conjugated or operably linked to a radioisotope to form a radioconjugate. A variety of radioactive isotopes are available for the production of radioconjugate antibodies. Examples include, but are not limited to $^{90}Y$, $^{123}I$, $^{125}I$, $^{131}I$, $^{186}Re$, $^{188}Re$, $^{211}At$, and $^{212}Bi$.

Antibodies described herein may in certain other embodiments be conjugated to a therapeutic moiety such as a cytotoxin (e.g., a cytostatic or cytocidal agent), a therapeutic agent or a radioactive element (e.g., alpha-emitters, gamma-emitters, etc.). Cytotoxins or cytotoxic agents include any agent that is detrimental to cells. Examples include paclitaxel/paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. One preferred exemplary cytotoxin is saporin (available from Advanced Targeting Systems, San Diego, Calif.). Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC), and antimitotic agents (e.g., vincristine and vinblastine).

Moreover, a CD40-specific antibody (including a functional fragment thereof as provided herein such as an antigen-binding fragment) may in certain embodiments be conjugated to therapeutic moieties such as a radioactive materials or macrocyclic chelators useful for conjugating radiometal ions. In certain embodiments, the macrocyclic chelator is 1,4,7,10-tetraazacyclododecane-N,N',N'',N'''tetraacetic acid (DOTA) which can be attached to the antibody via a linker molecule. Such linker molecules are commonly known in the art and described in Denardo et al., 1998, Clin Cancer Res. 4:2483-90; Peterson et al., 1999, Bioconjug. Chem. 10:553; and Zimmerman et al., 1999, Nucl. Med. Biol. 26:943-50.

In yet another embodiment, an antibody may be conjugated to a "receptor" (such as streptavidin) for utilization in tumor pretargeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionucleotide). In an alternate embodiment, the antibody is conjugated or operably linked to an enzyme in order to employ Antibody Dependent Enzyme Mediated Prodrug Therapy (ADEPT). ADEPT may be used by conjugating or operably linking the antibody to a prodrug-activating enzyme that converts a prodrug (e.g. a peptidyl chemotherapeutic agent, see PCT WO 81/01145) to an active anti-cancer drug. See, for example, PCT WO 88/07378 and U.S. Pat. No. 4,975,278. The enzyme component of the immunoconjugate useful for ADEPT includes any enzyme capable of acting on a prodrug in such a way so as to convert it into its more active, cytotoxic form. Enzymes that are useful in the method of these and related embodiments include but are not limited to alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as *serratia* protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuramimidase useful for converting glycosylated prodrugs into free drugs; beta-lactamase useful for converting drugs derivatized with α-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", may be used to convert prodrugs into free active drugs (see, for example, Massey, 1987, Nature 328: 457-458). Antibody-abzyme conjugates can be prepared for delivery of the abzyme to a tumor cell population.

Immunoconjugates may be made using a variety of bifunctional protein coupling agents such as N-succinimidyl-3-(2-pyridyldithio)propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particular coupling agents include N-succinimidyl-3-(2-pyridyldithio) propionate (SPDP) (Carlsson et al., Biochem. J. 173:723-737 [1978]) and N-succinimidyl-4-(2-pyridylthio)pentanoate (SPP) to provide for a disulfide linkage. The linker may be a "cleavable linker" facilitating release of one or more cleavable components. For example, an acid-labile linker may be used (Cancer Research 52: 127-131 (1992); U.S. Pat. No. 5,208,020).

Other modifications of the antibodies (and polypeptides) of the invention are also contemplated herein. For example, the antibody may be linked to one of a variety of nonproteinaceous polymers, e.g., polyethylene glycol, polypropylene glycol, polyoxyalkylenes, or copolymers of polyethylene glycol and polypropylene glycol. The antibody also may be entrapped in microcapsules prepared, for example, by coacervation techniques or by interfacial polymerization (for example, hydroxymethylcellulose or gelatin-microcapsules and poly-(methylmethacylate)microcapsules, respectively), in colloidal drug delivery systems (for example, liposomes, albumin microspheres, microemulsions, nanoparticles and nanocapsules), or in macroemulsions. Such techniques are disclosed in Remington's Pharmaceutical Sciences, 16th edition, Oslo, A., Ed., (1980).

"Carriers" as used herein include pharmaceutically acceptable carriers, excipients, or stabilizers that are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as polysorbate 20 (TWEEN™) polyethylene glycol (PEG), and poloxamers (PLURONICS™), and the like.

As noted elsewhere herein, the antibodies of the present disclosure induce CD40 signaling in tumor cells, activate dendritic cells and immune surveillance, activate antibody dependent cellular cytotoxicity (ADCC) against tumor cells, block binding of CD40 to CD40L; have CD40 agonistic activity; activate antigen presenting cells; stimulate cytokine release from antigen presenting cells; induce tumor cell apoptosis; inhibit tumor cell proliferation; kill tumor cells via induction of effector functions including but not limited to ADCC, CDC and ADCP; stimulate anti-tumor T cell responses; reduce established tumors; and inhibit rituximab-resistant tumors. The antibodies described herein may have or induce a combination of any one or more of these attributes or activities. The desired functional properties of anti-CD40 antibodies may be assessed using a variety of methods known to the skilled person, such as affinity/binding assays (for example, surface plasmon resonance, competitive inhibition assays); cytotoxicity assays, cell viability assays, cell proliferation, activation or differentiation assays, ADCC and CDC assays, other cellular activity resulting from CD40 cell signaling events (e.g., STAT3 phosphorylation, production of cytokines including IL-1, IL-6, IL-8, IL-10, IL-12, TNF-Alpha, and MIP1Alpha), and cancer cell and/or tumor growth inhibition using in vitro or in vivo models. Other assays may test the ability of antibodies described herein to block normal CD40L binding to CD40 or CD40-mediated responses, such as cell signaling, cell activation (e.g., immune cell activation, proliferation; antigen presenting cell activation (e.g., dendritic cells, B cells, macrophages) and maturation assays), immune responses (including cell mediated and humoral responses), etc. The antibodies described herein may also be tested for effects on CD40 internalization, in vitro and in vivo efficacy, etc. Such assays may be performed using well-established protocols known to the skilled person (see e.g., Current Protocols in Molecular Biology (Greene Publ. Assoc. Inc. & John Wiley & Sons, Inc., NY, N.Y.); Current Protocols in Immunology (Edited by: John E. Coligan, Ada M. Kruisbeek, David H. Margulies, Ethan M. Shevach, Warren Strober 2001 John Wiley & Sons, NY, N.Y.); or commercially available kits.

The present invention further provides in certain embodiments an isolated nucleic acid encoding an antibody or antigen-binding fragment thereof as described herein, for instance, a nucleic acid which codes for a CDR or VH or VL domain as described herein. Nucleic acids include DNA and RNA. These and related embodiments may include polynucleotides encoding antibodies that bind CD40 as described herein. The term "isolated polynucleotide" as used herein shall mean a polynucleotide of genomic, cDNA, or synthetic origin or some combination thereof, which by virtue of its origin the isolated polynucleotide (1) is not associated with all or a portion of a polynucleotide in which the isolated polynucleotide is found in nature, (2) is linked to a polynucleotide to which it is not linked in nature, or (3) does not occur in nature as part of a larger sequence.

The term "operably linked" means that the components to which the term is applied are in a relationship that allows them to carry out their inherent functions under suitable conditions. For example, a transcription control sequence "operably linked" to a protein coding sequence is ligated thereto so that expression of the protein coding sequence is achieved under conditions compatible with the transcriptional activity of the control sequences.

The term "control sequence" as used herein refers to polynucleotide sequences that can affect expression, processing or intracellular localization of coding sequences to which they are ligated or operably linked. The nature of such control sequences may depend upon the host organism. In particular embodiments, transcription control sequences for prokaryotes may include a promoter, ribosomal binding site, and transcription termination sequence. In other particular embodiments, transcription control sequences for eukaryotes may include promoters comprising one or a plurality of recognition sites for transcription factors, transcription enhancer sequences, transcription termination sequences and polyadenylation sequences. In certain embodiments, "control sequences" can include leader sequences and/or fusion partner sequences.

The term "polynucleotide" as referred to herein means single-stranded or double-stranded nucleic acid polymers. In certain embodiments, the nucleotides comprising the polynucleotide can be ribonucleotides or deoxyribonucleotides or a modified form of either type of nucleotide. Said modifications include base modifications such as bromouridine, ribose modifications such as arabinoside and 2',3'-dideoxyribose and internucleotide linkage modifications such as phosphorothioate, phosphorodithioate, phosphoroselenoate, phosphorodiselenoate, phosphoroanilothioate, phoshoraniladate and phosphoroamidate. The term "polynucleotide" specifically includes single and double stranded forms of DNA.

The term "naturally occurring nucleotides" includes deoxyribonucleotides and ribonucleotides. The term "modified nucleotides" includes nucleotides with modified or substituted sugar groups and the like. The term "oligonucleotide linkages" includes oligonucleotide linkages such as phosphorothioate, phosphorodithioate, phosphoroselenoate, phosphorodiselenoate, phosphoroanilothioate, phoshoraniladate, phosphoroamidate, and the like. See, e.g., LaPlanche et al., 1986, Nucl. Acids Res., 14:9081; Stec et al., 1984, J. Am. Chem. Soc., 106:6077; Stein et al., 1988, Nucl. Acids Res., 16:3209; Zon et al., 1991, Anti-Cancer Drug Design, 6:539; Zon et al., 1991, OLIGONUCLEOTIDES AND ANALOGUES: A PRACTICAL APPROACH, pp. 87-108 (F. Eckstein, Ed.), Oxford University Press, Oxford England; Stec et al., U.S. Pat. No. 5,151,510; Uhlmann and Peyman, 1990, Chemical Reviews, 90:543, the disclosures of which are hereby incorporated by reference for any purpose. An oligonucleotide can include a detectable label to enable detection of the oligonucleotide or hybridization thereof.

The term "vector" is used to refer to any molecule (e.g., nucleic acid, plasmid, or virus) used to transfer coding information to a host cell. The term "expression vector" refers to a vector that is suitable for transformation of a host cell and contains nucleic acid sequences that direct and/or control expression of inserted heterologous nucleic acid sequences. Expression includes, but is not limited to, processes such as transcription, translation, and RNA splicing, if introns are present.

As will be understood by those skilled in the art, polynucleotides may include genomic sequences, extra-genomic and plasmid-encoded sequences and smaller engineered gene segments that express, or may be adapted to express, proteins, polypeptides, peptides and the like. Such segments may be naturally isolated, or modified synthetically by the skilled person.

As will be also recognized by the skilled artisan, polynucleotides may be single-stranded (coding or antisense) or double-stranded, and may be DNA (genomic, cDNA or synthetic) or RNA molecules. RNA molecules may include HnRNA molecules, which contain introns and correspond to a DNA molecule in a one-to-one manner, and mRNA molecules, which do not contain introns. Additional coding or non-coding sequences may, but need not, be present within a polynucleotide according to the present disclosure, and a polynucleotide may, but need not, be linked to other molecules and/or support materials. Polynucleotides may comprise a native sequence or may comprise a sequence that encodes a variant or derivative of such a sequence.

Therefore, according to these and related embodiments, the present disclosure also provides polynucleotides encoding the anti-CD40 antibodies described herein. In certain embodiments, polynucleotides are provided that comprise some or all of a polynucleotide sequence encoding an antibody as described herein and complements of such polynucleotides.

In other related embodiments, polynucleotide variants may have substantial identity to a polynucleotide sequence encoding an anti-CD40 antibody described herein. For example, a polynucleotide may be a polynucleotide comprising at least 70% sequence identity, preferably at least 75%, 80%, 85%, 90%, 95%, 96%, 97%, 98%, or 99% or higher, sequence identity compared to a reference polynucleotide sequence such as a sequence encoding an antibody described herein, using the methods described herein, (e.g., BLAST analysis using standard parameters, as described below). One skilled in this art will recognize that these values can be appropriately adjusted to determine corresponding identity of proteins encoded by two nucleotide sequences by taking into account codon degeneracy, amino acid similarity, reading frame positioning and the like.

Typically, polynucleotide variants will contain one or more substitutions, additions, deletions and/or insertions, preferably such that the binding affinity of the antibody encoded by the variant polynucleotide is not substantially diminished relative to an antibody encoded by a polynucleotide sequence specifically set forth herein.

In certain other related embodiments, polynucleotide fragments may comprise or consist essentially of various lengths of contiguous stretches of sequence identical to or complementary to a sequence encoding an antibody as described herein. For example, polynucleotides are provided that comprise or consist essentially of at least about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, 100, 110, 120, 130, 140, 150, 200, 300, 400, 500 or 1000 or more contiguous nucleotides of a sequences the encodes an antibody, or antigen-binding fragment thereof, disclosed herein as well as all intermediate lengths there between. It will be readily understood that "intermediate lengths", in this context, means any length between the quoted values, such as 50, 51, 52, 53, etc.; 100, 101, 102, 103, etc.; 150, 151, 152, 153, etc.; including all integers through 200-500; 500-1,000, and the like. A polynucleotide sequence as described here may be extended at one or both ends by additional nucleotides not found in the native sequence. This additional sequence may consist of 1, 2, 3, 4, 5, 6, 7, 8, 9, 10, 11, 12, 13, 14, 15, 16, 17, 18, 19, or 20 nucleotides at either end of a polynucleotide encoding an antibody described herein or at both ends of a polynucleotide encoding an antibody described herein.

In another embodiment, polynucleotides are provided that are capable of hybridizing under moderate to high stringency conditions to a polynucleotide sequence encoding an antibody, or antigen-binding fragment thereof, provided herein, or a fragment thereof, or a complementary sequence thereof. Hybridization techniques are well known in the art of molecular biology. For purposes of illustration, suitable moderately stringent conditions for testing the hybridization of a polynucleotide as provided herein with other polynucleotides include prewashing in a solution of 5×SSC, 0.5% SDS, 1.0 mM EDTA (pH 8.0); hybridizing at 50° C.-60° C., 5×SSC, overnight; followed by washing twice at 65° C. for 20 minutes with each of 2×, 0.5× and 0.2×SSC containing 0.1% SDS. One skilled in the art will understand that the stringency of hybridization can be readily manipulated, such as by altering the salt content of the hybridization solution and/or the temperature at which the hybridization is performed. For example, in another embodiment, suitable highly stringent hybridization conditions include those described above, with the exception that the temperature of hybridization is increased, e.g., to 60° C.-65° C. or 65° C.-70° C.

In certain embodiments, the polynucleotides described above, e.g., polynucleotide variants, fragments and hybridizing sequences, encode antibodies that bind CD40, or antigen-binding fragments thereof. In other embodiments, such polynucleotides encode antibodies or antigen-binding fragments, or CDRs thereof, that bind to CD40 at least about 50%, at least about 70%, and in certain embodiments, at least about 90% as well as an antibody sequence specifically set forth herein. In further embodiments, such polynucleotides encode antibodies or antigen-binding fragments, or CDRs thereof, that bind to CD40 with greater affinity than the antibodies set forth herein, for example, that bind quantitatively at least about 105%, 106%, 107%, 108%, 109%, or 110% as well as an antibody sequence specifically set forth herein.

As described elsewhere herein, determination of the three-dimensional structures of representative polypeptides (e.g., variant CD40-specific antibodies as provided herein, for instance, an antibody protein having an antigen-binding fragment as provided herein) may be made through routine methodologies such that substitution, addition, deletion or insertion of one or more amino acids with selected natural or non-natural amino acids can be virtually modeled for purposes of determining whether a so derived structural variant retains the space-filling properties of presently disclosed species. A variety of computer programs are known to the skilled artisan for determining appropriate amino acid substitutions (or appropriate polynucleotides encoding the amino acid sequence) within an antibody such that, for example, affinity is maintained or better affinity is achieved.

The polynucleotides described herein, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, illustrative polynucleotide segments with total lengths of about 10,000, about 5000, about 3000, about 2,000, about 1,000, about 500, about 200, about 100, about 50 base pairs in length, and the like, (including all intermediate lengths) are contemplated to be useful.

When comparing polynucleotide sequences, two sequences are said to be "identical" if the sequence of nucleotides in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign™ program in the Lasergene® suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) *Atlas of Protein Sequence and Structure*, National Biomedical Research Foundation, Washington D.C. Vol. 5, Suppl. 3, pp. 345-358; Hein J., *Unified Approach to Alignment and Phylogenes*, pp. 626-645 (1990); *Methods in Enzymology* vol. 183, Academic Press, Inc., San Diego, Calif.; Higgins, D. G. and Sharp, P. M., *CABIOS* 5:151-153 (1989); Myers, E. W. and Muller W., *CABIOS* 4:11-17 (1988); Robinson, E. D., *Comb. Theor* 11:105 (1971); Santou, N. Nes, M., *Mol. Biol. Evol.* 4:406-425 (1987); Sneath, P. H. A. and Sokal, R. R., *Numerical Taxonomy—the Principles and Practice of Numerical Taxonomy*, Freeman Press, San Francisco, Calif. (1973); Wilbur, W. J. and Lipman, D. J., *Proc. Natl. Acad., Sci. USA* 80:726-730 (1983).

Alternatively, optimal alignment of sequences for comparison may be conducted by the local identity algorithm of Smith and Waterman, *Add. APL. Math* 2:482 (1981), by the identity alignment algorithm of Needleman and Wunsch, *J. Mol. Biol.* 48:443 (1970), by the search for similarity methods of Pearson and Lipman, *Proc. Natl. Acad. Sci. USA* 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al., *Nucl. Acids Res.* 25:3389-3402 (1977), and Altschul et al., *J. Mol. Biol.* 215:403-410 (1990), respectively. BLAST and BLAST 2.0 can be used, for example with the parameters described herein, to determine percent sequence identity among two or more the polynucleotides. Software for performing BLAST analyses is publicly available through the National Center for Biotechnology Information. In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a word length (W) of 11, and expectation (E) of 10, and the BLOSUM62 scoring matrix (see Henikoff and Henikoff, *Proc. Natl. Acad. Sci. USA* 89:10915 (1989)) alignments, (B) of 50, expectation (E) of 10, M=5, N=−4 and a comparison of both strands.

In certain embodiments, the "percentage of sequence identity" is determined by comparing two optimally aligned sequences over a window of comparison of at least 20 positions, wherein the portion of the polynucleotide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases occurs in both sequences to yield the number of matched positions, dividing the number of matched positions by the total number of positions in the reference sequence (i.e., the window size) and multiplying the results by 100 to yield the percentage of sequence identity.

It will be appreciated by those of ordinary skill in the art that, as a result of the degeneracy of the genetic code, there are many nucleotide sequences that encode an antibody as described herein. Some of these polynucleotides bear minimal sequence identity to the nucleotide sequence of the native or original polynucleotide sequence that encodes antibodies that bind to CD40. Nonetheless, polynucleotides that vary due to differences in codon usage are expressly contemplated by the present disclosure. In certain embodiments, sequences that have been codon-optimized for mammalian expression are specifically contemplated.

Therefore, in another embodiment of the invention, a mutagenesis approach, such as site-specific mutagenesis, may be employed for the preparation of variants and/or derivatives of the antibodies described herein. By this approach, specific modifications in a polypeptide sequence can be made through mutagenesis of the underlying polynucleotides that encode them. These techniques provides a straightforward approach to prepare and test sequence variants, for example, incorporating one or more of the foregoing considerations, by introducing one or more nucleotide sequence changes into the polynucleotide.

Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Mutations may be employed in a selected polynucleotide sequence to improve, alter, decrease, modify, or otherwise change the properties of the polynucleotide itself, and/or alter the properties, activity, composition, stability, or primary sequence of the encoded polypeptide.

In certain embodiments, the inventors contemplate the mutagenesis of the polynucleotide sequences that encode an antibody disclosed herein, or an antigen-binding fragment thereof, to alter one or more properties of the encoded polypeptide, such as the binding affinity of the antibody or the antigen-binding fragment thereof, or the function of a particular Fc region, or the affinity of the Fc region for a particular FcγR. The techniques of site-specific mutagenesis are well-known in the art, and are widely used to create variants of both polypeptides and polynucleotides. For example, site-specific mutagenesis is often used to alter a specific portion of a DNA molecule. In such embodiments, a primer comprising typically about 14 to about 25 nucleotides or so in length is employed, with about 5 to about 10 residues on both sides of the junction of the sequence being altered.

As will be appreciated by those of skill in the art, site-specific mutagenesis techniques have often employed a phage vector that exists in both a single stranded and double stranded form. Typical vectors useful in site-directed mutagenesis include vectors such as the M13 phage. These phage are readily commercially-available and their use is generally well-known to those skilled in the art. Double-stranded plasmids are also routinely employed in site directed mutagenesis that eliminates the step of transferring the gene of interest from a plasmid to a phage.

In general, site-directed mutagenesis in accordance herewith is performed by first obtaining a single-stranded vector or melting apart of two strands of a double-stranded vector that includes within its sequence a DNA sequence that encodes the desired peptide. An oligonucleotide primer bearing the desired mutated sequence is prepared, generally synthetically. This primer is then annealed with the single-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected which include recombinant vectors bearing the mutated sequence arrangement.

The preparation of sequence variants of the selected peptide-encoding DNA segments using site-directed mutagenesis provides a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants. Specific details regarding these methods and protocols are found in the teachings of Maloy et al., 1994; Segal, 1976; Prokop and Bajpai, 1991; Kuby, 1994; and Maniatis et al., 1982, each incorporated herein by reference, for that purpose.

As used herein, the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" is intended to refer to a process that involves the template-dependent extension of a primer molecule. The term template dependent process refers to nucleic acid synthesis of an RNA or a DNA molecule wherein the sequence of the newly synthesized strand of nucleic acid is dictated by the well-known rules of complementary base pairing (see, for example, Watson, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, specifically incorporated herein by reference in its entirety.

In another approach for the production of polypeptide variants, recursive sequence recombination, as described in U.S. Pat. No. 5,837,458, may be employed. In this approach, iterative cycles of recombination and screening or selection are performed to "evolve" individual polynucleotide variants having, for example, increased binding affinity. Certain embodiments also provide constructs in the form of plasmids, vectors, transcription or expression cassettes which comprise at least one polynucleotide as described herein.

In many embodiments, the nucleic acids encoding a subject monoclonal antibody are introduced directly into a host cell, and the cell incubated under conditions sufficient to induce expression of the encoded antibody. The antibodies of this disclosure are prepared using standard techniques well known to those of skill in the art in combination with the polypeptide and nucleic acid sequences provided herein. The polypeptide sequences may be used to determine appropriate nucleic acid sequences encoding the particular antibody disclosed thereby. The nucleic acid sequence may be optimized to reflect particular codon "preferences" for various expression systems according to standard methods well known to those of skill in the art.

According to certain related embodiments there is provided a recombinant host cell which comprises one or more constructs as described herein; a nucleic acid encoding any antibody, CDR, VH or VL domain, or antigen-binding fragment thereof; and a method of production of the encoded product, which method comprises expression from encoding nucleic acid therefor. Expression may conveniently be achieved by culturing under appropriate conditions recombinant host cells containing the nucleic acid. Following production by expression, an antibody or antigen-binding fragment thereof, may be isolated and/or purified using any suitable technique, and then used as desired.

Antibodies or antigen-binding fragments thereof as provided herein, and encoding nucleic acid molecules and vectors, may be isolated and/or purified, e.g. from their natural environment, in substantially pure or homogeneous form, or, in the case of nucleic acid, free or substantially free of nucleic acid or genes of origin other than the sequence encoding a polypeptide with the desired function. Nucleic acid may comprise DNA or RNA and may be wholly or partially synthetic. Reference to a nucleotide sequence as set out herein encompasses a DNA molecule with the specified sequence, and encompasses a RNA molecule with the specified sequence in which U is substituted for T, unless context requires otherwise.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells, NSO mouse melanoma cells and many others. A common, preferred bacterial host is E. coli.

The expression of antibodies and antigen-binding fragments in prokaryotic cells such as E. coli is well established in the art. For a review, see for example Pluckthun, A. Bio/Technology 9: 545-551 (1991). Expression in eukaryotic cells in culture is also available to those skilled in the art as an option for production of antibodies or antigen-binding fragments thereof, see recent reviews, for example Ref, M. E. (1993) Curr. Opinion Biotech. 4: 573-576; Trill J. J. et al. (1995) Curr. Opinion Biotech 6: 553-560.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g. phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Second Edition, Ausubel et al. eds., John Wiley & Sons, 1992, or subsequent updates thereto.

The term "host cell" is used to refer to a cell into which has been introduced, or which is capable of having introduced into it, a nucleic acid sequence encoding one or more of the herein described antibodies, and which further expresses or is capable of expressing a selected gene of interest, such as a gene encoding any herein described antibody. The term includes the progeny of the parent cell, whether or not the progeny are identical in morphology or in genetic make-up to the original parent, so long as the selected gene is present. Accordingly there is also contemplated a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage. The introduction may be followed by causing or allowing expression from the nucleic acid, e.g. by culturing host cells under conditions for expression of the gene. In one embodiment, the nucleic acid is integrated into the genome (e.g. chromosome) of the host cell. Integration may be promoted by inclusion of sequences which promote recombination with the genome, in accordance—with standard techniques.

The present invention also provides, in certain embodiments, a method which comprises using a construct as stated above in an expression system in order to express a particular polypeptide such as a CD40-specific antibody as described herein. The term "transduction" is used to refer to the transfer of genes from one bacterium to another, usually by a phage. "Transduction" also refers to the acquisition and transfer of eukaryotic cellular sequences by retroviruses. The term "transfection" is used to refer to the uptake of foreign or exogenous DNA by a cell, and a cell has been "transfected" when the exogenous DNA has been introduced inside the cell membrane. A number of transfection techniques are well known in the art and are disclosed herein. See, e.g., Graham et al., 1973, Virology 52:456; Sambrook et al., 2001, MOLECULAR CLONING, A LABORATORY MANUAL, Cold Spring Harbor Laboratories; Davis et al., 1986, BASIC METHODS IN MOLECULAR BIOLOGY, Elsevier; and Chu et al., 1981, Gene 13:197. Such techniques can be used to introduce one or more exogenous DNA moieties into suitable host cells.

The term "transformation" as used herein refers to a change in a cell's genetic characteristics, and a cell has been transformed when it has been modified to contain a new DNA. For example, a cell is transformed where it is genetically modified from its native state. Following transfection or transduction, the transforming DNA may recombine with that of the cell by physically integrating into a chromosome of the cell, or may be maintained transiently as an episomal element without being replicated, or may replicate independently as a plasmid. A cell is considered to have been stably transformed when the DNA is replicated with the division of the cell. The term "naturally occurring" or "native" when used in connection with biological materials such as nucleic acid molecules, polypeptides, host cells, and the like, refers to materials which are found in nature and are not manipulated by a human. Similarly, "non-naturally occurring" or "non-native" as used herein refers to a material that is not found in nature or that has been structurally modified or synthesized by a human.

The terms "polypeptide" "protein" and "peptide" and "glycoprotein" are used interchangeably and mean a polymer of amino acids not limited to any particular length. The term does not exclude modifications such as myristylation, sulfation, glycosylation, phosphorylation and addition or deletion of signal sequences. The terms "polypeptide" or "protein" means one or more chains of amino acids, wherein each chain comprises amino acids covalently linked by peptide bonds, and wherein said polypeptide or protein can comprise a plurality of chains non-covalently and/or covalently linked together by peptide bonds, having the sequence of native proteins, that is, proteins produced by naturally-occurring and specifically non-recombinant cells, or genetically-engineered or recombinant cells, and comprise molecules having the amino acid sequence of the native protein, or molecules having deletions from, additions to, and/or substitutions of one or more amino acids of the native sequence. The terms "polypeptide" and "protein" specifically encompass the antibodies that bind to CD40 of the present disclosure, or sequences that have deletions from, additions to, and/or substitutions of one or more amino acid of an anti-CD40 antibody. Thus, a "polypeptide" or a "protein" can comprise one (termed "a monomer") or a plurality (termed "a multimer") of amino acid chains.

The term "isolated protein" referred to herein means that a subject protein (1) is free of at least some other proteins with which it would typically be found in nature, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is not associated (by covalent or noncovalent interaction) with portions of a protein with which the "isolated protein" is associated in nature, (6) is operably associated (by covalent or noncovalent interaction) with a polypeptide with which it is not associated in nature, or (7) does not occur in nature. Such an isolated protein can be encoded by genomic DNA, cDNA, mRNA or other RNA, of may be of synthetic origin, or any combination thereof. In certain embodiments, the isolated protein is substantially free from proteins or polypeptides or other contaminants that are found in its natural environment that would interfere with its use (therapeutic, diagnostic, prophylactic, research or otherwise).

The term "polypeptide fragment" refers to a polypeptide, which can be monomeric or multimeric, that has an amino-terminal deletion, a carboxyl-terminal deletion, and/or an internal deletion or substitution of a naturally-occurring or recombinantly-produced polypeptide. In certain embodiments, a polypeptide fragment can comprise an amino acid chain at least 5 to about 500 amino acids long. It will be appreciated that in certain embodiments, fragments are at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 150, 200, 250, 300, 350, 400, or 450 amino acids long. Particularly useful polypeptide fragments include functional domains, including antigen-binding domains or fragments of antibodies. In the case of an anti-CD40 antibody, useful fragments include, but are not limited to: a CDR region, especially a CDR3 region of the heavy or light chain; a variable region of a heavy or light chain; a portion of an antibody chain or just its variable region including two CDRs; and the like.

Polypeptides may comprise a signal (or leader) sequence at the N-terminal end of the protein, which co-translationally or post-translationally directs transfer of the protein. Any polypeptide amino acid sequences provided herein that include a signal peptide are also contemplated for any use described herein without such a signal or leader peptide. As would be recognized by the skilled person, the signal peptide is usually cleaved during processing and is not included in the active antibody protein. The polypeptide may also be fused in-frame or conjugated to a linker or other sequence for ease of synthesis, purification or identification of the polypeptide (e.g., poly-His), or to enhance binding of the polypeptide to a solid support.

A peptide linker/spacer sequence may also be employed to separate multiple polypeptide components by a distance sufficient to ensure that each polypeptide folds into its secondary and/or tertiary structures, if desired. Such a peptide linker sequence can be incorporated into a fusion polypeptide using standard techniques well known in the art.

Certain peptide spacer sequences may be chosen, for example, based on: (1) their ability to adopt a flexible extended conformation; (2) their inability to adopt a secondary structure that could interact with functional epitopes on the first and second polypeptides; and/or (3) the lack of hydrophobic or charged residues that might react with the polypeptide functional epitopes.

In one illustrative embodiment, peptide spacer sequences contain, for example, Gly, Asn and Ser residues. Other near neutral amino acids, such as Thr and Ala, may also be included in the spacer sequence.

Other amino acid sequences which may be usefully employed as spacers include those disclosed in Maratea et al., Gene 40:39 46 (1985); Murphy et al., Proc. Natl. Acad. Sci. USA 83:8258 8262 (1986); U.S. Pat. No. 4,935,233 and U.S. Pat. No. 4,751,180.

Other illustrative spacers may include, for example, Glu-Gly-Lys-Ser-Ser-Gly-Ser-Gly-Ser-Glu-Ser-Lys-Val-Asp (SEQ ID NO:203)(Chaudhary et al., 1990, Proc. Natl. Acad. Sci. U.S.A. 87:1066-1070) and Lys-Glu-Ser-Gly-Ser-Val-Ser-Ser-Glu-Gln-Leu-Ala-Gln-Phe-Arg-Ser-Leu-Asp (SEQ ID NO:204)(Bird et al., 1988, Science 242:423-426).

In some embodiments, spacer sequences are not required when the first and second polypeptides have non-essential N-terminal amino acid regions that can be used to separate the functional domains and prevent steric interference. Two coding sequences can be fused directly without any spacer or by using a flexible polylinker composed, for example, of the pentamer Gly-Gly-Gly-Gly-Ser (SEQ ID NO:205) repeated 1 to 3 times. Such a spacer has been used in constructing single chain antibodies (scFv) by being inserted between VH and VL (Bird et al., 1988, Science 242:423-426; Huston et al., 1988, Proc. Natl. Acad. Sci. U.S.A. 85:5979-5883).

A peptide spacer, in certain embodiments, is designed to enable the correct interaction between two beta-sheets forming the variable region of the single chain antibody.

In certain illustrative embodiments, a peptide spacer is between 1 to 5 amino acids, between 5 to 10 amino acids, between 5 to 25 amino acids, between 5 to 50 amino acids, between 10 to 25 amino acids, between 10 to 50 amino acids, between 10 to 100 amino acids, or any intervening range of amino acids.

In other illustrative embodiments, a peptide spacer comprises about 1, 5, 10, 15, 20, 25, 30, 35, 40, 45, 50 or more amino acids in length.

Amino acid sequence modification(s) of the antibodies described herein are contemplated. For example, it may be desirable to improve the binding affinity and/or other biological properties of the antibody. For example, amino acid sequence variants of an antibody may be prepared by introducing appropriate nucleotide changes into a polynucleotide that encodes the antibody, or a chain thereof, or by peptide synthesis. Such modifications include, for example, deletions from, and/or insertions into and/or substitutions of, residues within the amino acid sequences of the antibody. Any combination of deletion, insertion, and substitution may be made to arrive at the final antibody, provided that the final construct possesses the desired characteristics (e.g., high affinity binding to CD40). The amino acid changes also may alter post-translational processes of the antibody, such as changing the number or position of glycosylation sites. Any of the variations and modifications described above for polypeptides of the present invention may be included in antibodies of the present invention.

The present disclosure provides variants of the antibodies disclosed herein. In certain embodiments, such variant antibodies or antigen-binding fragments, or CDRs thereof, bind to CD40 at least about 50%, at least about 70%, and in certain embodiments, at least about 90% as well as an antibody sequence specifically set forth herein. In further embodiments, such variant antibodies or antigen-binding fragments, or CDRs thereof, bind to CD40 with greater affinity than the antibodies set forth herein, for example, that bind quantitatively at least about 105%, 106%, 107%, 108%, 109%, or 110% as well as an antibody sequence specifically set forth herein.

In particular embodiments, a subject antibody may have: a) a heavy chain variable region having an amino acid sequence that is at least 80% identical, at least 95% identical, at least 90%, at least 95% or at least 98% or 99% identical, to the heavy chain variable region of an anti-CD40 antibody described herein; and b) a light chain variable region having an amino acid sequence that is at least 80% identical, at least 85%, at least 90%, at least 95% or at least 98% or 99% identical, to the light chain variable region of an anti-CD40 antibody described herein. The amino acid sequence of illustrative heavy and light chain regions are set forth in SEQ ID NOs:1-56.

In particular embodiments, the antibody may comprise: a) a heavy chain variable region comprising: i. a CDR1 region that is identical in amino acid sequence to the heavy chain CDR1 region of a selected antibody described herein; ii. a CDR2 region that is identical in amino acid sequence to the heavy chain CDR2 region of the selected antibody; and iii. a CDR3 region that is identical in amino acid sequence to the heavy chain CDR3 region of the selected antibody; and b) a light chain variable domain comprising: i. a CDR1 region that is identical in amino acid sequence to the light chain CDR1 region of the selected antibody; ii. a CDR2 region that is identical in amino acid sequence to the light chain CDR2 region of the selected antibody; and iii. a CDR3 region that is identical in amino acid sequence to the light chain CDR3 region of the selected antibody; wherein the antibody specifically binds a selected target (e.g., CD40). In a further embodiment, the antibody, or antigen-binding fragment thereof, is a variant antibody wherein the variant comprises a heavy and light chain identical to the selected antibody except for up to 8, 9, 10, 11, 12, 13, 14, 15, or more amino acid substitutions in the CDR regions of the VH and VL regions. In this regard, there may be 1, 2, 3, 4, 5, 6, 7, 8, or in certain embodiments, 9, 10, 11, 12, 13, 14, 15 more amino acid substitutions in the CDR regions of the selected antibody. Substitutions may be in CDRs either in the VH and/or the VL regions. (See e.g., Muller, 1998, Structure 6:1153-1167).

Determination of the three-dimensional structures of representative polypeptides (e.g., variant CD40-specific antibodies as provided herein, for instance, an antibody protein having an antigen-binding fragment as provided herein) may be made through routine methodologies such that substitution, addition, deletion or insertion of one or more amino acids with selected natural or non-natural amino acids can be virtually modeled for purposes of determining whether a so derived structural variant retains the space-filling properties of presently disclosed species. See, for instance, Donate et al., 1994 *Prot. Sci.* 3:2378; Bradley et al., *Science* 309: 1868-1871 (2005); Schueler-Furman et al., *Science* 310:638 (2005); Dietz et al., *Proc. Nat. Acad. Sci. USA* 103:1244 (2006); Dodson et al., *Nature* 450:176 (2007); Qian et al., Nature 450:259 (2007); Raman et al. Science 327:1014-1018 (2010). Some additional non-limiting examples of computer algorithms that may be used for these and related embodiments, such as for rational design of CD40-specific antibodies antigen-binding domains thereof as provided herein, include VMD which is a molecular visualization program for displaying, animating, and analyzing large biomolecular systems using 3-D graphics and built-in scripting (see the website for the Theoretical and Computational Biophysics Group, University of Illinois at Urbana-Champagne, at ks.uiuc.edu/Research/vmd/. Many other computer programs are known in the art and available to the skilled person and which allow for determining atomic dimensions from space-filling models (van der Waals radii) of energy-minimized conformations; GRID, which seeks to determine regions of high affinity for different chemical groups, thereby enhancing binding, Monte Carlo searches, which calculate mathematical alignment, and CHARMM (Brooks et al. (1983) *J. Comput. Chem.* 4:187-217) and AMBER (Weiner et al (1981) *J. Comput. Chem.* 106: 765), which assess force field calculations, and analysis (see also, Eisenfield et al. (1991) *Am. J. Physiol.* 261:C376-386; Lybrand (1991) *J. Pharm. Belg.* 46:49-54; Froimowitz (1990) *Biotechniques* 8:640-644; Burbam et al. (1990) *Proteins* 7:99-111; Pedersen (1985) *Environ. Health Perspect.* 61:185-190; and Kini et al. (1991) *J. Biomol. Struct. Dyn.* 9:475-488). A variety of appropriate computational computer programs are also commercially available, such as from Schrödinger (Munich, Germany).

In another embodiment of invention, the anti-CD40 antibodies and humanized versions thereof are derived from rabbit monoclonal antibodies, and in particular are generated using RabMAb® technology. These antibodies are advantageous as they require minimal sequence modifications, thereby facilitating retention of functional properties after humanization using mutational lineage guided (MLG) humanization technology (see e.g., U.S. Pat. No. 7,462,697). Thus, illustrative methods for making the anti-CD40 antibodies of the present disclosure include the RabMab® rabbit monoclonal antibody technology described, for example, in U.S. Pat. Nos. 5,675,063 and 7,429,487. In this regard, in certain embodiments, the anti-CD40 antibodies of the disclosure are produced in rabbits. In particular embodiments, a rabbit-derived immortal B-lymphocyte capable of fusion with a rabbit splenocyte is used to produce a hybrid cell that produces an antibody. The immortal B-lymphocyte does not detectably express endogenous immunoglobulin heavy chain and may contain, in certain embodiments, an altered immunoglobulin heavy chain-encoding gene.

Compositions and Methods of Use

The present disclosure provides compositions comprising the CD40-specific antibodies, antigen-binding fragments thereof and administration of such composition in a variety of therapeutic settings.

Administration of the CD40-specific antibodies described herein, in pure form or in an appropriate pharmaceutical composition, can be carried out via any of the accepted modes of administration of agents for serving similar utilities. The pharmaceutical compositions can be prepared by combining an antibody or antibody-containing composition with an appropriate physiologically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. In addition, other pharmaceutically active ingredients (including other anti-cancer agents as described elsewhere herein) and/or suitable excipients such as salts, buffers and stabilizers may, but need not, be present within the composition. Administration may be achieved by a variety of different routes, including oral, parenteral, nasal, intravenous, intradermal, subcutaneous or topical. Preferred modes of administration depend upon the nature of the condition to be treated or prevented. An amount that, following administration, reduces, inhibits, prevents or delays the progression and/or metastasis of a cancer is considered effective.

In certain embodiments, the amount administered is sufficient to result in tumor regression, as indicated by a statistically significant decrease in the amount of viable tumor, for example, at least a 50% decrease in tumor mass, or by altered (e.g., decreased with statistical significance) scan dimensions. In other embodiments, the amount administered is sufficient to result in clinically relevant reduction in symptoms of a particular disease indication known to the skilled clinician.

The precise dosage and duration of treatment is a function of the disease being treated and may be determined empirically using known testing protocols or by testing the compositions in model systems known in the art and extrapolating therefrom. Controlled clinical trials may also be performed. Dosages may also vary with the severity of the condition to be alleviated. A pharmaceutical composition is generally formulated and administered to exert a therapeutically useful effect while minimizing undesirable side effects. The composition may be administered one time, or may be divided into a number of smaller doses to be administered at intervals of time. For any particular subject, specific dosage regimens may be adjusted over time according to the individual need.

The CD40-specific antibody-containing compositions may be administered alone or in combination with other known cancer treatments, such as radiation therapy, chemotherapy, transplantation, immunotherapy, hormone therapy, photodynamic therapy, etc. The compositions may also be administered in combination with antibiotics.

Typical routes of administering these and related pharmaceutical compositions thus include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions according to certain embodiments of the present invention are formulated so as to allow the active ingredients contained therein to be bioavailable upon administration of the composition to a patient. Compositions that will be administered to a subject or patient may take the form of one or more dosage units, where for example, a tablet may be a single dosage unit, and a container of a herein described CD40-specific antibody in aerosol form may hold a plurality of dosage units. Actual methods of preparing such dosage forms are known, or will be apparent, to those skilled in this art; for example, see *Remington: The Science and Practice of Pharmacy*, 20th Edition (Philadelphia College of Pharmacy and Science, 2000). The composition to be administered will, in any event, contain a therapeutically effective amount of an antibody of the present disclosure, for treatment of a disease or condition of interest in accordance with teachings herein.

A pharmaceutical composition may be in the form of a solid or liquid. In one embodiment, the carrier(s) are particulate, so that the compositions are, for example, in tablet or powder form. The carrier(s) may be liquid, with the compositions being, for example, an oral oil, injectable liquid or an aerosol, which is useful in, for example, inhalatory administration. When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent. When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition intended for either parenteral or oral administration should contain an amount of a CD40-specific antibody as herein disclosed such that a suitable dosage will be obtained. Typically, this amount is at least 0.01% of the antibody in the composition. When intended for oral administration, this amount may be varied to be between 0.1 and about 70% of the weight of the composition. Certain oral pharmaceutical compositions contain between about 4% and about 75% of the antibody. In certain embodiments, pharmaceutical compositions and preparations according to the present invention are prepared so that a parenteral dosage unit contains between 0.01 to 10% by weight of the antibody prior to dilution.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. The pharmaceutical composition may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule. The pharmaceutical composition in solid or liquid form may include an agent that binds to the antibody of the invention and thereby assists in the delivery of the compound. Suitable agents that may act in this capacity include other monoclonal or polyclonal antibodies, one or more proteins or a liposome. The pharmaceutical composition may consist essentially of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols may be delivered in single phase, bi-phasic, or tri-phasic systems in order to deliver the active ingredient(s). Delivery of the aerosol includes the necessary container, activators, valves, subcontainers, and the like, which together may form a kit. One of ordinary skill in the art, without undue experimentation may determine preferred aerosols.

The pharmaceutical compositions may be prepared by methodology well known in the pharmaceutical art. For example, a pharmaceutical composition intended to be administered by injection can be prepared by combining a composition that comprises a CD40-specific antibody as described herein and optionally, one or more of salts, buffers and/or stabilizers, with sterile, distilled water so as to form a solution. A surfactant may be added to facilitate the formation of a homogeneous solution or suspension. Surfactants are compounds that non-covalently interact with the antibody composition so as to facilitate dissolution or homogeneous suspension of the antibody in the aqueous delivery system.

The compositions may be administered in a therapeutically effective amount, which will vary depending upon a variety of factors including the activity of the specific compound (e.g., CD40-specific antibody) employed; the metabolic stability and length of action of the compound; the age, body weight, general health, sex, and diet of the patient; the mode and time of administration; the rate of excretion; the drug combination; the severity of the particular disorder or condition; and the subject undergoing therapy. Generally, a therapeutically effective daily dose is (for a 70 kg mammal) from about 0.001 mg/kg (i.e., 0.07 mg) to about 100 mg/kg (i.e., 7.0 g); preferably a therapeutically effective dose is (for a 70 kg mammal) from about 0.01 mg/kg (i.e., 0.7 mg) to about 50 mg/kg (i.e., 3.5 g); more preferably a therapeutically effective dose is (for a 70 kg mammal) from about 1 mg/kg (i.e., 70 mg) to about 25 mg/kg (i.e., 1.75 g).

Compositions comprising the CD40-specific antibodies of the present disclosure may also be administered simultaneously with, prior to, or after administration of one or more other therapeutic agents. Such combination therapy may include administration of a single pharmaceutical dosage formulation which contains a compound of the invention and one or more additional active agents, as well as administration of compositions comprising antibodies of the invention and each active agent in its own separate pharmaceutical dosage formulation. For example, an antibody as described herein and the other active agent can be administered to the patient together in a single oral dosage composition such as a tablet or capsule, or each agent administered in separate oral dosage formulations. Similarly, an antibody as described herein and the other active agent can be administered to the patient together in a single parenteral dosage composition such as in a saline solution or other physiologically acceptable solution, or each agent administered in separate parenteral dosage formulations. Where separate dosage formulations are used, the compositions comprising antibodies and one or more additional active agents can be administered at essentially the same time, i.e., concurrently, or at separately staggered times, i.e., sequentially and in any order; combination therapy is understood to include all these regimens.

Thus, in certain embodiments, also contemplated is the administration of anti-CD40 antibody compositions of this disclosure in combination with one or more other therapeutic agents. Such therapeutic agents may be accepted in the art as a standard treatment for a particular disease state as described herein, such as rheumatoid arthritis, inflammation or cancer. Exemplary therapeutic agents contemplated include cytokines, growth factors, steroids, NSAIDs, DMARDs, anti-inflammatories, chemotherapeutics, radiotherapeutics, or other active and ancillary agents.

In certain embodiments, the anti-CD40 antibodies disclosed herein may be administered in conjunction with any number of chemotherapeutic agents. Examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2, 2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®, Rhne-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid derivatives such as Targretin™ (bexarotene), Panretin™ (alitretinoin); ONTAK™ (denileukin diftitox); esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

A variety of other therapeutic agents may be used in conjunction with the anti-CD40 antibodies described herein. In one embodiment, the antibody is administered with an anti-inflammatory agent. Anti-inflammatory agents or drugs include, but are not limited to, steroids and glucocorticoids (including betamethasone, budesonide, dexamethasone, hydrocortisone acetate, hydrocortisone, hydrocortisone, methylprednisolone, prednisolone, prednisone, triamcinolone), nonsteroidal anti-inflammatory drugs (NSAIDS) including aspirin, ibuprofen, naproxen, methotrexate, sulfasalazine, leflunomide, anti-TNF medications, cyclophosphamide and mycophenolate.

Exemplary NSAIDs are chosen from the group consisting of ibuprofen, naproxen, naproxen sodium, Cox-2 inhibitors such as VIOXX® (rofecoxib) and CELEBREX® (celecoxib), and sialylates. Exemplary analgesics are chosen from the group consisting of acetaminophen, oxycodone, tramadol of proporxyphene hydrochloride. Exemplary glucocorticoids are chosen from the group consisting of cortisone, dexamethasone, hydrocortisone, methylprednisolone, prednisolone, or prednisone. Exemplary biological response modifiers include molecules directed against cell surface markers (e.g., CD4, CD5, etc.), cytokine inhibitors, such as the TNF antagonists (e.g., etanercept (ENBREL®), adalimumab (HUMIRA®) and infliximab (REMICADE®)), chemokine inhibitors and adhesion molecule inhibitors. The biological response modifiers include monoclonal antibodies as well as recombinant forms of molecules. Exemplary DMARDs include azathioprine, cyclophosphamide, cyclosporine, methotrexate, penicillamine, leflunomide, sulfasalazine, hydroxychloroquine, Gold (oral (auranofin) and intramuscular) and minocycline.

In certain embodiments, the antibodies described herein are administered in conjunction with a cytokine. By "cytokine" as used herein is meant a generic term for proteins released by one cell population that act on another cell as intercellular mediators. Examples of such cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; and other polypeptide factors including LIF and kit ligand (KL). As used herein, the term cytokine includes proteins from natural sources or from recombinant cell culture, and biologically active equivalents of the native sequence cytokines.

The compositions comprising herein described CD40-specific antibodies may be administered to an individual afflicted with a disease as described herein, including, but not limited to non-Hodgkin's lymphomas, Hodgkin's lymphoma, chronic lymphocytic leukemias, hairy cell leukemias, acute lymphoblastic leukemias, multiple myeloma, carcinomas of the pancreas, colon, gastric intestine, prostate, bladder, kidney ovary, cervix, breast, lung, nasopharynx, malignant melanoma and rituximab resistant NHL and leukemias, autoimmune and inflammatory diseases. Autoimmune diseases include but are not limited to, arthritis (including rheumatoid arthritis, reactive arthritis), systemic lupus erythematosus (SLE), psoriasis and inflammatory bowel disease (IBD), encephalomyelitis, uveitis, myasthenia gravis, multiple sclerosis, insulin dependent diabetes, Addison's disease, celiac disease, chronic fatigue syndrome, autoimmune hepatitis, autoimmune alopecia, ankylosing spondylitis, ulcerative colitis, Crohn's disease, fibromyalgia, pemphigus vulgaris, Sjogren's syndrome, Kawasaki's Disease, hyperthyroidism/Graves' disease, hypothyroidism/Hashimoto's disease, endometriosis, scleroderma, pernicious anemia, Goodpasture syndrome, Guillain-Barré syndrome, Wegener's disease, glomerulonephritis, aplastic anemia (including multiply transfused aplastic anemia patients), paroxysmal nocturnal hemoglobinuria, myelodysplastic syndrome, idiopathic thrombocytopenic purpura, autoimmune hemolytic anemia, Evan's syndrome, Factor VIII inhibitor syndrome, systemic vasculitis, dermatomyositis, polymyositis and rheumatic fever, autoimmune lymphoproliferative syndrome (ALPS), autoimmune bullous pemphigoid, Parkinson's disease, sarcoidosis, vitiligo, primary biliary cirrhosis, and autoimmune myocarditis.

Inflammatory diseases include, but are not limited to, Crohn's disease, colitis, dermatitis, psoriasis, diverticulitis, hepatitis, irritable bowel syndrome (IBS), lupus erythematous, nephritis, Parkinson's disease, ulcerative colitis, multiple sclerosis (MS), Alzheimer's disease, arthritis, rheumatoid arthritis, asthma, and various cardiovascular diseases such as atherosclerosis and vasculitis. In certain embodiments, the inflammatory disease is selected from the group consisting of rheumatoid arthritis, diabetes, gout, cryopyrin-associated periodic syndrome, and chronic obstructive pulmonary disorder. In this regard, one embodiment provides a method of treating, reducing the severity of or preventing inflammation or an inflammatory disease by administering to a patient in need thereof a therapeutically effective amount of a herein disclosed composition comprising anti-CD40 antibodies.

For in vivo use for the treatment of human disease, the antibodies described herein are generally incorporated into a pharmaceutical composition prior to administration. A pharmaceutical composition comprises one or more of the antibodies described herein in combination with a physiologically acceptable carrier or excipient as described elsewhere herein. To prepare a pharmaceutical composition, an effective amount of one or more of the compounds is mixed with any pharmaceutical carrier(s) or excipient known to those skilled in the art to be suitable for the particular mode of administration. A pharmaceutical carrier may be liquid, semi-liquid or solid. Solutions or suspensions used for parenteral, intradermal, subcutaneous or topical application may include, for example, a sterile diluent (such as water), saline solution, fixed oil, polyethylene glycol, glycerin, propylene glycol or other synthetic solvent; antimicrobial agents (such as benzyl alcohol and methyl parabens); antioxidants (such as ascorbic acid and sodium bisulfite) and chelating agents (such as ethylenediaminetetraacetic acid (EDTA)); buffers (such as acetates, citrates and phosphates). If administered intravenously, suitable carriers include physiological saline or phosphate buffered saline (PBS), and solutions containing thickening and solubilizing agents, such as glucose, polyethylene glycol, polypropylene glycol and mixtures thereof.

The compositions comprising CD40-specific antibodies as described herein may be prepared with carriers that protect the antibody against rapid elimination from the body, such as time release formulations or coatings. Such carriers include controlled release formulations, such as, but not limited to, implants and microencapsulated delivery systems, and biodegradable, biocompatible polymers, such as ethylene vinyl acetate, polyanhydrides, polyglycolic acid, PEGs, polyorthoesters, polylactic acid and others known to those of ordinary skill in the art.

Provided herein are methods of treatment using the antibodies that bind CD40. In one embodiment, an antibody of the present invention is administered to a patient having a disease involving inappropriate expression of CD40, which is meant in the context of the present disclosure to include diseases and disorders characterized by aberrant CD40 expression or activity, due for example to alterations (e.g., statistically significant increases or decreases) in the amount of a protein present, or the presence of a mutant protein, or both. An overabundance may be due to any cause, including but not limited to overexpression at the molecular level, prolonged or accumulated appearance at the site of action, or increased (e.g., in a statistically significant manner) activity of CD40 relative to that which is normally detectable. Such an overabundance of CD40 can be measured relative to normal expression, appearance, or activity of CD40 signaling events, and said measurement may play an important role in the development and/or clinical testing of the antibodies described herein.

The present antibodies are useful for the treatment of a variety of cancers. In certain embodiments, the antibodies described herein exert anti-tumor activity by activating anti-tumor immune responses. In certain embodiments, the present antibodies are useful for the treatment of a variety of cancers associated with the aberrant expression of CD40. In one embodiment of the invention provides a method for the treatment of a cancer including, but not limited to, non-Hodgkin's lymphomas, Hodgkin's lymphoma, chronic lymphocytic leukemias, hairy cell leukemias, acute lymphoblastic leukemias, multiple myeloma, carcinomas of the pancreas, colon, gastric intestine, prostate, bladder, kidney ovary, cervix, breast, lung, nasopharynx, malignant melanoma and rituximab resistant NHL and leukemias, by administering to a cancer patient a therapeutically effective amount of a herein disclosed CD40-specific antibody. An amount that, following administration, inhibits, prevents or delays the progression and/or metastasis of a cancer in a statistically significant manner (i.e., relative to an appropriate control as will be known to those skilled in the art) is considered effective.

Another embodiment provides a method for preventing metastasis of a cancer including, but not limited to, non-Hodgkin's lymphomas, Hodgkin's lymphoma, chronic lymphocytic leukemias, hairy cell leukemias, acute lymphoblastic leukemias, multiple myeloma, carcinomas of the pancreas, colon, gastric intestine, prostate, bladder, kidney ovary, cervix, breast, lung, nasopharynx, malignant melanoma and rituximab resistant NHL and leukemias, by administering to a cancer patient a therapeutically effective amount of a herein disclosed CD40-specific antibody (e.g., an amount that, following administration, inhibits, prevents or delays metastasis of a cancer in a statistically significant manner, i.e., relative to an appropriate control as will be known to those skilled in the art).

Another embodiment provides a method for preventing a cancer including, but not limited to, non-Hodgkin's lymphomas, Hodgkin's lymphoma, chronic lymphocytic leukemias, hairy cell leukemias, acute lymphoblastic leukemias, multiple myeloma, carcinomas of the pancreas, colon, gastric intestine, prostate, bladder, kidney ovary, cervix, breast, lung, nasopharynx, malignant melanoma and rituximab resistant NHL and leukemias, by administering to a cancer patient a therapeutically effective amount of a herein disclosed CD40-specific antibody.

Another embodiment provides a method for treating, ameliorating the symptoms of, inhibiting the progression of or prevention of non-Hodgkin's lymphomas, Hodgkin's lymphoma, chronic lymphocytic leukemias, hairy cell leukemias, acute lymphoblastic leukemias, multiple myeloma, carcinomas of the pancreas, colon, gastric intestine, prostate, bladder, kidney ovary, cervix, breast, lung, nasopharynx, malignant melanoma and rituximab resistant NHL and leukemias by administering to a patient afflicted by one or more of these diseases a therapeutically effective amount of a herein disclosed CD40-specific antibody.

Another embodiment provides a method for treating, ameliorating the symptoms of, inhibiting the progression of or prevention of an autoimmune disease by administering to a patient afflicted by one or more of these diseases a therapeutically effective amount of a herein disclosed anti-CD40 antibody. In this regard, autoimmune diseases include, but are not limited to, arthritis (including rheumatoid arthritis, reactive arthritis), systemic lupus erythematosus (SLE), psoriasis and inflammatory bowel disease (IBD), encephalomyelitis, uveitis, myasthenia gravis, multiple sclerosis, insulin dependent diabetes, Addison's disease, celiac disease, chronic fatigue syndrome, autoimmune hepatitis, autoimmune alopecia, ankylosing spondylitis, ulcerative colitis, Crohn's disease, fibromyalgia, pemphigus vulgaris, Sjogren's syndrome, Kawasaki's Disease, hyperthyroidism/Graves' disease, hypothyroidism/Hashimoto's disease, endometriosis, scleroderma, pernicious anemia, Goodpasture syndrome, Guillain-Barré syndrome, Wegener's disease, glomerulonephritis, aplastic anemia (including multiply transfused aplastic anemia patients), paroxysmal nocturnal hemoglobinuria, myelodysplastic syndrome, idiopathic thrombocytopenic purpura, autoimmune hemolytic anemia, Evan's syndrome, Factor VIII inhibitor syndrome, systemic vasculitis, dermatomyositis, polymyositis and rheumatic fever, autoimmune lymphoproliferative syndrome (ALPS), autoimmune bullous pemphigoid, Parkinson's disease, sarcoidosis, vitiligo, primary biliary cirrhosis, and autoimmune myocarditis.

Another embodiment provides a method for treating, ameliorating the symptoms of, inhibiting the progression of or prevention of an inflammatory disease by administering to a patient afflicted by one or more of these diseases a therapeutically effective amount of a herein disclosed anti-CD40 antibody. Inflammatory diseases include, but are not limited to, Crohn's disease, colitis, dermatitis, psoriasis, diverticulitis, hepatitis, irritable bowel syndrome (IBS), lupus erythematous, nephritis, Parkinson's disease, ulcerative colitis, multiple sclerosis (MS), Alzheimer's disease, arthritis, rheumatoid arthritis, asthma, and various cardiovascular diseases such as atherosclerosis and vasculitis. In certain embodiments, the inflammatory disease is selected from the group consisting of rheumatoid arthritis, diabetes, gout, cryopyrin-associated periodic syndrome, and chronic obstructive pulmonary disorder.

In another embodiment, anti-CD40 antibodies of the present invention are used to determine the structure of bound antigen, e.g., conformational epitopes, which structure may then be used to develop compounds having or mimicking this structure, e.g., through chemical modeling and SAR methods.

Various other embodiments of the present invention relate, in part, to diagnostic applications for detecting the presence of cells or tissues expressing CD40. Thus, the present disclosure provides methods of detecting CD40 in a sample, such as detection of cells or tissues expressing CD40. Such methods can be applied in a variety of known detection formats, including, but not limited to immunohistochemistry (IHC), immunocytochemistry (ICC), in situ hybridization (ISH), whole-mount in situ hybridization (WISH), fluorescent DNA in situ hybridization (FISH), flow cytometry, enzyme immuno-assay (EIA), and enzyme linked immuno-assay (ELISA).

ISH is a type of hybridization that uses a labeled complementary DNA or RNA strand (i.e., primary binding agent) to localize a specific DNA or RNA sequence in a portion or section of a cell or tissue (in situ), or if the tissue is small enough, the entire tissue (whole mount ISH). One having ordinary skill in the art would appreciate that this is distinct from immunohistochemistry, which localizes proteins in tissue sections using an antibody as a primary binding agent. DNA ISH can be used on genomic DNA to determine the structure of chromosomes. Fluorescent DNA ISH (FISH) can, for example, be used in medical diagnostics to assess chromosomal integrity. RNA ISH (hybridization histochemistry) is used to measure and localize mRNAs and other transcripts within tissue sections or whole mounts.

In various embodiments, the antibodies described herein are conjugated to a detectable label that may be detected directly or indirectly. In this regard, an antibody "conjugate" refers to an anti-CD40 antibody that is covalently linked to a detectable label. In the present invention, DNA probes, RNA probes, monoclonal antibodies, antigen-binding fragments thereof, and antibody derivatives thereof, such as a single-chain-variable-fragment antibody or an epitope tagged antibody, may all be covalently linked to a detectable label. In "direct detection", only one detectable antibody is used, i.e., a primary detectable antibody. Thus, direct detection means that the antibody that is conjugated to a detectable label may be detected, per se, without the need for the addition of a second antibody (secondary antibody).

A "detectable label" is a molecule or material that can produce a detectable (such as visually, electronically or otherwise) signal that indicates the presence and/or concentration of the label in a sample. When conjugated to an antibody, the detectable label can be used to locate and/or quantify the target to which the specific antibody is directed. Thereby, the presence and/or concentration of the target in a sample can be detected by detecting the signal produced by the detectable label. A detectable label can be detected directly or indirectly, and several different detectable labels conjugated to different specific-antibodies can be used in combination to detect one or more targets. Examples of detectable labels, which may be detected directly, include fluorescent dyes and radioactive substances and metal particles. In contrast, indirect detection requires the application of one or more additional antibodies, i.e., secondary antibodies, after application of the primary antibody. Thus, the detection is performed by the detection of the binding of the secondary antibody or binding agent to the primary detectable antibody. Examples of primary detectable binding agents or antibodies requiring addition of a secondary binding agent or antibody include enzymatic detectable binding agents and hapten detectable binding agents or antibodies.

In some embodiments, the detectable label is conjugated to a nucleic acid polymer which comprises the first binding agent (e.g., in an ISH, WISH, or FISH process). In other embodiments, the detectable label is conjugated to an antibody which comprises the first binding agent (e.g., in an IHC process).

Examples of detectable labels which may be conjugated to antibodies used in the methods of the present disclosure include fluorescent labels, enzyme labels, radioisotopes, chemiluminescent labels, electrochemiluminescent labels, bioluminescent labels, polymers, polymer particles, metal particles, haptens, and dyes.

Examples of fluorescent labels include 5-(and 6)-carboxyfluorescein, 5- or 6-carboxyfluorescein, 6-(fluorescein)-5-(and 6)-carboxamido hexanoic acid, fluorescein isothiocyanate, rhodamine, tetramethylrhodamine, and dyes such as Cy2, Cy3, and Cy5, optionally substituted coumarin including AMCA, PerCP, phycobiliproteins including R-phycoerythrin (RPE) and allophycoerythrin (APC), Texas Red, Princeton Red, green fluorescent protein (GFP) and analogues thereof, and conjugates of R-phycoerythrin or allophycoerythrin, inorganic fluorescent labels such as particles based on semiconductor material like coated CdSe nanocrystallites.

Examples of polymer particle labels include micro particles or latex particles of polystyrene, PMMA or silica, which can be embedded with fluorescent dyes, or polymer micelles or capsules which contain dyes, enzymes or substrates.

Examples of metal particle labels include gold particles and coated gold particles, which can be converted by silver stains. Examples of haptens include DNP, fluorescein isothiocyanate (FITC), biotin, and digoxigenin. Examples of enzymatic labels include horseradish peroxidase (HRP), alkaline phosphatase (ALP or AP), β-galactosidase (GAL), glucose-6-phosphate dehydrogenase, β-N-acetylglucosamimidase, β-glucuronidase, invertase, Xanthine Oxidase, firefly luciferase and glucose oxidase (GO). Examples of commonly used substrates for horseradishperoxidase include 3,3'-diaminobenzidine (DAB), diaminobenzidine with nickel enhancement, 3-amino-9-ethylcarbazole (AEC), Benzidine dihydrochloride (BDHC), Hanker-Yates reagent (HYR), Indophane blue (IB), tetramethylbenzidine (TMB), 4-chloro-1-naphtol (CN), .alpha.-naphtol pyronin (.alpha.−NP), o-dianisidine (OD), 5-bromo-4-chloro-3-indolyl-phosp-hate (BCIP), Nitro blue tetrazolium (NBT), 2-(p-iodophenyl)-3-p-nitropheny-I-5-phenyl tetrazolium chloride (INT), tetranitro blue tetrazolium (TNBT), 5-bromo-4-chloro-3-indoxyl-beta-D-galactoside/ferro-ferricyanide (BCIG/FF).

Examples of commonly used substrates for Alkaline Phosphatase include Naphthol-AS-B 1-phosphate/fast red TR (NABP/FR), Naphthol-AS-MX-phosphate/fast red TR (NAMP/FR), Naphthol-AS-B1-phosphate/-fast red TR (NABP/FR), Naphthol-AS-MX-phosphate/fast red TR (NAMP/FR), Naphthol-AS-B1-phosphate/new fuschin (NABP/NF), bromochloroindolyl phosphate/nitroblue tetrazolium (BCIP/NBT), 5-Bromo-4-chloro-3-indolyl-b-d-galactopyranoside (BCIG).

Examples of luminescent labels include luminol, isoluminol, acridinium esters, 1,2-dioxetanes and pyridopyridazines. Examples of electrochemiluminescent labels include ruthenium derivatives. Examples of radioactive labels include radioactive isotopes of iodide, cobalt, selenium, tritium, carbon, sulfur and phosphorous.

Detectable labels may be linked to the antibodies described herein or to any other molecule that specifically binds to a biological marker of interest, e.g., an antibody, a nucleic acid probe, or a polymer. Furthermore, one of ordinary skill in the art would appreciate that detectable labels can also be conjugated to second, and/or third, and/or fourth, and/or fifth binding agents or antibodies, etc. Moreover, the skilled artisan would appreciate that each additional binding agent or antibody used to characterize a biological marker of interest may serve as a signal amplification step. The biological marker may be detected visually using, e.g., light microscopy, fluorescent microscopy, electron microscopy where the detectable substance is for example a dye, a colloidal gold particle, a luminescent reagent. Visually detectable substances bound to a biological marker may also be detected using a spectrophotometer. Where the detectable substance is a radioactive isotope detection can be visually by autoradiography, or non-visually using a scintillation counter. See, e.g., Larsson, 1988, Immunocytochemistry: Theory and Practice, (CRC Press, Boca Raton, Fla.); Methods in Molecular Biology, vol. 80 1998, John D. Pound (ed.) (Humana Press, Totowa, N.J.).

The invention further provides kits for detecting CD40 or cells or tissues expressing CD40 in a sample, wherein the kits contain at least one antibody, polypeptide, polynucleotide, vector or host cell as described herein. In certain embodiments, a kit may comprise buffers, enzymes, labels, substrates, beads or other surfaces to which the antibodies of the invention are attached, and the like, and instructions for use.

EXAMPLES

Example 1

Production and Humanization of Anti-CD40 Antibodies

Four New Zealand white rabbits were immunized with recombinant rabbit Fc-hCD40. The rabbit with the highest serum titers of specific binding to human CD40 was chosen for cell fusion. A total of 172 hybridomas were identified as positive binders to soluble Fc-hCD40, of which 44 clones were found to be positive binders to cell surface CD40. After the epitope clustering assay, 24 representative hybridomas were selected for recombinant expression and further characterization. Secondary functional screening was carried out as described further below and included: 1) induction of DC maturation as measured by CD80, CD83, CD86 upregulation (agonist activity); 2) induction of direct tumor growth inhibition (agonist activity); and 3) ADCC antibody effector function. Candidates were selected based on dual functional screenings which included two arms: 1) binding affinity, antibody internalization, antibody dependent cellular cytotoxicity (ADCC), complement dependent cytotoxicity (CDC), and antibody dependent cellular phagocytosis (ADCP); and 2) agonist DC activation/maturation function, receptor-ligand interaction, mixed lymphocyte reaction (MLR), cell proliferation and apoptosis.

Screening Agonist Antibodies Via Dendritic Cell Maturation

Figure 1B:
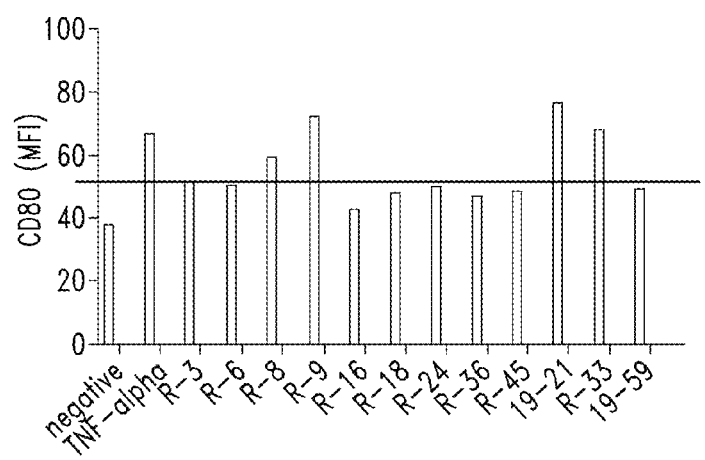
Figure 1C:
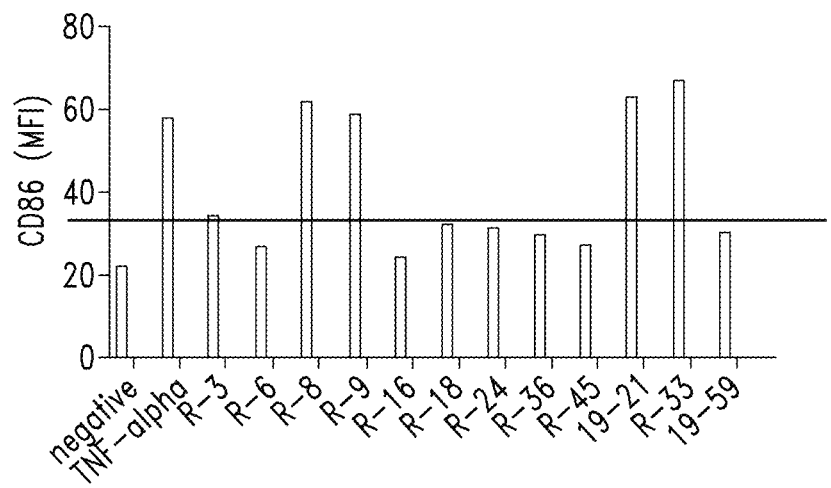
Figure 1D:
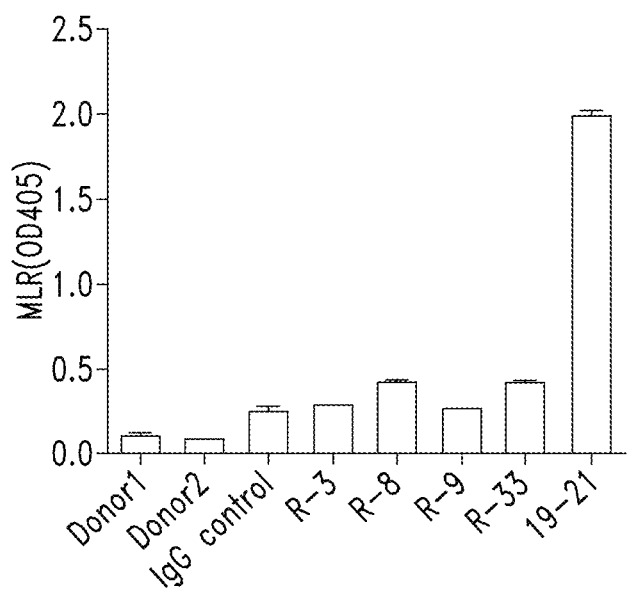

To further clarify the agonist or antagonist effect of the initial panel of anti-CD40 antibodies, a DC maturation assay was used as an indicator to screen for functional antibodies. Anti-CD40 or control antibodies were added to human monocyte-derived DC culture solution for 2 days. Upregulation of CD83, one of the best-known maturation markers for human dendritic cells, was measured to screen for agonist antibodies. 5C11, a mouse monoclonal antibody that induces dendritic cell maturation was used as positive control. Antibodies R-3, R-6, R-8, R-9, R-16, R-18, R-24, R-33, R-36, 19-21, 19-45 and 19-59 increased more than 50% of CD83 expression as compared with Ig control (FIG. 1A). DC maturation was further determined by measuring the antibody-induced up-regulation of co-stimulatory molecules CD80 and CD86 for the selected antibodies. As shown in FIG. 1B and FIG. 1C, antibodies R-3, R-8, R-9, R-33 and 19-21 up-regulated both CD80 and CD86, while the other antibodies had only modest effects. These results were consistent with the CD83 modulation effects by these antibodies. Interestingly, among the antibodies capable of inducting DC maturation, only clone 19-21 showed strong activity to enhance T cells proliferation in a mixed-lymphocyte reaction (FIG. 1D).

Screening for Direct Inhibition of Tumor Growth

Figure 2:
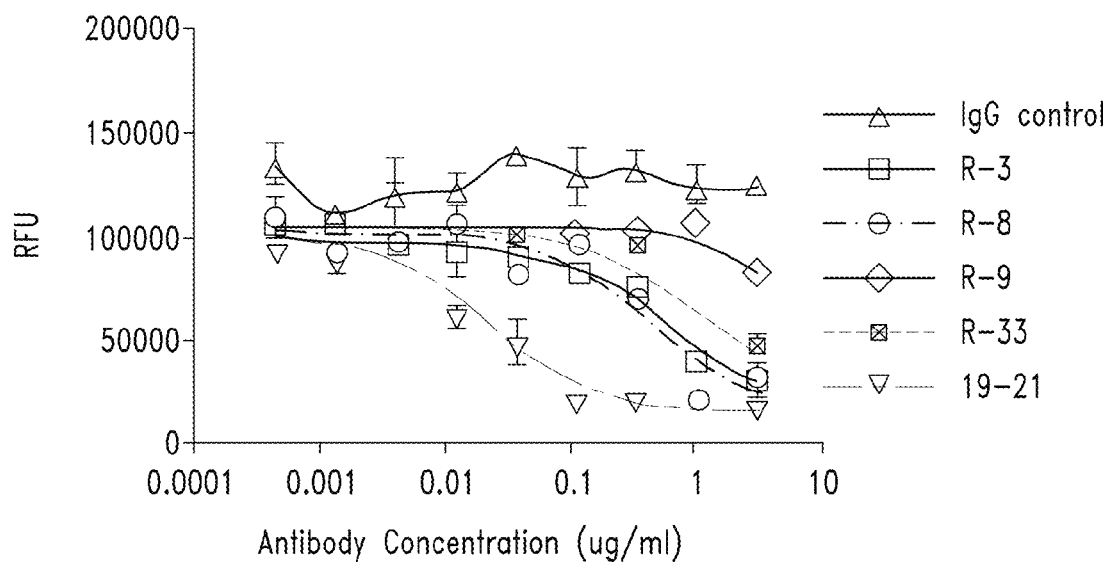
FIG. 2 is a graph showing the comparison of lead candidates in the inhibition of Ramos cell proliferation.

The panel of agonist anti-CD40 antibodies was further assessed for the ability to induce the tumor growth inhibition of CD40 expressing tumor cells. All anti-CD40 antibodies tested inhibited tumor cell proliferation. The antibody 19-21 demonstrated the highest potency (FIG. 2).

Screening for ADCC Activity

Figure 3:
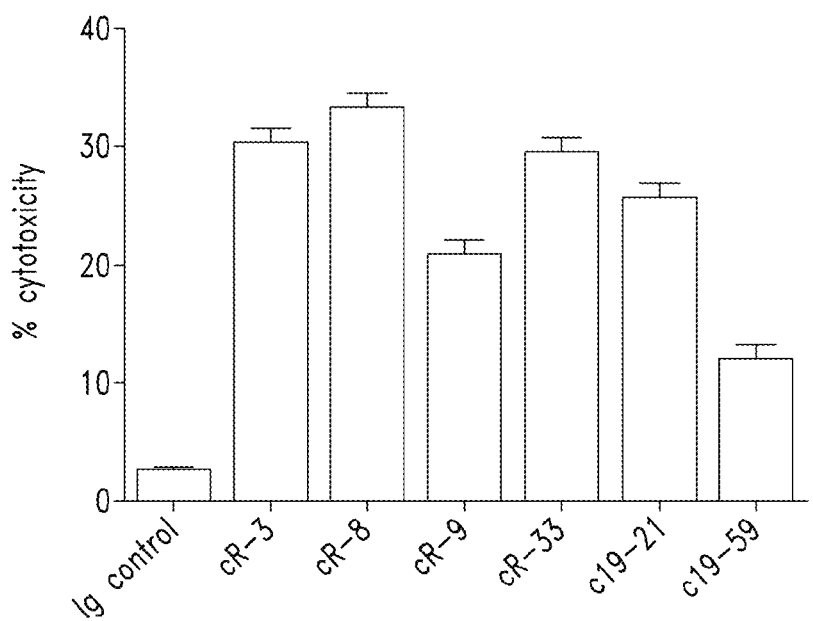
FIG. 3 is a bar graph showing the results of an ADCC assay. Effector (human PBMC):target cell (Ramos cell) ratio of 40:1.

In addition to induction of APC activation and tumor growth inhibition, antibody effector function, ADCC, was used as an important criterion to screen and rank the antibody candidates. In order to conduct the ADCC assay using human PBMC, all the selected antibodies were converted from rabbit mAb to chimeric mAb with rabbit Fab and human IgG1. As shown in FIG. 3, all the selected candidates showed significant ADCC activity as compared to IgG1 control. Based on the maximal ADCC activity, the lead mAbs can be ranked cR-8>cR-3>cR-33>c19-21>cR-9>c19-59.

Four candidates (c19-21, cR-8, cR-3, cR-33) were selected based on in vitro functional screening. Their in vitro characterizations are summarized in Table 1. Antibody c19-21 strongly enhances DC activation and tumor growth inhibition, while antibodies cR-8 and cR-3 showed more potent ADCC activity.

TABLE 1

Characteristics of 4 candidate anti-CD40 antibodies:

| Antibody | c19-21 | cR-8 | cR3 | cR33 |
|---|---|---|---|---|
| Blocks CD40L binding | Yes | Yes | Yes | Yes |
| Enhances DC maturation | Strong | Strong | Strong | Strong |
| Pro-apoptosis activity (IC50) | 0.02 µg/ml | 0.45 µg/ml | 0.57 µg/ml | 0.90 µg/ml |
| ADCC (% cytotoxicity of Ramos cell at 1 µg/ml) | 26% | 33% | 30% | 29% |

In Vivo Anti-Tumor Activity Screening

Figure 4A:
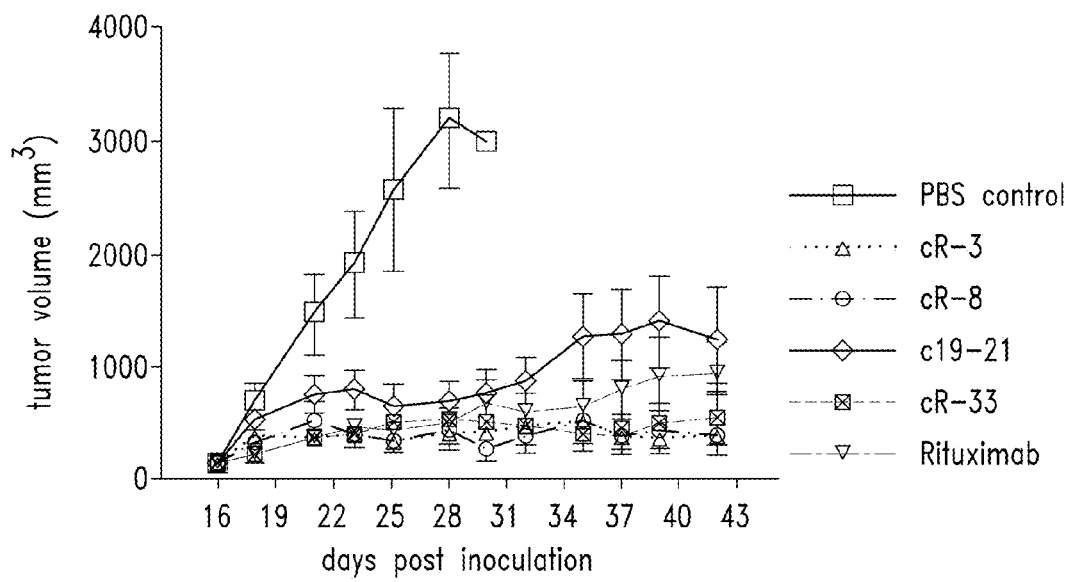
FIG. 4A and FIG. 4B are graphs showing the results of in vivo screening of anti-tumor activity of anti-CD40 candidates.
Figure 4B:
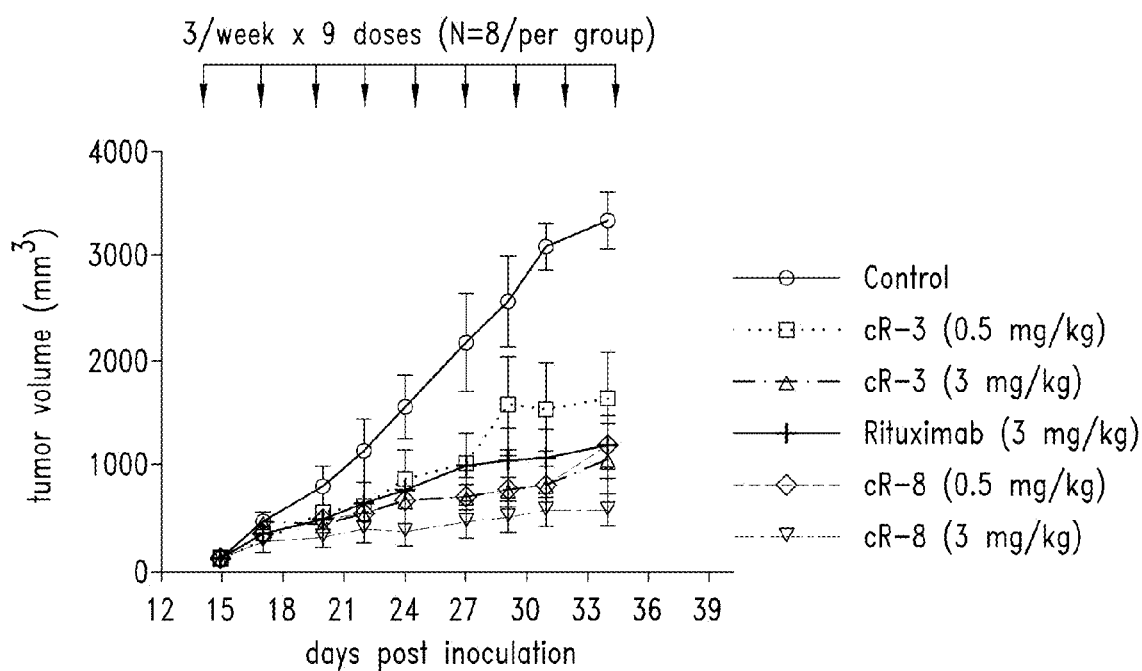

As the top 4 candidates showed different potencies in different in vitro assays, we conducted in vivo studies to evaluate and compare their anti-tumor activity for lead selection. The Ramos tumor xenograft model was used. Tumor bearing mice were treated i.p. with 5 mg/kg of chimeric antibodies cR-3, cR-8, cR-33 or c19-21 3 times per week for a total of 9 doses (eight animals per group). The anti-tumor activity of rituximab with the same regimen was used as a reference. As shown in FIG. 4A, cR-8 and cR-3 showed the strongest anti-tumor effect. In contrast, 19-21 exhibited lower anti-tumor activity with faster tumor rebound after termination of dosing. The anti-tumor effect of cR-33 was in between, but still exhibited better in vivo efficacy than rituximab. The in vivo potency of antibodies cR-3 and cR-8 was further evaluated in a dose-response study. As shown in FIG. 4B, cR-8 showed more potent anti-tumor efficacy than cR-3, and thus was identified as the lead anti-CD40 antibody.

The amino acid sequence of the heavy chain and light chain variable regions of the R-8 clone are set forth in SEQ ID NOs:1 and 2. The amino acid sequences of the CDRs of the VH and VL are set forth in SEQ ID NOs:3-5 and 6-8, respectively. The amino acid sequence of the heavy and light chain sequences of several of the other antibody candidates that showed functional activity are set forth in SEQ ID NOs:11-56. VHCDR and VLCDR amino acid sequences for these antibodies are provided in SEQ ID Nos:57-194. FIG. 16 shows an alignment of these sequences, including the R-8 clone, with CDRs underlined.

R-8 was humanized using a proprietary mutational lineage guided (MLG) humanization technology (see e.g., U.S. Pat. No. 7,462,697). The light and heavy chain framework of the humanized R-8 (APX005) are 95% identical to the human germline sequences. The amino acid sequence of the humanized VH and VL regions are set forth in SEQ ID NOs:9 and 10, respectively. The binding of APX005 to CD40 were found to be similar to its parental clone R-8.

Example 2

In Vitro Characterization of the APX005 Humanized Anti-CD40 Antibody

Numerous in vitro experiments were conducted to further characterize the APX005 humanized antibody.

APX005 Selectively Binds to CD40

Figure 5:
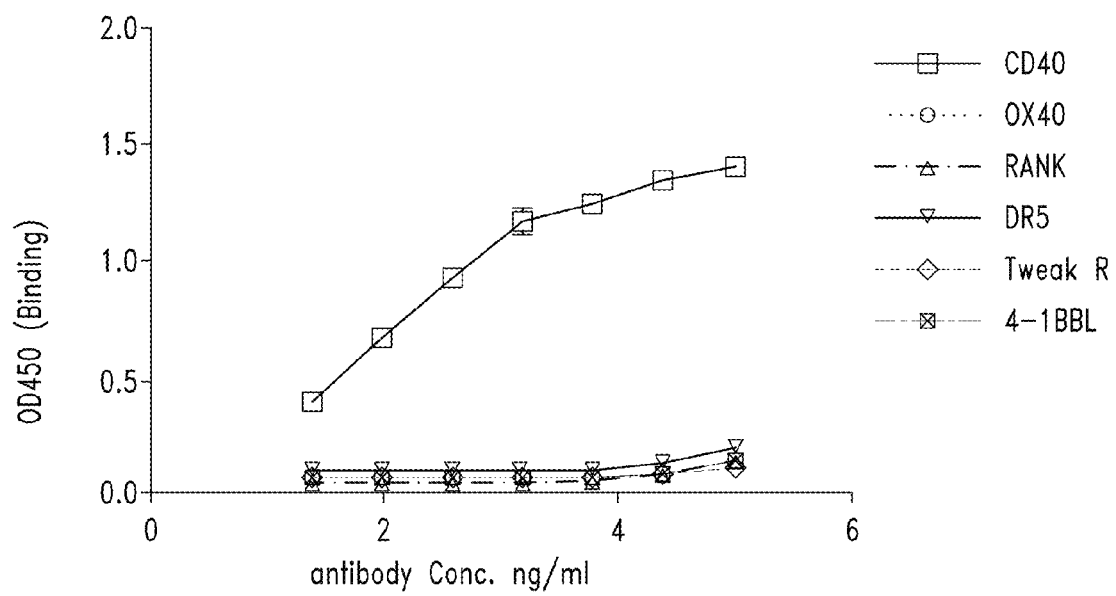
FIG. 5 is a graph showing the results of an ELISA assay demonstrating that APX005 selectively binds to CD40 but not to other TNFR family members.

Binding selectivity of APX005 was assessed by direct ELISA to a panel of TNFR family proteins. A total of 1 μg/ml of fusion protein of rabbit Fc and CD40, RANK, TweakR, OX40, DR5 and 4-1BB were coated on ELISA plates. Bound APX005 was detected using goat anti-human HRP-conjugated IgG. As shown in FIG. 5, APX005 selectively binds to human CD40 but not other TNFR family proteins tested.

APX005 Blocks Binding of CD40L to CD40

Figure 6:
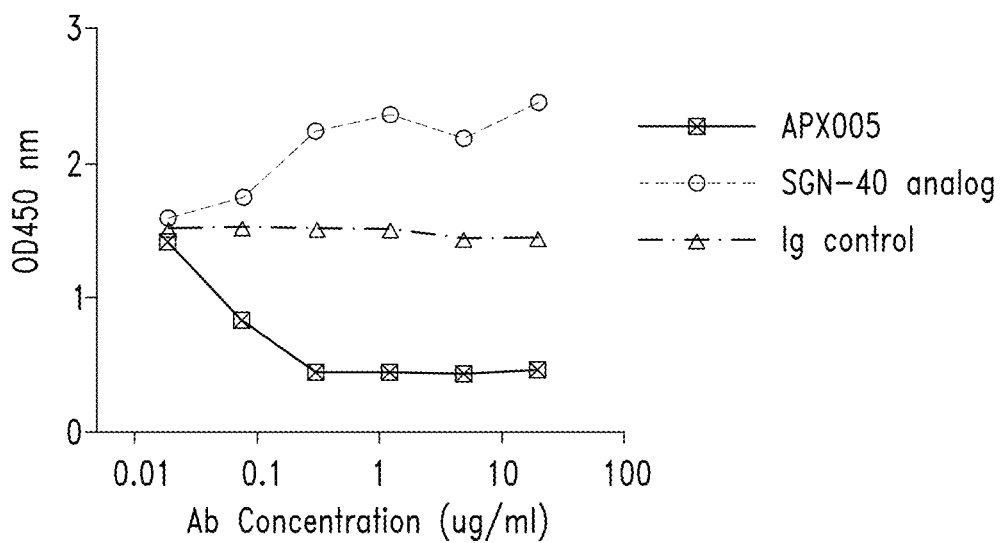
FIG. 6 is a graph showing the results of an ELISA assay demonstrating that APX005 blocks the binding of CD40L to CD40.

An ELISA was conducted to assess the effect of APX005 on CD40L binding to CD40. In particular, CD40L (4 μg/ml final concentration) was used to bind the immobilized human CD40 onto an ELISA plate, and changes in the binding amount of CD40L to CD40 were measured after pre-incubating immobilized CD40 with APX005. CD40L binding to immobilized CD40 was detected by a mouse anti-CD40L monoclonal antibody. As shown in FIG. 6, APX005 blocks the binding of CD40L to CD40. In contrast, SGN-40 increases the binding.

APX005/CD40 Complex is not Internalized

Figure 7:
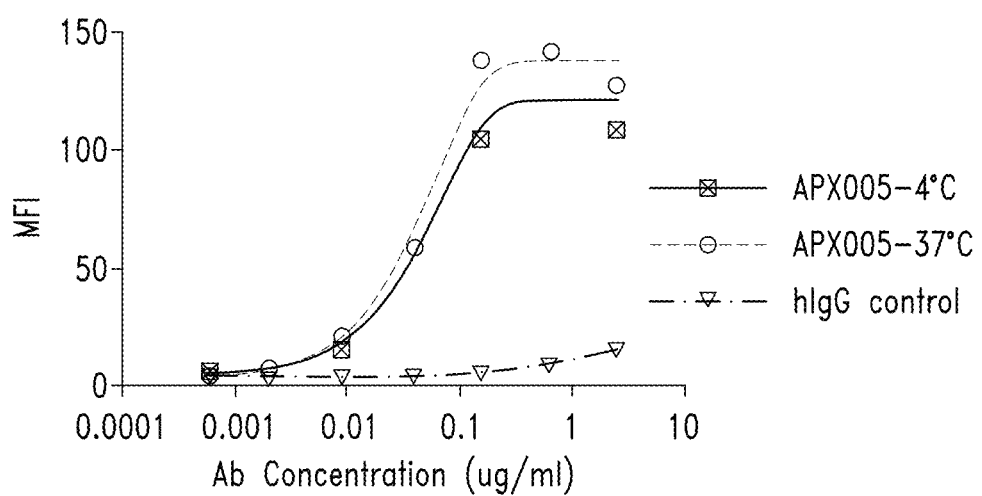
FIG. 7 is a graph showing that APX005 is not internalized upon binding to CD40 positive cells.

In order to assess the target mediated-internalization of APX005 for evaluating its impact on ADCC activity, Ramos cells were incubated with APX005 for 4 h at 37° C., a temperature permissive for internalization, or at 4° C. for 30 minutes, a temperature at which internalization is minimized. Cells were washed with staining buffer, followed by incubation with Alexa 488 labeled goat anti-human IgG for an additional 30 minutes at 4° C. FACS analysis was performed to examine the level of APX005 on the cell surface. As shown in FIG. 7, there was no reduction (slight increase) of APX005 level on the cell surface after incubation at 37° C. The data suggest that upon binding to CD40 APX005/CD40 complex was not internalized by tumor cells, thus providing optimal conditions for recruiting the effector cells for ADCC.

APX005 Mediates ADCC

Figures 8A, 8B:
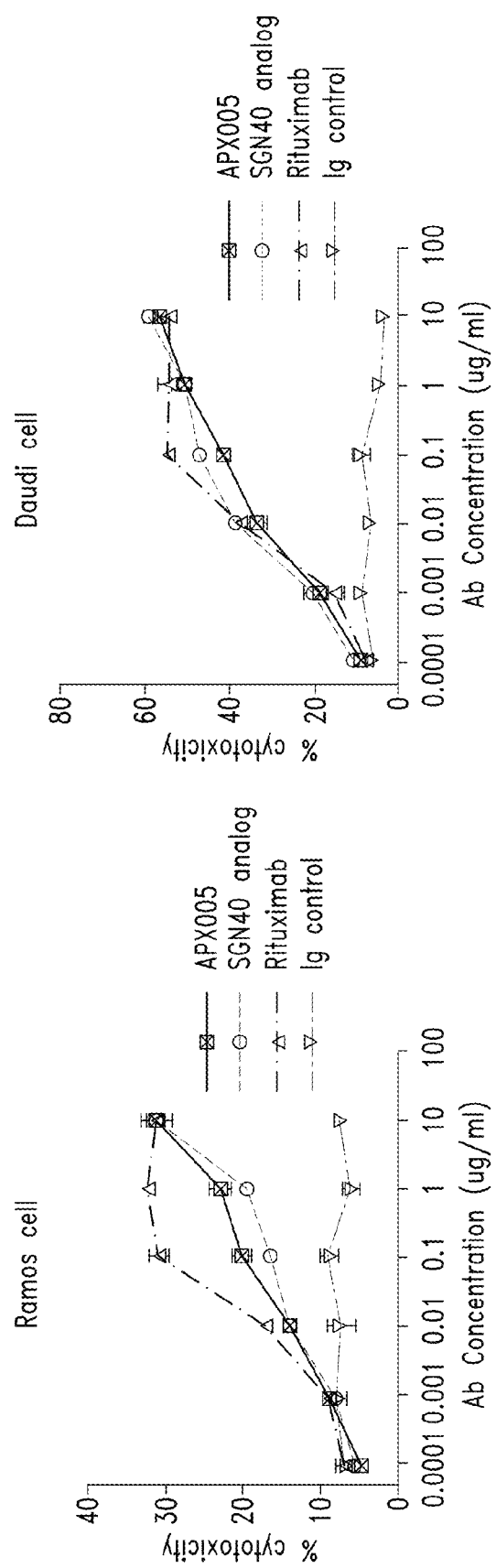
FIG. 8A and FIG. 8B are graphs showing APX005-mediated ADCC of CD40 positive Ramos (FIG. 8A) and Daudi (FIG. 8B) tumor cells.

In order to assess ADCC activity of APX005 on CD40 expressing tumor cells, CD40 expressing Ramos and Daudi were used as target cells and fresh human peripheral blood mononuclear cell (PBMC) were used as the effector cells. ADCC was measured by a calcein-AM release assay. Target cells were labeled with calcein-AM (15 uM/$10^6$ cells), washed, and plated in triplicate at $5 \times 10^3$ per well in round-bottomed 96-well plates. Increasing concentrations (0.0001-10 μg/mL) of either APX005 or control antibodies were pre-incubated at 4° C. for 30 minutes, after which PBMC effector cells from healthy human donors were added with a final effector:target cell ratio of 40:1 in a final volume of 200 uL per well. Experiments were performed using PBMC from at least three different donors. After a 4-hour incubation, 100 μL culture supernatants were transferred to a Black View Plate-96 plate and arbitrary fluorescent units (AFU) were read on a Victor II plate reader (485 nm excitation/535 nm emission). Percent specific lysis=(AFU mean experimental release—AFU mean spontaneous release)/(AFU mean maximal release—AFU mean spontaneous release). As shown in FIG. 8, APX005 induced ADCC in a dose-dependent fashion. A similar effect was observed for SGN-40. The different sensitivity of Ramos and Daudi cells to the ADCC may be due to different CD40 expression level (Cancer Res 2005; 65: 8331-8338).

APX005 Inhibits Tumor Cell Proliferation

Figures 9A, 9B:
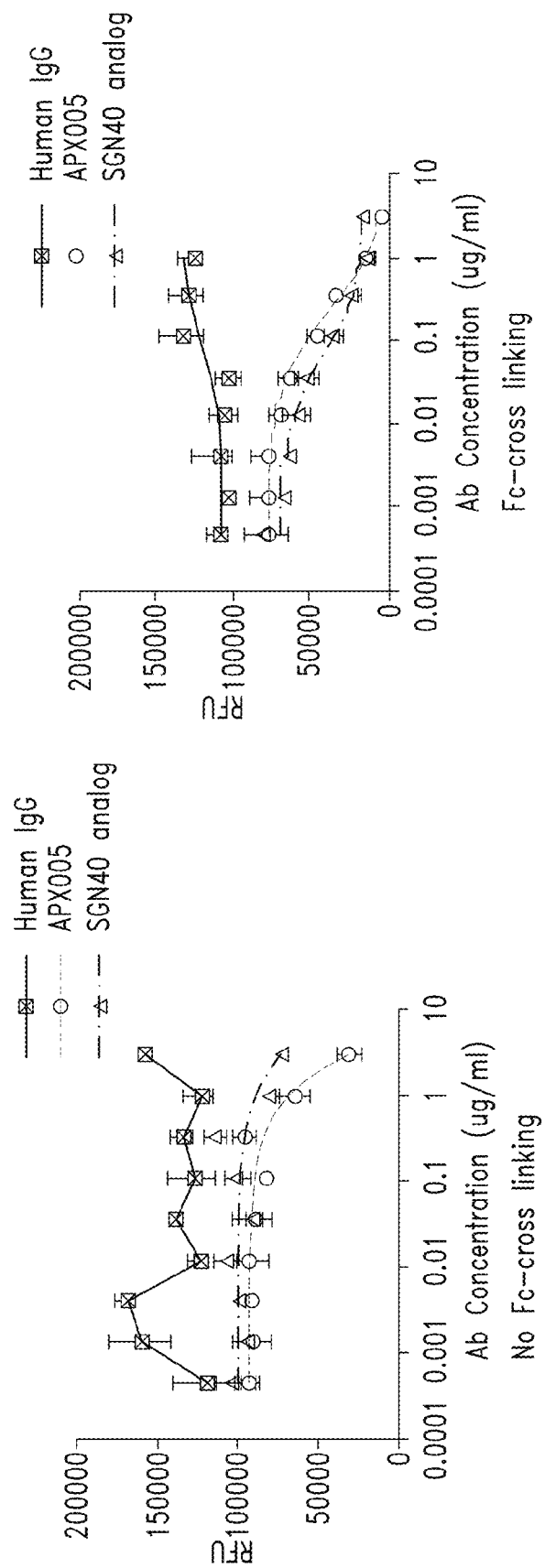
FIG. 9A and FIG. 9B are graphs showing in vitro inhibition of Ramos tumor cell proliferation by APX005. Panel A: without Fc crosslinking; Panel B: with Fc crosslinking.

To assess the ability of APX005 to inhibit tumor cell proliferation, Ramos cells were seeded in 96-well flat-bottom plates at 50,000 cells/well in 200 μL RPMI 1640 supplemented with 10% FBS containing varying concentrations of APX005, SGN-40 or a control human IgG. For cross-linking, APX005, SGN-40 or control IgG was pre-incubated with F(ab')2 fragments of a goat anti-human IgG Fc fragment-specific antibody in the medium for 30 minutes at room temperature before being added to the cells. Cells were treated for a total of 72 hours. Then 10% AlamarBlue® (Serotec, Oxford, UK) was added to each well and incubated for an additional 24 hours. Cell viability was measured by a CytoFluor® fluorescence reader with an excitation wavelength of 530 nm and emission wavelength of 590 nm. All studies were conducted twice and in triplicates for each sample concentration. As shown in FIG. 9, monomer APX005 inhibited proliferation of Ramos cells (FIG. 9A). When APX005 was cross-linked by a secondary antibody, it delivered an increased and dose-dependent proliferation inhibitory effect (FIG. 9B). The cross-linking of APX005 can be achieved in vivo by Fc receptor expressing cells.

APX005 Induces DC Activation

Figure 10:
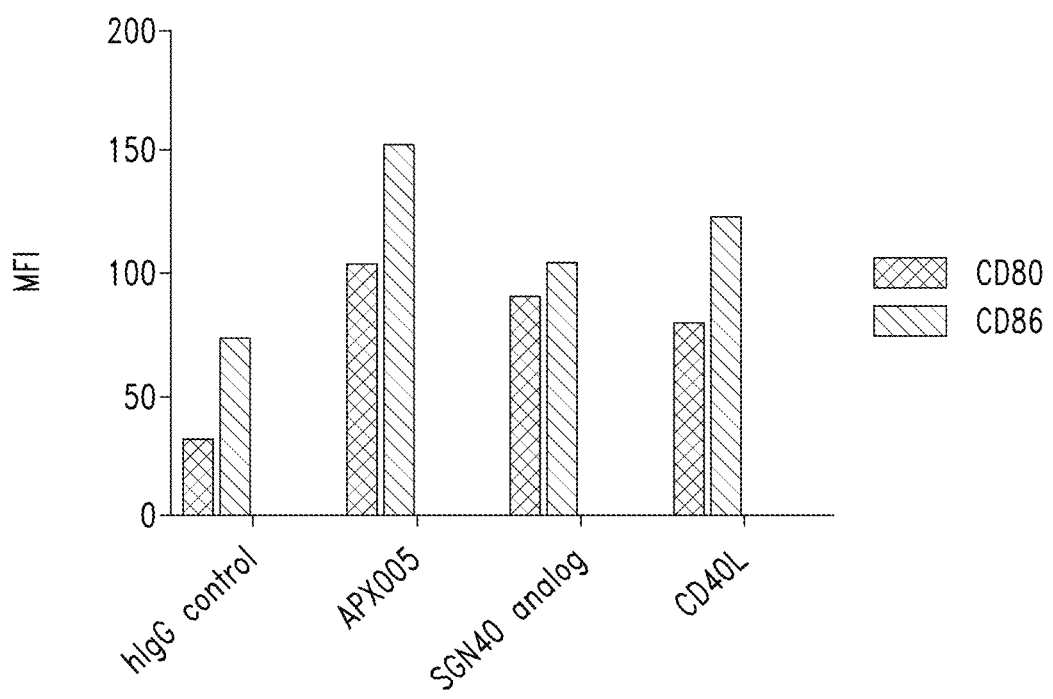
FIG. 10 is a bar graph showing induction of DC activation by APX005.

In order to assess the ability of APX005 to stimulate the maturation of DC cells, PBMC were prepared by density gradient centrifugation using lymphocyte isolation solution. Adherent monocytes were harvested after incubating for 2 hours at 37° C. Isolated monocytes were cultured with 100 ng/ml of recombinant human GM-CSF and 100 ng/ml of recombinant human IL-4 in RPM11640 media supplemented with 10% FCS in a 24-well plate. Half of the medium was changed after 3 days. On day 5 of culturing, 1.3 nM of anti-CD40 antibodies, CD40L or the control antibody were added to the DC cells, and further cultured for 48 h in a 24-well plate. For DC activation marker staining, PE-conjugated anti-CD83, anti-CD86 antibody and anti-CD80 antibody were used. Analysis was performed using FACS. The data is from one representative study. As shown in FIG. 10, APX005 induced marked DC maturation and its effect appears more potent than SGN-40 and CD40L. Increased activation of DC may lead to more potent anti-tumor T cell responses.

APX005 is Cross Reactive with Monkey CD40 but not Mouse CD40

Figure 11A:
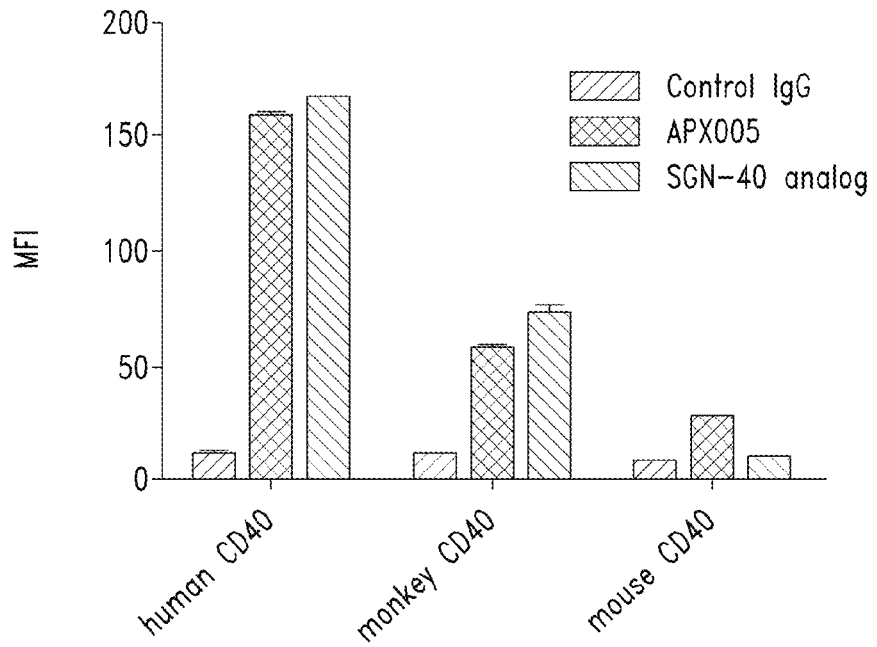
FIGS. 11A and 11B show that APX005 binds to human and monkey CD40 but not mouse CD40.

Cross-reactivity was assessed by direct ELISA. A total of 1 μg/ml of human CD40, monkey CD40 or mouse CD40 was coated on ELISA plates followed by incubation with 1 μg/ml of APX005 or control IgG1. Antibodies bound to CD40 were detected using goat anti-human IgG conjugated with HRP. APX005 clearly cross-reacts with monkey CD40 but not mouse CD40. (FIG. 11A)

Figure 11B:
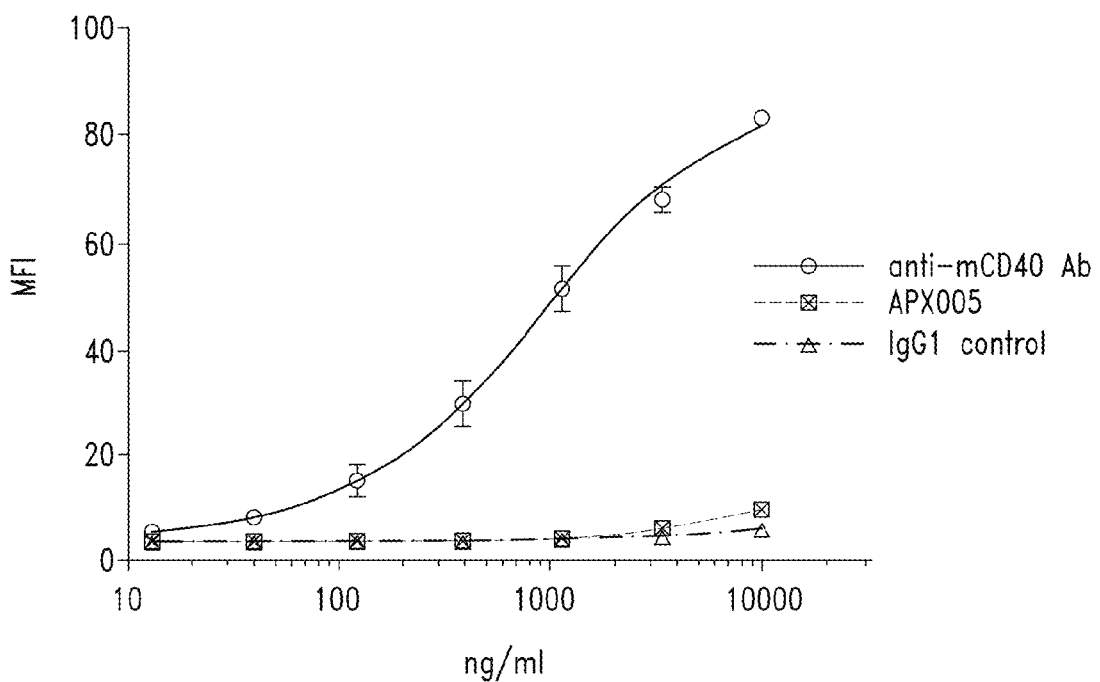

Cross-reactivity of APX005 with mouse CD40 was further determined by FACS binding to a mouse A20 cell line which expresses mouse CD40. An aliquot of $0.5 \times 10^6$ A20 cells was added to 96 well plates and incubated with 100 μl diluted rat anti-mouse CD40 antibody conjugated with PE, APX005 or IgG1 control antibodies. After washing, 100 μl Goat-anti human IgG (H+L) conjugated with RPE (Southern Biotech CAT#2040-09) were added at 1:200 dilution in PBS to the sample and incubated for detection of APX005 and control human IgG1. A rat anti-mouse CD40 antibody conjugated with PE was used as positive control. Samples were re-suspended with 0.5 ml PBS and analyzed by FACS. The FACS data showed that APX005 does not cross-react with mouse CD40 (FIG. 11B).

In summary, the experiments in this Example showed that APX005 is a humanized IgG1 antibody that binds CD40. APX005 specifically binds to CD40 with a Kd of $9.6 \times 10^{-10}$ M and blocks CD40L binding to CD40. This is in contrast to the SGN40 anti-CD40 antibody that enhances the CD40-CD40L interaction. This suggests that these two antibodies bind to distinct epitopes. In vitro, APX005 showed potent ADCC activity to CD40 positive lymphoma cells (Ramos and Daudi) as well as the ability to directly inhibit tumor cell (Ramos) proliferation upon cross-linking. APX005 also stimulated the maturation of dendritic cells to enhance cellular immune response. Additionally, APX005 was shown to cross-react with monkey CD40.

Example 3

In Vivo Characterization of the APX005 Humanized Anti-CD40 Antibody

Numerous in vivo experiments were conducted to further characterize the APX005 humanized antibody.

APX005 Inhibition of Tumor Growth in the Ramos Model

Figure 12A:
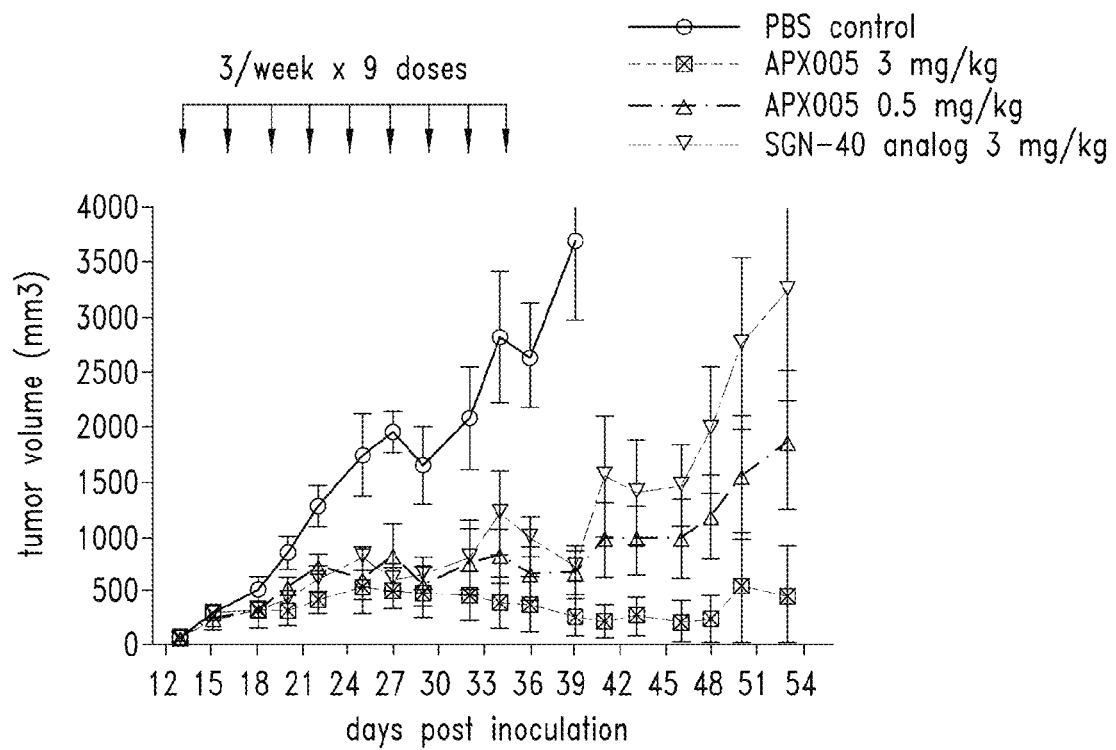
FIG. 12A is a graph showing APX005 inhibition of tumor growth in a Ramos model.
Figure 12B:
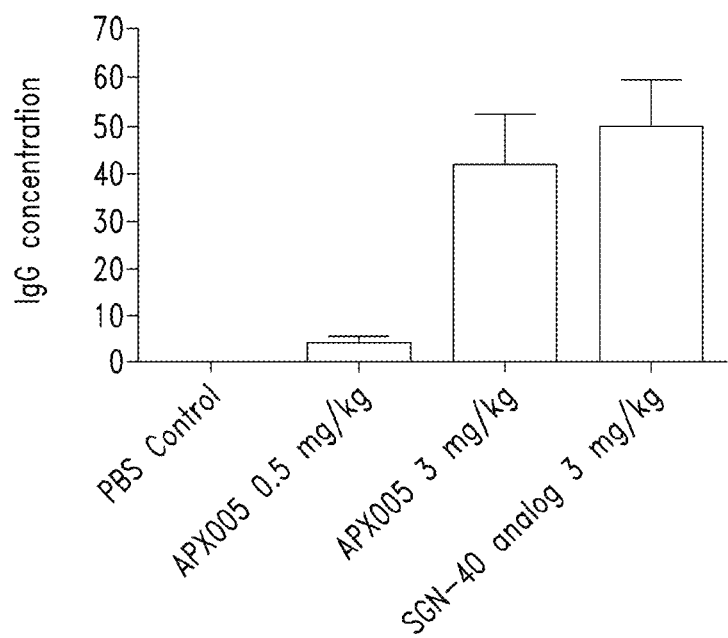
FIG. 12B is a bar graph showing levels of serum human IgG in mice at day 34, two days after the last dosing.

In order to evaluate the effect of APX005 on the xenograft model of human B cell lymphoma, female BALB/c nu/nu mice 6-8 weeks of age were used for tumor cell inoculation. Xenografts were established by subcutaneous inoculation of $1 \times 10^7$ tumor cells/mouse into the dorsal flanks. When tumors reached an average volume of about 100 mm$^3$ (50-200 mm$^3$), the animals were randomized into groups. Antibodies were administered intraperitoneally at 3 mg/kg starting at day 13 (see FIG. 12). Dosing was administered 3 times per week for a total of 9 doses (eight animals per group). Perpendicular dimensions of the tumor were measured using a Vernier scale caliper. Tumor volumes were calculated using the formula: Volume=(length×width$^2$)/2. As shown in FIG. 12A, APX005 demonstrated potent and long-lasting anti-tumor activity. Serum was taken at day 34, two days after the last dosing, for determining in vivo drug levels by measuring human IgG concentrations (see FIG. 12B). The anti-tumor efficacy mediated by APX005 was greater than that of SGN-40 and persisted long after the dosing period. Single point PK analysis showed that the superior anti-tumor activity of APX005 was not due to PK difference.

APX005 Inhibition of Rituximab Pre-Treated and Resistant Tumors

Figure 13A:
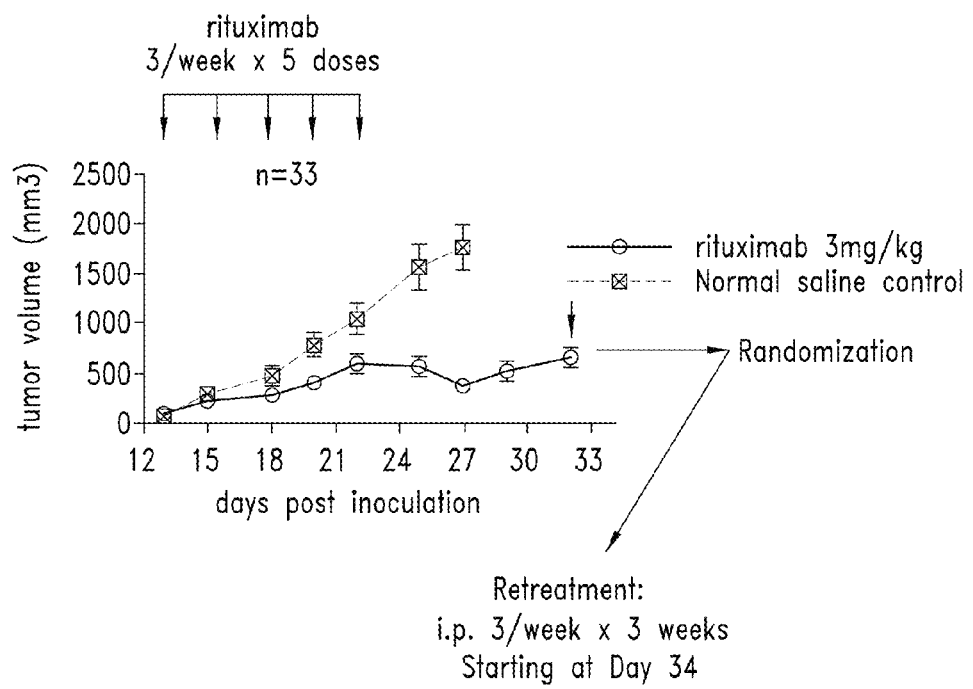
FIGS. 13A and 13B are graphs showing inhibition of Rituximab pre-treated and resistant tumors in a mouse model.
Figure 13B:
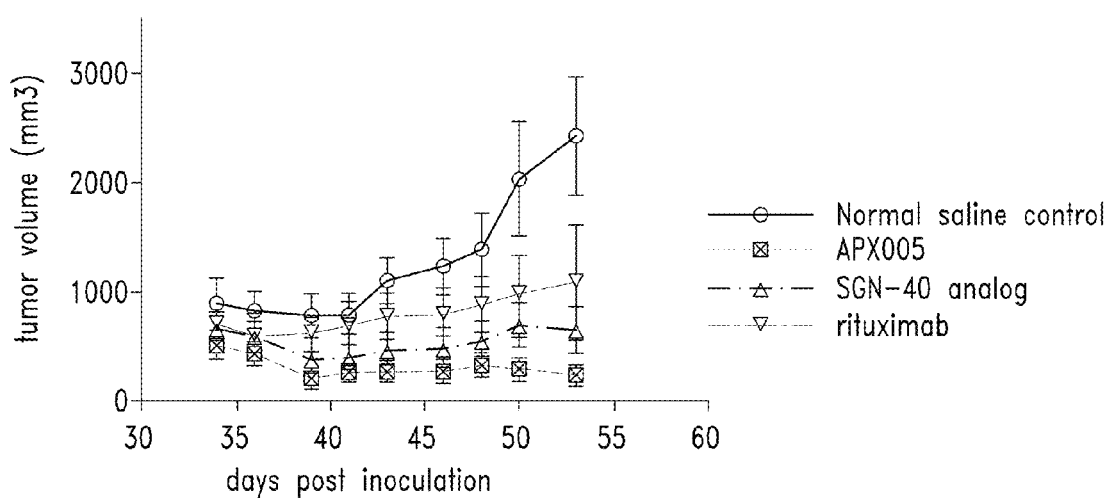

The purpose of this experiment was to evaluate the effect of APX005 on rituximab pre-treated and resistant B cell lymphoma. Nude mice bearing established Ramos tumors were first treated with rituximab at 3 mg/kg for 5 doses. Tumor growth was partially inhibited by rituximab (FIG. 13A). When these tumors reached size about 700 mm$^3$, they were randomized into 4 groups (7 animals per group) and re-treated i.p. with APX005, rituximab, SGN40 analog 3 mg/kg or saline control for 3 weeks (FIG. 13B). As shown in FIG. 13, rituximab pre-treated tumors failed to respond to rituximab re-treatment, suggesting that these tumors are rituximab resistant (FIG. 13B). APX005 exhibited the capability of inhibiting the growth of rituximab resistant tumors.

APX005 Inhibition of Tumor Growth in the Raji Model

Figure 14:
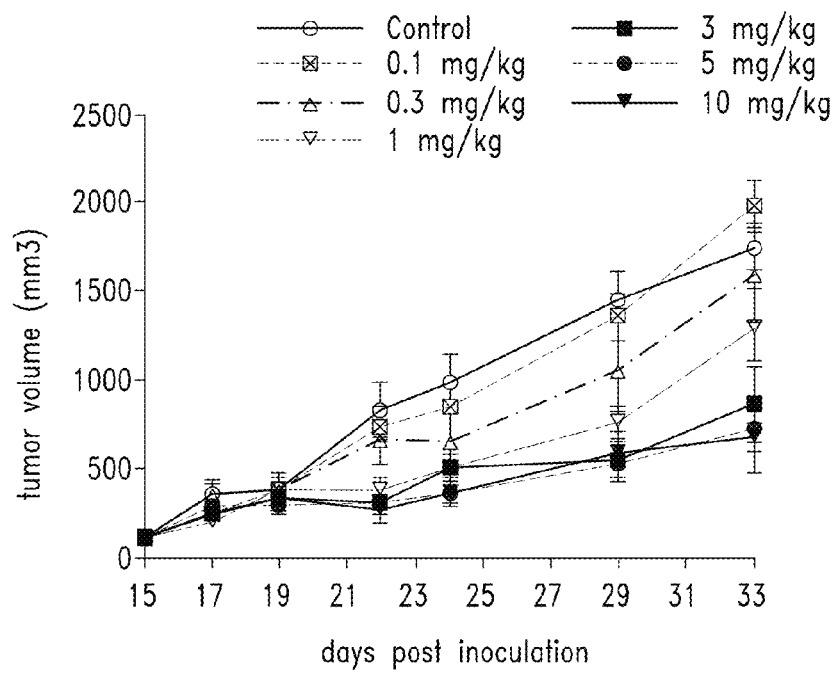
FIG. 14 is a graph showing APX005 inhibition of tumor growth in the Raji mouse model.

The purpose of this experiment was to determine the dose and efficacy relationship of APX005 in vivo. Nude mice bearing established CD40 positive Raji tumors were treated with APX005 starting at day 15. Doses of APX005 ranging from 0.1 mg/kg-10 mg/kg were administered i.p. 3 times/week for 2 weeks (eight animals per group) (see FIG. 14). Saline was used as control treatment. Tumor volumes were measured on each dosing day. Serum levels of APX005 in each group were also measured 3 days after last dosing to determine the correlation of the in vivo efficacy with the levels of APX005 in the circulation. Clear dose-dependent anti-tumor activity was observed (see FIG. 14). Differences in tumor volumes were significant (P≤0.05) between the control group and antibody treatment groups with dose levels ≥1 mg/kg on days 29 to 33. The minimal effective dose was determined as 1 mg/kg, which corresponded to a median serum concentration of 0.49 µg/ml at day 36. Differences in tumor volumes between the 3, 5 and 10 mg/kg dose groups were not statistically significant. Thus, the maximal anti-tumor activity was achieved at doses ≥3 mg/kg with a median serum concentration ≥1.6 µg/ml.

Inhibition of Tumor Growth in Human MM IM-9 Model by APX005

In order to evaluate the anti-tumor activity of APX005 in human multiple myeloma model, nude mice bearing established CD40 positive multiple myeloma IM-9 tumors were treated i.p. with APX005 or SGN40 starting at day 15. APX005 was given at 3 mg/kg, 3 times/week for 3 weeks (5 animals per group). Tumor volumes were measured on each dosing day.

Figure 15:
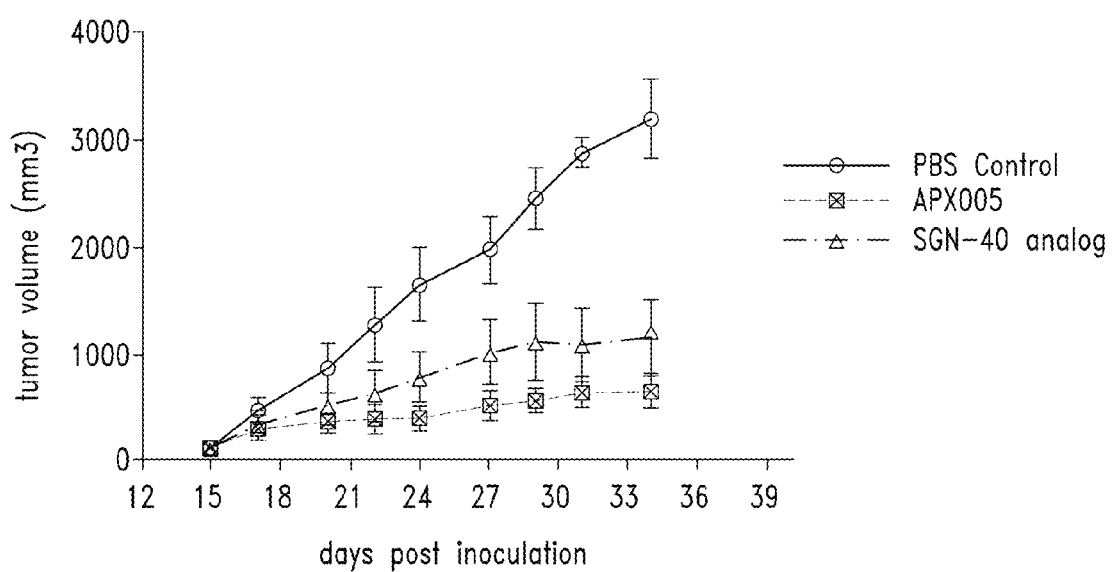
FIG. 15 is a graph showing potent anti-tumor activity of APX005 against human multiple myeloma in the IM-9 xenograft model.

APX005 demonstrated potent anti-tumor activity against human multiple myeloma in the IM-9 xenograft model (see FIG. 15). The anti-tumor efficacy mediated by APX005 was significantly greater than that of SGN-40 (P<0.05).

Inhibition of Tumor Growth in the Ramos Model by APX005 as Compared with SGN-40 and Rituximab The purpose of this experiment was to compare the anti-tumor activity of APX005, rituximab and SGN-40 in a human B cell lymphoma Ramos xenograft model. Xenografts were established by subcutaneous inoculation of Ramos cells into the dorsal flanks of female SCID C.B −17 mice. When tumors reached an average volume of about 200-300 mm$^3$, the animals were randomized into 6 groups. Antibodies were administered intraperitoneally at doses as indicated in FIG. 17. Dosing was administered 3 times per week for a total of 9 doses (10 animals per group). Perpendicular dimensions of the tumor were measured using a Vernier scale caliper. Tumor volumes were calculated using the formula: Volume=(length×width$^2$)/2. Survival of the mice was also determined and recorded.

Figure 17A:
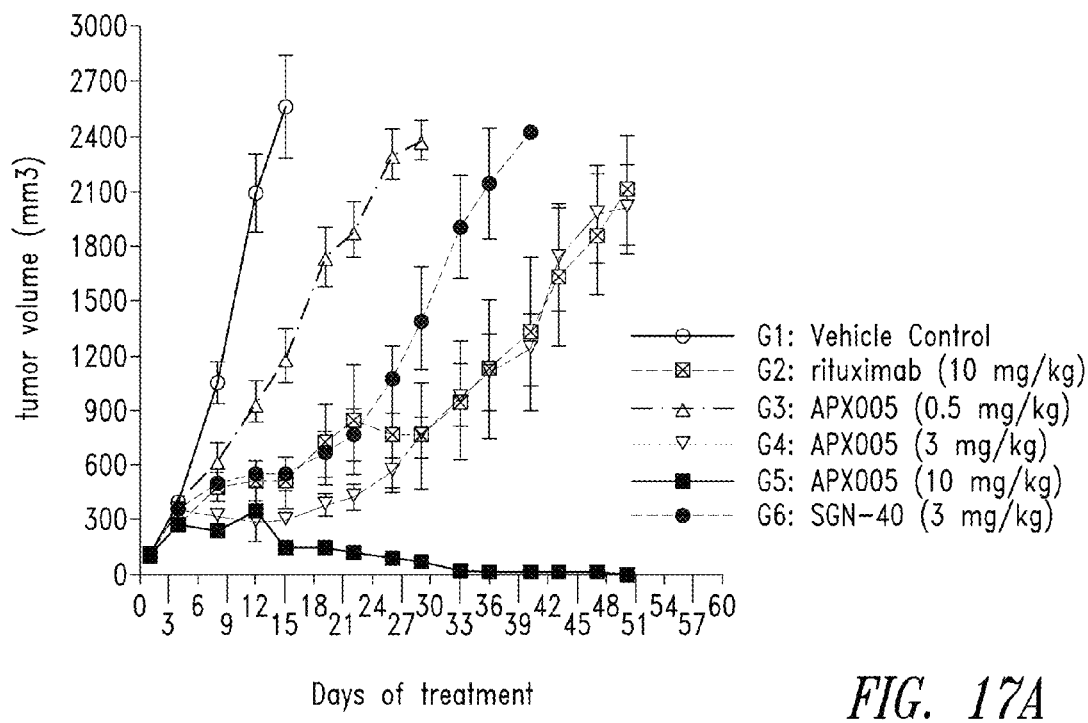
FIGS. 17A and 17B show inhibition of tumor growth in the Ramos model by APX005 as compared with SGN-40 and rituximab.
Figure 17B:
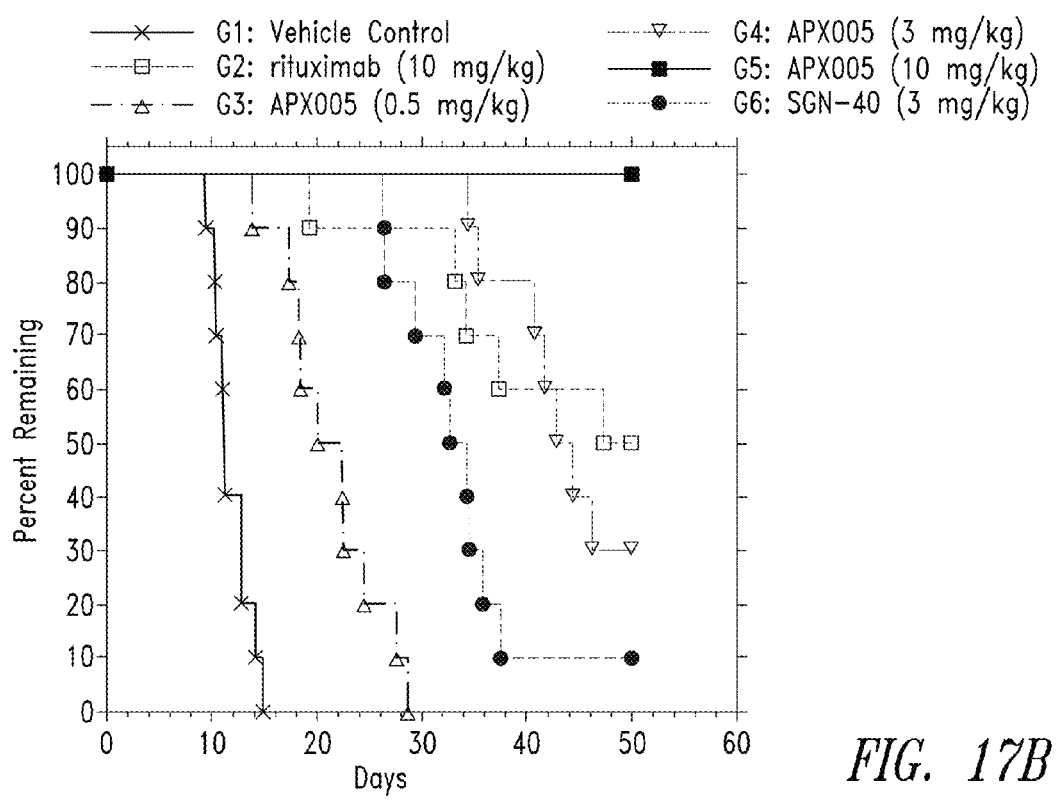

APX005 demonstrated dose-dependent anti-tumor activity. Treatment with the high dose of APX005 (10 mg/kg) resulted in complete tumor regression, while rituximab at the same dose (10 mg/kg) only delayed tumor growth, suggesting that APX005 is more efficacious than rituximab in this model. APX005 is also more potent than SGN-40 (FIG. 17A). APX005 not only inhibited tumor growth but also improved the survival of the tumor bearing animals (FIG. 17B).

Inhibition of Tumor Growth in a Rituximab-Resistant Human Namalwa Lymphoma Xenograft Model The purpose of this experiment was to compare the anti-tumor activity of APX005, rituximab and SGN-40 in the rituximab-resistant human Namalwa lymphoma model. Xenografts were established by subcutaneous inoculation of Namalwa cells into the dorsal flanks of female SCID C.B −17 mice. When tumors reached an average volume of about 200-300 mm3, the animals were randomized into 6 groups. Antibodies were administered i.p. at the doses indicated in FIG. 18. Dosing was administered 3 times per week for a total of 9 doses (10 animals per group). Perpendicular dimensions of the tumor were measured using a Vernier scale caliper. Tumor volumes were calculated using the formula: Volume=(length×width$^2$)/2. Survival of the mice was also determined and recorded.

Figure 18A:
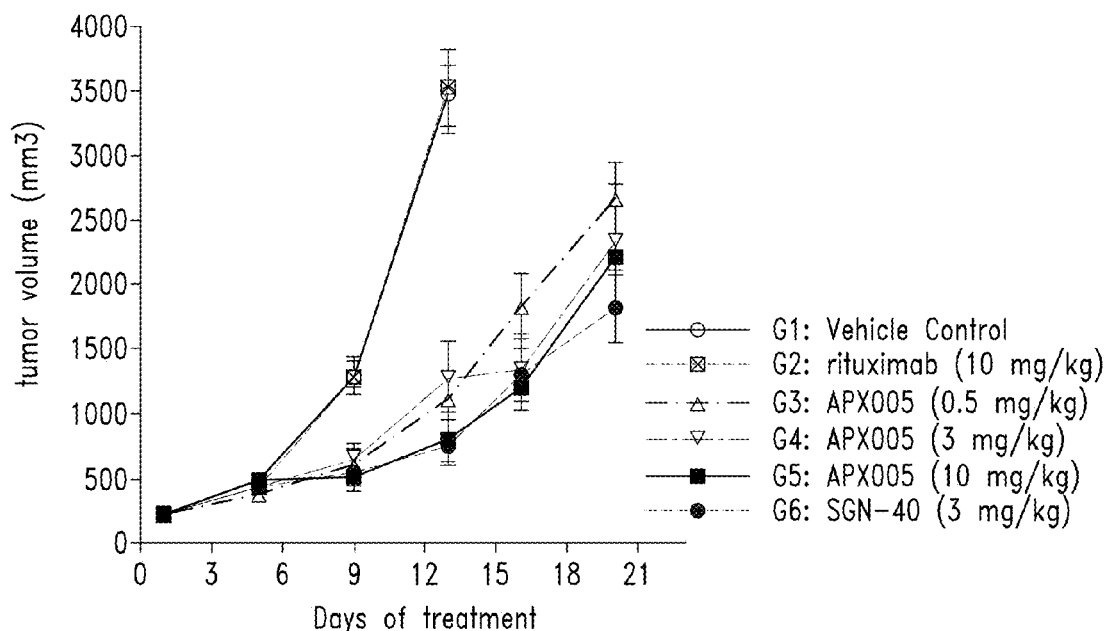
FIGS. 18A and 18B show inhibition by APX005 of tumor growth in rituximab-resistant human Namalwa lymphoma xenograft model.
Figure 18B:
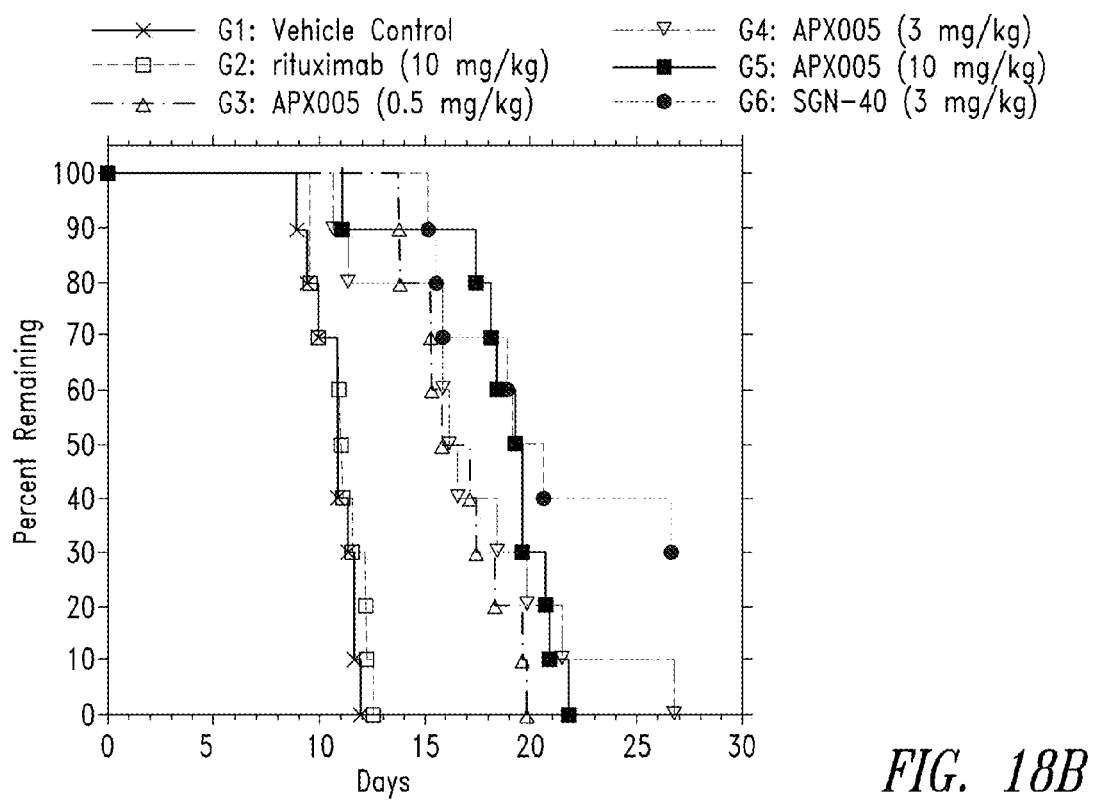

APX005 demonstrated potent anti-tumor activity in rituximab-resistant Namalwa lymphoma model (FIG. 18A). APX005 also improved the survival of mice bearing rituximab-resistant tumors (FIG. 18B).

In summary, the experiments in this Example showed that the efficacy of APX005 was examined in multiple xenograft tumor models. APX005 markedly inhibited the tumor growth in the Ramos model. Interestingly, the therapeutic effect persisted far beyond the dosing period. APX005 treatment resulted in inhibition of rituximab pre-treated and resistant tumors. A dose-range finding study was performed in the Raji model and found that minimal effective dose was determined as 1 mg/kg, and the maximal anti-tumor activity was observed at doses ≥3 mg/kg. In addition to B-cell lymphoma, APX005 also exhibited significant potent anti-tumor activity in the human multiple myeloma IM-9 model.

Thus, the above Examples demonstrate that APX005 can be used to improve the treatment of patients with NHL, CLL, multiple myeloma and certain solid tumors that express the CD40 target. Upon binding to CD40, APX005 recruits cytotoxic cells to kill tumor cells via ADCC. APX005 can also directly inhibit tumor cell proliferation and activate APC via its agonist activity. In vivo, APX005 markedly inhibited the growth of multiple CD40-expressing human tumor xenografts and showed long-lasting anti-tumor effects. APX005 is also capable of inhibiting human multiple myeloma and rituximab pre-treated and resistant tumors.

Example 4

APX005 S267E Fc Mutant Increases Binding to FcγRIIB and CD40 Agonist Activity

In an effort to increase binding to Fcγ receptor and to increase the agonist activity of the APX005 antibody, the serine (S) at residue 267 of APX005 Fc (IgG1, EU numbering) was mutated to glutamic acid (E) to generate the APX005 S267E mutant. The mutation from AGC (S) to GAG (E) at position 267 located at APX005 heavy chain Fc region was confirmed by sequencing. The IgG1 heavy chain constant region comprising the modified Fc region sequence is provided in SEQ ID NO:195 (this sequence includes CH1, hinge, CH2 and CH3 of IgG1).

Figure 19:
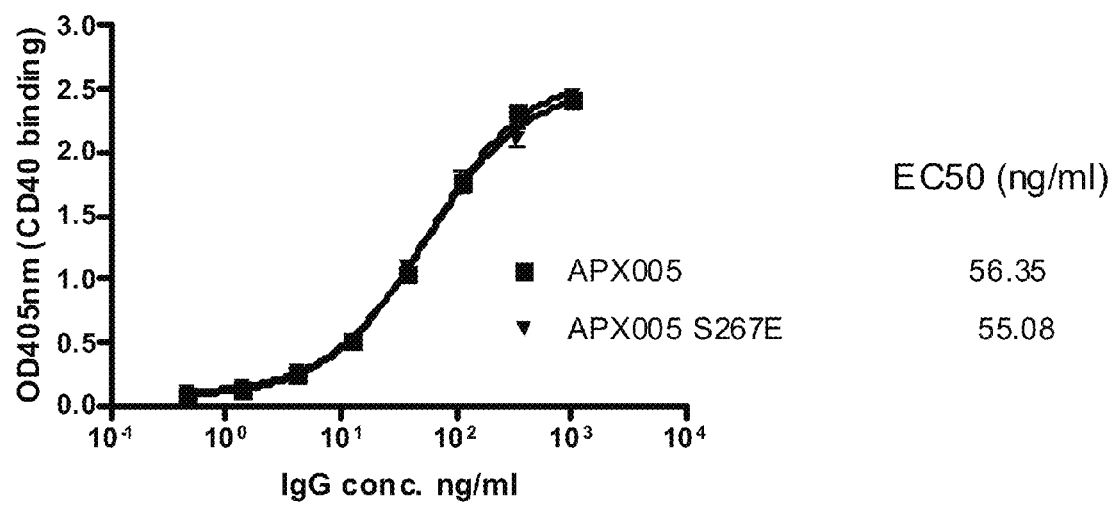
FIG. 19 shows a comparison of APX005 and APX005S267E binding to CD40.

In order to assess the ability of the APX005 S276E mutant to bind to CD40, APX005 S267E heavy chain and light chain plasmids were purified from transformed bacteria and transfected into 293-6E cell. Four days after transfection, antibody-containing culture supernatants were collected and tested for binding to CD40 using ELISA (ELISA plates coated with CD40-Fc protein). The ELISA data showed that APX005 S267E mutant had similar binding activity as APX005 to CD40 (see FIG. 19).

Figure 20:
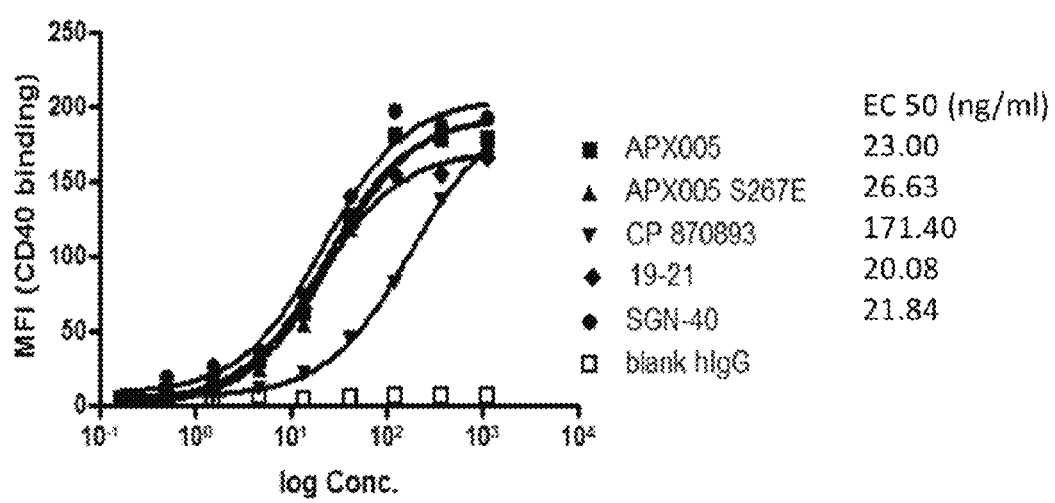
FIG. 20 shows binding affinity of APX005 and APX005 S267E mutant as compared with other anti-CD40 antibodies.

In another experiment, the ability of the CD40 antibodies to bind to native CD40 protein was determined by FACS analysis with live Ramos cells. Ramos cells were harvested and blocked with 1.5 ml blocking buffer (0.1% BSA/PBS) for 30 minutes. Antibodies at various concentrations were added to cells and incubated for 1 hour. After washing, 50 ul Goat-anti-human IgG (H+L) PE antibody at 1:1000 dilution in blocking solution was added and incubated for 30 minutes. Cells were then washed with PBS and were re-suspended with 1 m PBS and analyzed by FACS. The antibodies tested were the 19-21 rabbit anti-CD40 agonist antibody, SGN-40 developed by Seattle Genetics and CP870893 from Pfizer. As shown in FIG. 20, APX005 and APX005 S267E mutant showed similar binding affinity to CD40 as SGN40, but 6 fold higher affinity than CP870893.

Figure 21:
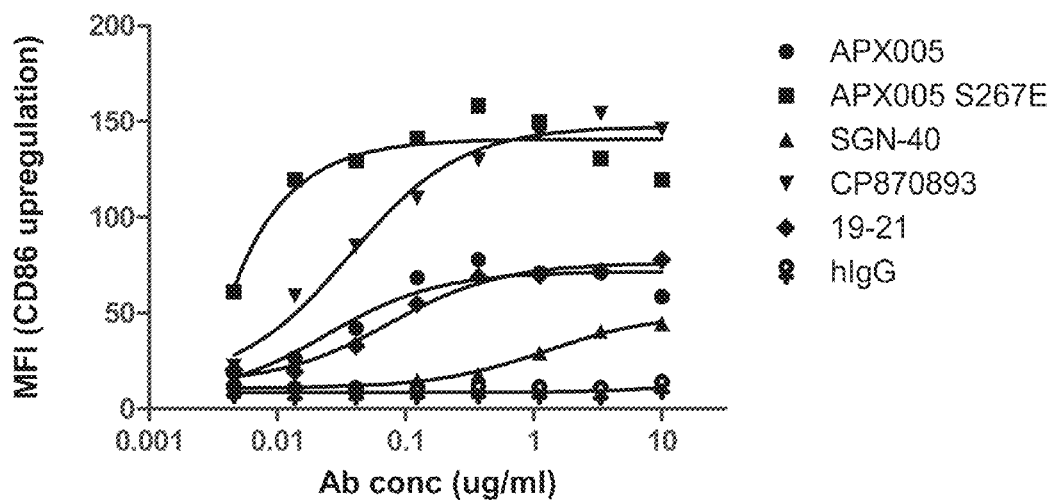
FIG. 21 shows CD40 agonist activity of APX005 S267E mutant. The EC50 (ng/ml) for this experiment was as follows: APX005: 24.35; APX005 S267E: 4.15; SGN-40: 1264.00; CP870893: 37.00; 19-21: 74.65.

An experiment was performed to compare the CD40 agonist activity of APX005, APX005 S267E mutant, and other anti-CD40 antibodies in a B cell activation assay. In particular, CD40 agonist activity was tested by measuring the up-regulation of CD86, a B cell activation marker, on human B cells following treatment with various anti-CD40 antibodies in vitro. Fresh human B cells were obtained by isolating B cell from peripheral blood using a negative selection method (All Cells). B cells were treated with different human antibodies at 10, 3.33, 1.11, 0.37, 0.12, 0.04, 0.01 and 0.0045 µg/ml for 48 hours. The cells were then collected and analyzed for human CD86 expression on live B cells by flow cytometry. 19-21, SGN-40 and CP870893 (see description above) were tested. As shown in FIG. 21, APX005 S267E mutant demonstrated significantly increased potency (EC50) and efficacy (EC100) as compared to APX005. APX005 S267E was the most potent CD40 agonist antibody among the anti-CD40 antibodies tested in this assay.

Figure 22:
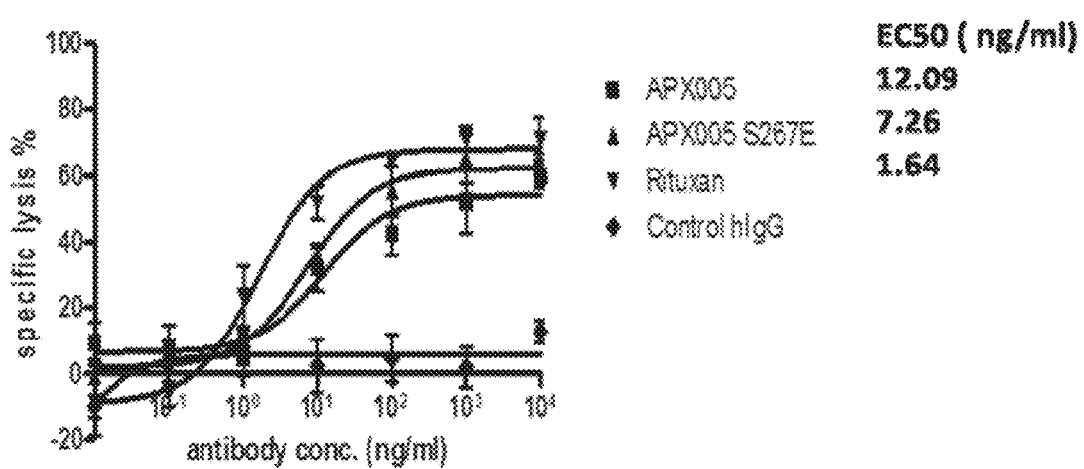
FIG. 22 shows ADCC activity of the APX005 S267E mutant.

A further experiment was conducted to assess the ADCC activity of APX005 and APX005 S267E mutant. Specifically, the ability of the CD40 antibodies to mediate ADCC effects in vitro was assayed using Daudi cells as target cells and human PBMC as effector cells. Labeled target cells were plated in triplicates at 5×10$^3$ cells/well in round-bottomed 96 well plates. Increasing concentration of antibodies (50 ul/well in complete medium) was added to the labeled cells. The final antibody concentration ranged from 0-10 ug/ml (in complete medium). The cells were treated with the antibodies for 30 minutes at 37° C. Effector cells (PBMC) in complete medium were seeded into target cells, (Effector Cells/Target Cell ratio=40/1). Final volume of effector cells is 100 ul/well. After 4 hours incubation in a 37° C. incubator, 100 ul culture supernatant from each well was transferred to a 96-well black view plate and read RFU with 485 ex/535 em. Specific lysis was calculated according to the formula: Specific lysis=[(test release−spontaneous release)/(maximum release−spontaneous release)]×100. Rituxan was used as positive control. As shown in FIG. 22, the APX005 S267E mutant showed slightly increased the ADCC activity as compared to APX005 wild type.

Example 5

Characterization of the Epitope of APX005

This example describes the characterization of the epitope of APX005, a humanized anti-CD40 antibody. As described in further detail below, a total of 5841 linear and Chemically Linked Peptides on Scaffolds (CLIPS™) peptides were synthesized and analyzed for binding. The dominant binding regions were identified as $_{92}$TSEACESCVLHRSCSP$_{107}$ (SEQ ID NO: 196) and $_{125}$PCPVGFFSNVS-SAFEKCHPW$_{144}$ (SEQ ID NO: 197). Of the identified binding residues, T$_{92}$, E$_{97}$ and $_{100}$VL$_{101}$ are known as being contact residues between CD40 and the CD40L trimer. Specifically E$_{97}$ is considered an import residue for binding of CD40 to the ligand.

The CD40 protein sequence is set forth in SEQ ID NO: 198, and is directly available as a single crystal structure: 3QD6. Residues of CD40 predicted to bind to the CD40L trimer are E74, Y82, D84, N86 and E117 (see e.g., Bajorath et al., 1995 Biochemistry 34:9884-9892)) It should be noted that the sequence numbering in the 3QD6 structure is 20 residues higher than the numbers mentioned herein. Thus, the predicted key binding residues are E54, Y62, D64, N66 and E97.

Synthesis of Peptides and Screening Procedures.

To reconstruct discontinuous epitopes of the target molecule a library of structured peptides was synthesized. This was done using Pepscan's proprietary Chemically Linked Peptides on Scaffolds (CLIPS™) technology (Pepscan Presto, Lelystad The Netherlands) (see e.g., Timmerman et al. (2007). *J. Mol. Recognit.* 20:283-99; Slootstra et al. (1996). *Molecular Diversity* 1: 87-96). CLIPS™ technology provides the ability to structure peptides into single loops, double-loops, triple loops, sheet-like folds, helix-like folds and combinations thereof. CLIPS™ templates are coupled to cysteine residues. For this experiment, the side-chains of multiple cysteines in the peptides were coupled to one or two CLIPS™ templates. For example, a 0.5 mM solution of the T2 CLIPS™ template 1,3-bis (bromomethyl) benzene was dissolved in ammonium bicarbonate (20 mM, pH 7.9)/acetonitrile (1:1(v/v). This solution was added onto the peptide arrays. The CLIPS template binds to side-chains of two cysteines as present in the solid-phase bound peptides of the peptide-arrays (455 wells plate with 3 ul wells). The peptide arrays were gently shaken in the solution for 30 to 60 minutes while completely covered in solution. Finally, the peptide arrays were washed extensively with excess of $H_2O$ and sonicated in disrupt-buffer containing 1 percent SDS/0.1 percent beta-mercaptoethanol in PBS (pH 7.2) at 70° C. for 30 minutes, followed by sonication in $H_2O$ for another 45 minutes. The T3 CLIPS™ carrying peptides were made in a similar way but with three cysteines.

The binding of antibody to each of the synthesized peptides was tested in a PEPSCAN-based ELISA. The peptide arrays were incubated with primary antibody solution (overnight at 4° C.). After washing, the peptide arrays were incubated with a 1/1000 dilution of an antibody peroxidase conjugate (SBA, cat.nr.2010-05) for one hour at 25° C. After washing, the peroxidase substrate 2,2'-azino-di-3-ethylbenzthiazoline sulfonate (ABTS) and 2 microliters/milliliter of 3 percent $H_2O_2$ were added. After one hour, the color development was measured. The color development was quantified with a charge coupled device (CCD)-camera and an image processing system.

Data Processing

The values obtained from the CCD camera range from 0 to 3000 mAU, similar to a standard 96-well plate ELISA-reader. The results were quantified and stored into the Peplab database. The binding values were extracted for analysis. Occasionally a well contained an air-bubble resulting in a false-positive value. The cards were manually inspected and any values caused by an air-bubble were scored as 0.

The determination of the epitopes was conducted through a combination of 20-mer overlapping peptides and single-residue mutagenesis of 12 specific areas of the protein. These 12 areas were picked based on the known 3D structure of CD40 and on published cysteine bonds in the protein. A total of 5841 chemically synthesized CLIPS™ peptides were synthesized.

Evaluation of the overlapping 20-mer peptides indicated two distinct binding regions: $_{92}$TSEACESCVLHRSCSP$_{107}$ (SEQ ID NO: 196) and $_{125}$PCPVGFFSNVS-SAFEKCHPW$_{144}$ (SEQ ID NO: 197). Evaluation of the overlapping sequences in which two alanine-replacements were added gave similar results.

The 12 candidate epitope "hotspots" that were elected each contain at least 10 identical 'control' peptides in which no mutation is made. Evaluation of these control sequences for each of the 12 mutagenesis data sets identified two similar distinct binding regions: $_{84}$TCEEGWHCTSEAC-ESCVLH$_{102}$ (SEQ ID NO: 199) and $_{125}$PCPVGFFSNVS-SAFEKCHPW$_{144}$ (SEQ ID NO: 197). The obtained ELISA read-outs are statistically highly significant ($p<2e^{-10}$). Considering the overlap of $_{92}$TSEACESCVLHRSCSP$_{107}$ (SEQ ID NO: 196) and $_{84}$TCEEGWHCTSEACESCVLH$_{102}$, (SEQ ID NO: 199) residues 92-102 (SEQ ID NO:202) are possibly the most relevant residues for binding. Data from the CLIPS™ matrix set combining three different sequence areas to identify discontinuous epitopes did not yield additional insights.

In-depth analysis of the 2 mutagenesis datasets ($_{84}$TCEEGWHCTSEACESCVLH$_{102}$ (SEQ ID NO: 199) and $_{125}$PCPVGFFSNVSSAFEKCHPW$_{144}$ (SEQ ID NO: 197) did not indicate any critical residues, with the possible exception of W144. However, mutagenesis of residues 84-102 was also conducted on the linear peptide, without CLIPS™ (sequence $_{84}$TCEEGWHSTSEASESCVLH$_{102}$ (SEQ ID NO:200), the two underlined residues are replaced from C to S). In this linearized peptide binding by APX005 almost completely disappeared, indicating that the binding of this antibody depends specifically on those two cysteines, or depends on the specific conformational state the peptide was forced into by the CLIPS™ assembly.

Figure 23A:
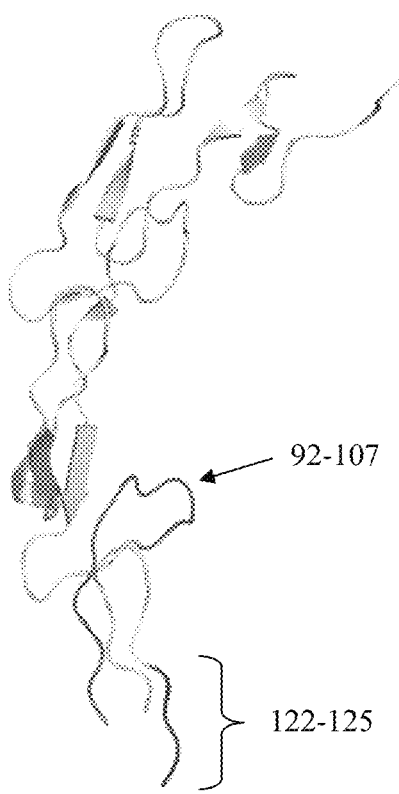
FIGS. 23A and 23B show the visualization of the APX005 epitopes on the cartoon rendering (FIG. 23A) and surface rendering (FIG. 23B) of the CD40 structure 3QD6. The epitope area 92TSEACESCVLHRSCSP$_{107}$ (SEQ ID NO: 196) is mapped onto the crystal structure of CD40 and is outlined in bold. Residues 125-144, which were also found to be bound by the APX005 antibody, are not resolved in structure 3QD6, but based on the available data on cysteine bonds, are expected to be in close proximity to residues 92-107. Therefore, for reference and visualization purposes, residues 122-125 (SEQ ID NO:201) are shown.
Figure 23B:
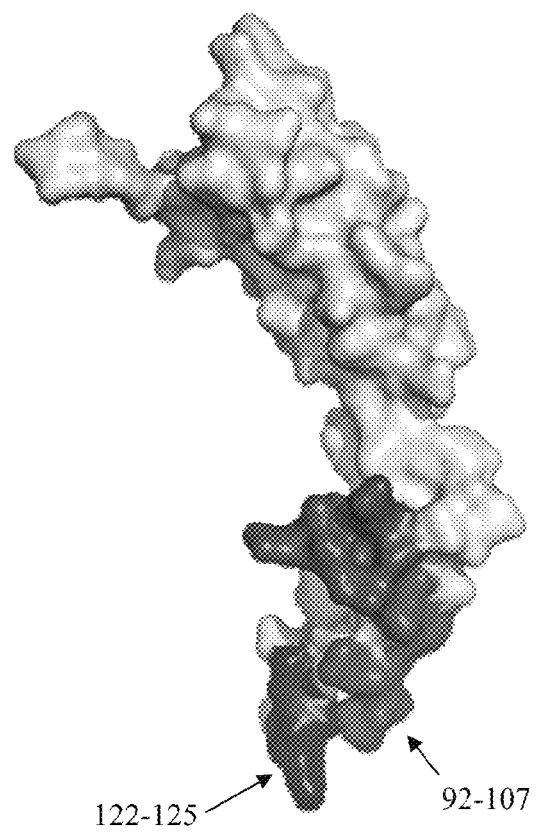

Visualization of areas $_{92}$TSEACESCVLHRSCSP$_{107}$ (SEQ ID NO: 196) and $_{125}$PCPVGFFSNVS-SAFEKCHPW$_{144}$ (SEQ ID NO: 197) onto the crystal structure of CD40 showed that amino acids 92-107 forms a looped structure facing the CD40L-trimer ($_{97}$ESC$_{100}$ is within 4A of the ligand) (see FIGS. 23A and 23B). Residues 125-144 are not resolved in structure 3QD6, but based on the available data on cysteine bonds, are expected to be in close proximity to residues 92-107. For visualization purposes, residues 122-125 (SEQ ID NO:201) are shown in FIGS. 23A and 23B.

Thus, this experiment describes the mapping of the binding of humanized antibody APX005 onto CD40 using linear and CLIPS™ peptides, carried out by Pepscan Presto BV. The mapping resulted in the identification of two specific binding regions. These are $_{92}$TSEACESCVLHRSCSP$_{107}$ (SEQ ID NO:196) and $_{125}$PCPVGFFSNVS-SAFEKCHPW$_{144}$ (SEQ ID NO:197). Within region 92-107, residues $_{92}$TSEACESCVLH$_{102}$ (SEQ ID NO:202) are possibly the most relevant residues for binding. Of the identified binding residues, $T_{92}$, $E_{97}$ and $_{100}VL_{101}$ are known as being contact residues between CD40 and the CD40L trimer. Specifically $E_{97}$ is considered an import residue binding of CD40 to the ligand.

The various embodiments described above can be combined to provide further embodiments. All of the U.S. patents, U.S. patent application publications, U.S. patent application, foreign patents, foreign patent application and non-patent publications referred to in this specification and/or listed in the Application Data Sheet are incorporated herein by reference, in their entirety. Aspects of the embodiments can be modified, if necessary to employ concepts of the various patents, application and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. An isolated antibody, or antigen-binding fragment thereof, that binds to CD40, wherein the isolated antibody, or an antigen-binding fragment thereof, comprises (i) a heavy chain variable region comprising the VHCDR1 region set forth in SEQ ID NO:3, the VHCDR2 region set forth in SEQ ID NO:4, and the VHCDR3 region set forth SEQ ID NO:5; and (ii) a light chain variable region comprising the VLCDR1 region set forth in SEQ ID NO:6, the VLCDR2 region set forth in SEQ ID NO:7, and the VLCDR3 region set forth in SEQ ID NO: 8; further comprising an Fc region modified by a S267E mutation.

2. The isolated antibody of claim 1, wherein the antibody is humanized.

3. The isolated antibody of claim 1 wherein the antibody is selected from the group consisting of a single chain antibody and a univalent antibody lacking a hinge region.

4. The isolated antibody of claim 1 wherein the antibody is a whole antibody.

5. The isolated antibody of claim 1 comprising a human IgG constant domain.

6. The isolated antibody of claim 5 wherein the IgG constant domain comprises an IgG1 CH1 domain.

7. The isolated antibody of claim 5 wherein the IgG constant domain comprises an IgG1 Fc region.

8. The isolated antibody, or an antigen-binding fragment thereof, of claim 1 that competes with an antibody comprising the VH region set forth in SEQ ID NO:1 and the VL region set forth in SEQ ID NO:2 for binding to CD40.

9. A composition comprising a physiologically acceptable carrier and a therapeutically effective amount of the isolated antibody or antigen-binding fragment thereof according to claim 1.

* * * * *

SEQUENCE LISTING

<160> NUMBER OF SEQ ID NOS: 205

<210> SEQ ID NO 1
<211> LENGTH: 137
<212> TYPE: PRT
<213> ORGANISM: Oryctolagus cuniculus

<400> SEQUENCE: 1

Met Glu Thr Gly Leu Arg Gly Leu Leu Val Ala Val Leu Lys Gly
1               5                   10                  15

Val Gln Cys Gln Ser Leu Glu Glu Ser Gly Gly Asp Leu Val Lys Pro
            20                  25                  30

Gly Ala Ser Leu Thr Leu Thr Cys Thr Ala Ser Gly Phe Ser Phe Ser
        35                  40                  45

Ser Thr Tyr Val Cys Trp Val Arg Gln Ala Pro Gly Lys Gly Leu Glu
    50                  55                  60

Trp Ile Ala Cys Ile Tyr Thr Gly Asp Gly Thr Asn Tyr Ser Ala Ser
65                  70                  75                  80

Trp Ala Lys Gly Arg Phe Thr Ile Ser Lys Pro Ser Ser Thr Thr Val
                85                  90                  95

Thr Leu Gln Met Thr Ser Leu Thr Pro Ala Asp Thr Ala Thr Tyr Phe
            100                 105                 110

Cys Ala Arg Pro Asp Ile Thr Tyr Gly Phe Ala Ile Asn Phe Trp Gly
        115                 120                 125

Pro Gly Thr Leu Val Thr Val Ser Ser
    130                 135

<210> SEQ ID NO 2
<211> LENGTH: 131
<212> TYPE: PRT
<213> ORGANISM: Oryctolagus cuniculus

<400> SEQUENCE: 2

Met Asp Thr Arg Ala Pro Thr Gln Leu Leu Gly Leu Leu Leu Leu Trp
1               5                   10                  15

Leu Pro Gly Ala Arg Ser Ala Asp Ile Val Met Thr Gln Thr Pro Ser
            20                  25                  30

Ser Ala Ser Glu Pro Val Gly Gly Thr Val Thr Ile Lys Cys Gln Ala
        35                  40                  45

Ser Gln Ser Ile Ser Ser Arg Leu Ala Trp Tyr Gln Gln Lys Pro Gly
    50                  55                  60

Gln Pro Pro Lys Leu Leu Ile Tyr Arg Ala Ser Thr Leu Ala Ser Gly
65                  70                  75                  80

Val Pro Ser Arg Phe Lys Gly Ser Gly Ser Gly Thr Glu Phe Thr Leu
                85                  90                  95

Thr Ile Ser Asp Leu Glu Cys Ala Asp Ala Ala Thr Tyr Tyr Cys Gln
            100                 105                 110

Cys Thr Gly Tyr Gly Ile Ser Trp Pro Ile Gly Gly Gly Thr Glu Val
        115                 120                 125

Val Val Lys
    130

<210> SEQ ID NO 3
<211> LENGTH: 10
<212> TYPE: PRT
<213> ORGANISM: Oryctolagus cuniculus

<400> SEQUENCE: 3

-continued

Gly Phe Ser Phe Ser Ser Thr Tyr Val Cys
1               5                   10

<210> SEQ ID NO 4
<211> LENGTH: 17
<212> TYPE: PRT
<213> ORGANISM: Oryctolagus cuniculus

<400> SEQUENCE: 4

Cys Ile Tyr Thr Gly Asp Gly Thr Asn Tyr Ser Ala Ser Trp Ala Lys
1               5                   10                  15
Gly

<210> SEQ ID NO 5
<211> LENGTH: 11
<212> TYPE: PRT
<213> ORGANISM: Oryctolagus cuniculus

<400> SEQUENCE: 5

Pro Asp Ile Thr Tyr Gly Phe Ala Ile Asn Phe
1               5                   10

<210> SEQ ID NO 6
<211> LENGTH: 11
<212> TYPE: PRT
<213> ORGANISM: Oryctolagus cuniculus

<400> SEQUENCE: 6

Gln Ala Ser Gln Ser Ile Ser Ser Arg Leu Ala
1               5                   10

<210> SEQ ID NO 7
<211> LENGTH: 7
<212> TYPE: PRT
<213> ORGANISM: Oryctolagus cuniculus

<400> SEQUENCE: 7

Arg Ala Ser Thr Leu Ala Ser
1               5

<210> SEQ ID NO 8
<211> LENGTH: 10
<212> TYPE: PRT
<213> ORGANISM: Oryctolagus cuniculus

<400> SEQUENCE: 8

Gln Cys Thr Gly Tyr Gly Ile Ser Trp Pro
1               5                   10

<210> SEQ ID NO 9
<211> LENGTH: 120
<212> TYPE: PRT
<213> ORGANISM: Artificial Sequence
<220> FEATURE:
<223> OTHER INFORMATION: VH region of APX005, the humanized version of
      the R-8 rabbit anti-CD40 antibody

<400> SEQUENCE: 9

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Ser Thr
            20                  25                  30

Tyr Val Cys Trp Val Arg Gln Ala Pro Gly Lys Gly Leu Glu Trp Ile

```
                35                  40                  45
Ala Cys Ile Tyr Thr Gly Asp Gly Thr Asn Tyr Ser Ala Ser Trp Ala
         50                  55                  60
Lys Gly Arg Phe Thr Ile Ser Lys Asp Ser Ser Lys Asn Thr Val Tyr
 65                  70                  75                  80
Leu Gln Met Asn Ser Leu Arg Ala Glu Asp Thr Ala Val Tyr Phe Cys
                 85                  90                  95
Ala Arg Pro Asp Ile Thr Tyr Gly Phe Ala Ile Asn Phe Trp Gly Pro
            100                 105                 110
Gly Thr Leu Val Thr Val Ser Ser
        115                 120

<210> SEQ ID NO 10
<211> LENGTH: 130
<212> TYPE: PRT
<213> ORGANISM: Artificial Sequence
<220> FEATURE:
<223> OTHER INFORMATION: VL region of APX005, the humanized version of
      the R-8 rabbit anti-CD40 antibody

<400> SEQUENCE: 10

Met Asp Met Arg Val Pro Ala Gln Leu Leu Gly Leu Leu Leu Leu Trp
 1               5                  10                  15
Leu Arg Gly Ala Arg Cys Asp Ile Gln Met Thr Gln Ser Pro Ser Ser
             20                  25                  30
Leu Ser Ala Ser Val Gly Asp Arg Val Thr Ile Lys Cys Gln Ala Ser
         35                  40                  45
Gln Ser Ile Ser Ser Arg Leu Ala Trp Tyr Gln Gln Lys Pro Gly Lys
     50                  55                  60
Pro Pro Lys Leu Leu Ile Tyr Arg Ala Ser Thr Leu Ala Ser Gly Val
 65                  70                  75                  80
Pro Ser Arg Phe Ser Gly Ser Gly Ser Gly Thr Asp Phe Thr Leu Thr
                 85                  90                  95
Ile Ser Ser Leu Gln Pro Glu Asp Val Ala Thr Tyr Tyr Cys Gln Cys
            100                 105                 110
Thr Gly Tyr Gly Ile Ser Trp Pro Ile Gly Gly Gly Thr Lys Val Glu
        115                 120                 125
Ile Lys
    130

<210> SEQ ID NO 11
<211> LENGTH: 144
<212> TYPE: PRT
<213> ORGANISM: Oryctolagus cuniculus

<400> SEQUENCE: 11

Met Glu Thr Gly Leu Arg Trp Leu Leu Leu Val Ala Val Leu Lys Gly
 1               5                  10                  15
Val Gln Cys Gln Ser Leu Glu Glu Ser Gly Gly Asp Leu Val Lys Pro
             20                  25                  30
Gly Ala Ser Leu Thr Leu Thr Cys Thr Ala Ser Gly Phe Ser Phe Ser
         35                  40                  45
Asp Ser Phe Trp Ile Ala Trp Val Arg Gln Ala Pro Gly Lys Gly Leu
     50                  55                  60
Glu Trp Ile Gly Cys Ile His Ala Leu Ser Ser Gly Ser Thr Tyr Tyr
 65                  70                  75                  80
Ala Asn Trp Ala Arg Gly Arg Phe Thr Ile Ser Lys Thr Ser Ser Thr
```

```
                     85                  90                  95
Thr Val Thr Leu Gln Met Asn Ser Leu Thr Ala Ala Asp Thr Ala Thr
                100                 105                 110

Tyr Phe Cys Ala Arg Ser Tyr Ala Gly Tyr Ala Asp Tyr Asn Val Ala
            115                 120                 125

Thr Gly Leu Asn Leu Trp Gly Pro Gly Thr Leu Val Thr Val Ser Ser
        130                 135                 140

<210> SEQ ID NO 12
<211> LENGTH: 143
<212> TYPE: PRT
<213> ORGANISM: Oryctolagus cuniculus

<400> SEQUENCE: 12

Met Glu Thr Gly Leu Arg Trp Leu Leu Leu Val Ala Val Leu Lys Gly
1               5                   10                  15

Val Gln Cys Gln Glu Gln Leu Val Glu Ser Gly Gly Gly Leu Val Gln
            20                  25                  30

Pro Gly Gly Ser Leu Thr Leu Thr Gly Thr Ala Ser Gly Phe Ser Phe
        35                  40                  45

Ser Ser Ser Tyr Ser Met Cys Trp Val Arg Gln Ala Pro Gly Lys Gly
    50                  55                  60

Leu Glu Trp Ile Gly Cys Ile Asp Thr Gly Arg Gly Tyr Thr Tyr His
65                  70                  75                  80

Ala Ser Gly Ala Lys Gly Arg Phe Thr Phe Ser Lys Thr Ser Ser Thr
                85                  90                  95

Thr Val Thr Leu Gln Met Thr Ser Leu Thr Ala Ala Asp Thr Ala Thr
                100                 105                 110

Tyr Phe Cys Ala Arg Ser Ser Tyr Val Arg Tyr Asp Asn Arg Asn Tyr
            115                 120                 125

Gly Phe Asn Leu Trp Gly Pro Gly Thr Leu Val Thr Val Ser Ser
        130                 135                 140

<210> SEQ ID NO 13
<211> LENGTH: 138
<212> TYPE: PRT
<213> ORGANISM: Oryctolagus cuniculus

<400> SEQUENCE: 13

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Asp Leu Val Lys Pro
            20                  25                  30

Gly Ala Ser Leu Thr Leu Thr Cys Thr Ala Ser Arg Phe Ser Phe Ser
        35                  40                  45

Ser Thr Tyr Met Cys Trp Val Arg Gln Ala Pro Gly Lys Gly Leu Glu
    50                  55                  60

Trp Ile Ala Cys Thr Tyr Thr Gly Ser Ser Gly Gly Tyr Tyr Ala
65                  70                  75                  80

Ser Trp Ala Lys Gly Arg Phe Thr Ile Ser Gln Thr Ser Ser Thr Thr
                85                  90                  95

Val Thr Leu Gln Leu Thr Gly Leu Thr Pro Ala Asp Thr Ala Thr Tyr
                100                 105                 110

Phe Cys Ala Arg Pro Asp Val Gly Phe Asp Phe Ala Ile Asn Phe Trp
            115                 120                 125

Gly Pro Gly Thr Leu Val Thr Val Ser Ser
```

<210> SEQ ID NO 14
<211> LENGTH: 137
<212> TYPE: PRT
<213> ORGANISM: Oryctolagus cuniculus

<400> SEQUENCE: 14

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Leu Val Lys Pro
            20                  25                  30

Gly Gly Thr Leu Thr Leu Thr Cys Lys Ala Ser Gly Phe Ser Leu Asn
        35                  40                  45

Tyr Tyr Trp Pro Cys Trp Val Arg Gln Ala Pro Gly Lys Gly Leu Glu
    50                  55                  60

Trp Val Ala Cys Leu Asn Gly Gly Asp Ser Asp Thr Thr Val Tyr Ala
65                  70                  75                  80

Arg Trp Ala Lys Gly Arg Phe Thr Ile Ser Lys Ala Ser Ser Thr Thr
                85                  90                  95

Val Thr Leu Gln Met Thr Ser Leu Thr Ala Ala Asp Thr Ala Thr Tyr
            100                 105                 110

Phe Cys Ala Arg Tyr Ile Ile Pro Gly Tyr His Phe Asn Leu Trp Gly
        115                 120                 125

Pro Gly Thr Leu Val Thr Val Ser Ser
    130                 135

<210> SEQ ID NO 15
<211> LENGTH: 138
<212> TYPE: PRT
<213> ORGANISM: Oryctolagus cuniculus

<400> SEQUENCE: 15

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Asp Leu Val Lys Pro
            20                  25                  30

Gly Ala Ser Leu Thr Leu Thr Cys Thr Ala Ser Gly Ile Asp Phe Ser
        35                  40                  45

Ser Tyr Tyr Tyr Met Cys Trp Val Arg Gln Ala Pro Gly Lys Gly Leu
    50                  55                  60

Glu Trp Ile Gly Cys Ile Tyr Ala Gly Ser Gly Ser Thr Tyr Tyr Ala
65                  70                  75                  80

Ser Trp Ala Lys Gly Arg Phe Thr Ile Ser Lys Thr Ser Ser Thr Thr
                85                  90                  95

Val Thr Leu Gln Met Thr Ser Leu Thr Ala Ala Asp Thr Ala Thr Tyr
            100                 105                 110

Phe Cys Ala Arg Ser Gly Tyr Asn Asp Gly Ser Tyr Tyr Asn Leu Trp
        115                 120                 125

Gly Pro Gly Thr Leu Val Thr Val Ser Ser
    130                 135

<210> SEQ ID NO 16
<211> LENGTH: 141
<212> TYPE: PRT
<213> ORGANISM: Oryctolagus cuniculus

<400> SEQUENCE: 16

```
Met Glu Thr Gly Leu Arg Trp Leu Leu Leu Val Ala Val Leu Lys Gly
  1               5                  10                 15

Val Gln Cys Gln Ser Leu Glu Glu Ser Gly Gly Asp Leu Val Lys Pro
             20                  25                  30

Gly Ala Ser Leu Thr Leu Thr Cys Thr Ala Ser Gly Phe Ser Phe Ser
             35                  40                  45

Arg Gly Tyr Tyr Ile Cys Trp Val Arg Gln Ala Pro Gly Lys Gly Leu
         50                  55                  60

Glu Trp Ile Ala Cys Ile Gly Ala Gly Ser Gly Thr Tyr Phe Ala
 65              70                  75                  80

Ser Trp Ala Lys Gly Arg Phe Ser Ile Ser Arg Thr Ser Thr Thr
             85                  90                  95

Val Thr Leu Gln Met Thr Ser Leu Thr Ala Ala Asp Thr Ala Thr Tyr
             100                 105                 110

Phe Cys Ala Arg Glu Asp Ala Gly Asn Asp Asp Tyr Gly Tyr Ala Arg
             115                 120                 125

Asn Leu Trp Gly Pro Gly Thr Leu Val Thr Val Ser Ser
         130                 135                 140

<210> SEQ ID NO 17
<211> LENGTH: 138
<212> TYPE: PRT
<213> ORGANISM: Oryctolagus cuniculus

<400> SEQUENCE: 17

Met Glu Thr Gly Leu Arg Trp Leu Leu Leu Val Ala Val Leu Lys Gly
  1               5                  10                 15

Val Gln Cys Gln Ser Leu Glu Glu Ser Gly Gly Asp Leu Val Lys Pro
             20                  25                  30

Gly Ala Ser Leu Thr Leu Thr Cys Thr Ala Ser Gly Phe Ser Phe Ser
             35                  40                  45

Ser Ser Tyr Trp Ile Cys Trp Val Arg Gln Ala Pro Gly Lys Gly Leu
         50                  55                  60

Glu Trp Ile Ala Cys Ile Asn Thr Gly Ser Ser Val Thr Thr Val Tyr
 65              70                  75                  80

Ala Arg Trp Ala Lys Gly Arg Phe Thr Ile Ser Lys Ala Ser Ser Thr
             85                  90                  95

Thr Val Thr Leu Gln Met Thr Ser Leu Thr Ala Ala Asp Thr Ala Thr
             100                 105                 110

Tyr Phe Cys Ala Arg Tyr Ile Ile Pro Gly Tyr Asn Phe Asn Leu Trp
             115                 120                 125

Gly Pro Gly Thr Leu Val Thr Val Ser Ser
         130                 135

<210> SEQ ID NO 18
<211> LENGTH: 139
<212> TYPE: PRT
<213> ORGANISM: Oryctolagus cuniculus

<400> SEQUENCE: 18

Met Glu Thr Gly Leu Arg Trp Leu Leu Leu Val Ala Val Leu Lys Gly
  1               5                  10                 15

Val Gln Cys Gln Gln Gln Leu Val Glu Ser Gly Gly Gly Leu Val Lys
             20                  25                  30

Pro Gly Ala Ser Leu Thr Leu Thr Cys Lys Ala Ser Gly Phe Ser Phe
             35                  40                  45
```

```
Ser Ser Thr Tyr Trp Ile Cys Trp Val Arg Gln Ala Pro Gly Lys Gly
    50                  55                  60

Leu Glu Trp Ile Gly Cys Ile Asn Ser Asp Asp Ser Gly Thr Asn Val
65                  70                  75                  80

Tyr Ala Asn Trp Ala Lys Gly Arg Phe Thr Ile Ser Lys Ala Ser Ser
                85                  90                  95

Thr Thr Val Thr Leu Gln Met Thr Ser Leu Thr Ala Ala Asp Thr Ala
            100                 105                 110

Thr Tyr Phe Cys Ala Arg Tyr Pro Ile Pro Gly Tyr His Phe Asn Leu
            115                 120                 125

Trp Gly Pro Gly Thr Leu Val Thr Val Ser Ser
    130                 135

<210> SEQ ID NO 19
<211> LENGTH: 131
<212> TYPE: PRT
<213> ORGANISM: Oryctolagus cuniculus

<400> SEQUENCE: 19

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Thr Pro Leu Thr Leu Thr Cys Thr Val Ser Gly Phe Asp Leu Ser
            35                  40                  45

Ser Asn Ala Met Asn Trp Val Arg Gln Ala Pro Gly Lys Gly Leu Glu
    50                  55                  60

Trp Ile Gly Tyr Ile Thr Ile Ser Gly Ser Ala Gly Tyr Ala Ser Trp
65                  70                  75                  80

Ala Lys Gly Arg Phe Thr Ile Ser Lys Thr Ser Thr Val Asp Leu
                85                  90                  95

Lys Ile Ser Ser Pro Thr Thr Glu Asp Thr Ala Thr Tyr Phe Cys Ala
            100                 105                 110

Arg Gly Tyr Asn Thr Met Ala Ile Trp Gly Pro Gly Thr Leu Val Thr
            115                 120                 125

Val Ser Ser
    130

<210> SEQ ID NO 20
<211> LENGTH: 136
<212> TYPE: PRT
<213> ORGANISM: Oryctolagus cuniculus

<400> SEQUENCE: 20

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Asn Cys Thr Val Ser Gly Phe Ser Leu Ser
            35                  40                  45

Ser Tyr Asp Met Asn Trp Val Arg Gln Ala Pro Gly Lys Gly Leu Glu
    50                  55                  60

Trp Ile Gly Val Ile Trp Asn Asn Gly Glu Ile Phe Tyr Ala Ser Trp
65                  70                  75                  80

Ala Lys Gly Arg Phe Thr Ile Ser Lys Thr Ser Thr Val Asp Leu
                85                  90                  95
```

```
Lys Ile Thr Ser Pro Ser Thr Glu Asp Thr Ala Thr Tyr Phe Cys Ala
                100                 105                 110

Gly Asp Ala Asp Gly Gly Val Val Ser Tyr Phe His Val Trp Gly Pro
            115                 120                 125

Gly Thr Leu Val Thr Val Ser Ser
        130                 135

<210> SEQ ID NO 21
<211> LENGTH: 136
<212> TYPE: PRT
<213> ORGANISM: Oryctolagus cuniculus

<400> SEQUENCE: 21

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Asp Tyr Val Met Arg Trp Val Arg Gln Ala Pro Gly Lys Gly Leu Glu
    50                  55                  60

Trp Ile Gly Val Ile Ser Ser Ala Gly Asn Thr Tyr Tyr Ala Thr Trp
65                  70                  75                  80

Ala Lys Asp Arg Phe Thr Ile Ser Lys Thr Ser Thr Thr Val Asp Leu
                85                  90                  95

Arg Ile Ala Ser Pro Thr Thr Glu Asp Thr Ala Thr Tyr Phe Cys Ala
                100                 105                 110

Arg Ile Trp Arg Pro Asp Asp Pro Thr Asn Ser Asp Ile Trp Gly Pro
            115                 120                 125

Gly Thr Leu Val Thr Val Ser Ser
        130                 135

<210> SEQ ID NO 22
<211> LENGTH: 130
<212> TYPE: PRT
<213> ORGANISM: Oryctolagus cuniculus

<400> SEQUENCE: 22

Met Asp Thr Arg Ala Pro Thr Gln Leu Leu Gly Leu Leu Leu Leu Trp
1               5                   10                  15

Leu Pro Gly Ala Arg Cys Asp Val Val Met Thr Gln Thr Pro Ser Ser
            20                  25                  30

Ala Ser Ala Ala Val Gly Gly Thr Val Thr Thr Lys Cys Gln Ala Ser
        35                  40                  45

Gln Ser Ile Gly Ser Tyr Leu Ala Trp Tyr Gln Gln Lys Pro Gly Gln
    50                  55                  60

Arg Pro Lys Leu Leu Ile Tyr Ala Ala Ser Asn Leu Ala Ser Gly Val
65                  70                  75                  80

Pro Ser Arg Phe Lys Gly Ser Arg Ser Gly Thr Glu Tyr Thr Leu Thr
                85                  90                  95

Ile Ser Gly Val Gln Arg Glu Asp Ala Ala Thr Tyr Tyr Cys Leu Gly
                100                 105                 110

Ser Phe Thr Gly Ser Asp Thr Thr Phe Gly Gly Gly Thr Glu Leu Glu
            115                 120                 125

Ile Leu
    130
```

<210> SEQ ID NO 23
<211> LENGTH: 134
<212> TYPE: PRT
<213> ORGANISM: Oryctolagus cuniculus

<400> SEQUENCE: 23

Met Asp Thr Arg Ala Pro Thr Gln Leu Leu Gly Leu Leu Leu Trp
1               5                   10                  15

Leu Pro Gly Ala Arg Cys Ala Asp Ile Val Met Thr Gln Thr Pro Ala
            20                  25                  30

Ser Val Glu Ala Val Gly Gly Thr Ile Thr Ile Asn Cys Gln Ala
        35                  40                  45

Ser Glu Ser Ile Ser Ser Trp Leu Ser Trp Tyr Gln Gln Lys Pro Gly
    50                  55                  60

Gln Arg Pro Lys Leu Leu Ile Tyr Tyr Thr Ser Asn Leu Ala Ser Gly
65                  70                  75                  80

Val Pro Ser Arg Phe Lys Gly Ser Gly Ala Gly Thr Asp Phe Thr Leu
                85                  90                  95

Thr Ile Ser Asp Leu Glu Cys Ala Asp Ala Ala Thr Tyr Tyr Cys Gln
            100                 105                 110

Ser Asn Tyr Gly Ser Ser Ser Thr Tyr Tyr Gly Phe Gly Gly Gly
        115                 120                 125

Thr Glu Val Val Val Lys
    130

<210> SEQ ID NO 24
<211> LENGTH: 131
<212> TYPE: PRT
<213> ORGANISM: Oryctolagus cuniculus

<400> SEQUENCE: 24

Met Asp Thr Arg Ala Pro Thr Gln Leu Leu Gly Leu Leu Leu Trp
1               5                   10                  15

Leu Pro Gly Ala Arg Cys Ala Asp Ile Val Met Thr Gln Thr Pro Ser
            20                  25                  30

Ser Ala Ser Glu Pro Val Gly Gly Thr Val Thr Ile Lys Cys Gln Ala
        35                  40                  45

Ser Gln Ser Ile Ser Ser Arg Leu Ala Trp Tyr Gln Gln Lys Pro Gly
    50                  55                  60

Gln Pro Pro Lys Leu Leu Ile Tyr Arg Ala Ser Thr Leu Ala Ser Gly
65                  70                  75                  80

Val Ser Ser Arg Phe Lys Gly Ser Gly Ser Gly Thr Gln Phe Thr Leu
                85                  90                  95

Thr Ile Ser Asp Leu Glu Cys Ala Asp Ala Ala Thr Tyr Tyr Cys Gln
            100                 105                 110

Cys Thr Gly Tyr Thr Ile Ser Trp Pro Phe Gly Gly Gly Thr Glu Val
        115                 120                 125

Val Val Lys
    130

<210> SEQ ID NO 25
<211> LENGTH: 132
<212> TYPE: PRT
<213> ORGANISM: Oryctolagus cuniculus

<400> SEQUENCE: 25

Met Asp Thr Arg Ala Pro Thr Gln Leu Leu Gly Leu Leu Leu Trp
1               5                   10                  15

Leu Pro Gly Ala Arg Cys Ala Tyr Asp Met Thr Gln Thr Pro Ala Ser
            20                  25                  30

Val Ser Ala Ala Val Gly Asp Thr Val Thr Ile Lys Cys Gln Ala Ser
        35                  40                  45

Gln Ser Ile Ser Ser Tyr Leu Tyr Trp Tyr Gln Gln Lys Pro Gly Gln
    50                  55                  60

Pro Pro Lys Leu Leu Ile Tyr Gln Ala Ser Lys Leu Ala Ser Gly Val
65                  70                  75                  80

Pro Ser Arg Phe Lys Gly Ser Gly Ser Gly Thr Glu Tyr Thr Leu Thr
            85                  90                  95

Ile Ser Asp Leu Glu Cys Ala Asp Val Ala Thr Tyr Tyr Cys Gln Gln
            100                 105                 110

Gly Tyr Ser His Ile Asn Val Asp Asn Ile Phe Gly Gly Gly Phe Gln
            115                 120                 125

Val Val Val Lys
        130

<210> SEQ ID NO 26
<211> LENGTH: 133
<212> TYPE: PRT
<213> ORGANISM: Oryctolagus cuniculus

<400> SEQUENCE: 26

Met Asp Thr Arg Ala Pro Pro Gln Leu Leu Gly Leu Leu Leu Trp
1               5                   10                  15

Leu Pro Gly Ala Arg Cys Ala Asp Ile Val Met Thr Gln Thr Pro Ser
            20                  25                  30

Ser Val Glu Ala Ala Val Gly Gly Thr Val Thr Ile Lys Cys Gln Ala
        35                  40                  45

Ser Gln Ser Ile Tyr Thr Trp Leu Ala Trp Tyr Gln Gln Lys Pro Gly
    50                  55                  60

Gln Pro Pro Lys Leu Leu Ile Tyr Lys Ala Ser Thr Leu Ala Ser Gly
65                  70                  75                  80

Val Pro Ser Arg Phe Lys Gly Ser Gly Ser Gly Thr Asp Tyr Thr Leu
            85                  90                  95

Thr Ile Ser Asp Leu Glu Cys Asp Ala Ala Thr Tyr Tyr Cys Gln
            100                 105                 110

Arg Tyr Ser Trp Asn Gly Ser Tyr Gly Val Ser Phe Gly Gly Gly Thr
            115                 120                 125

Glu Val Val Val Arg
        130

<210> SEQ ID NO 27
<211> LENGTH: 135
<212> TYPE: PRT
<213> ORGANISM: Oryctolagus cuniculus

<400> SEQUENCE: 27

Met Asp Thr Arg Ala Pro Thr Gln Leu Leu Gly Leu Leu Leu Trp
1               5                   10                  15

Leu Pro Gly Ala Arg Cys Ala Asp Ile Val Met Thr Gln Thr Pro Ala
            20                  25                  30

Ser Val Ser Ala Ala Val Gly Gly Thr Val Thr Ile Asn Cys Gln Ala
        35                  40                  45

```
Ser Glu Ser Ala Tyr Thr Leu Leu Ala Trp Tyr Gln Gln Lys Pro Gly
    50                  55                  60

Gln Pro Pro Lys Leu Leu Ile Tyr Gly Ala Ser Ile Leu Glu Ser Gly
65                  70                  75                  80

Val Pro Ser Arg Phe Lys Gly Ser Gly Ser Gly Thr Asp Phe Thr Leu
                85                  90                  95

Thr Ile Ser Asp Leu Glu Cys Ala Asp Ala Ala Thr Tyr Tyr Cys Gln
            100                 105                 110

Ser His Tyr Phe Gly Ser Ser Gly Tyr Ala Asn Thr Phe Gly Gly Gly
            115                 120                 125

Gly Thr Glu Val Val Val Lys
            130             135

<210> SEQ ID NO 28
<211> LENGTH: 132
<212> TYPE: PRT
<213> ORGANISM: Oryctolagus cuniculus

<400> SEQUENCE: 28

Met Asp Thr Arg Ala Pro Thr Gln Leu Leu Gly Leu Leu Leu Leu Trp
1               5                   10                  15

Leu Pro Gly Ala Arg Cys Ala Tyr Asp Met Thr Gln Thr Pro Ala Ser
                20                  25                  30

Val Glu Val Ala Val Gly Gly Thr Val Thr Ile Asn Cys Gln Ala Ser
            35                  40                  45

Gln Ser Ile Ser Ser Tyr Leu Tyr Trp Tyr Gln Gln Lys Pro Gly Gln
    50                  55                  60

Pro Pro Lys Leu Leu Ile Tyr Asp Ala Ser Lys Leu Ala Ser Gly Val
65                  70                  75                  80

Pro Ser Arg Phe Lys Gly Ser Gly Ser Gly Thr Gln Phe Thr Leu Thr
                85                  90                  95

Ile Thr Gly Val Glu Cys Ala Asp Ala Ala Thr Tyr Tyr Cys Gln Gln
            100                 105                 110

Gly Tyr Ser His Ile Asn Val Asp Asn Ile Phe Gly Gly Gly Thr Glu
            115                 120                 125

Val Val Val Lys
    130

<210> SEQ ID NO 29
<211> LENGTH: 132
<212> TYPE: PRT
<213> ORGANISM: Oryctolagus cuniculus

<400> SEQUENCE: 29

Met Asp Thr Arg Ala Pro Thr Gln Leu Leu Gly Leu Leu Leu Leu Trp
1               5                   10                  15

Leu Pro Gly Ala Arg Cys Ala Tyr Asp Met Thr Gln Thr Pro Ala Ser
                20                  25                  30

Val Glu Val Ala Val Gly Gly Thr Val Thr Ile Lys Cys Gln Ala Ser
            35                  40                  45

Gln Asn Ile Tyr Gly Tyr Leu Phe Trp Tyr Gln Gln Lys Pro Gly Gln
    50                  55                  60

Pro Pro Asn Leu Leu Ile Ala Glu Ala Ser Lys Leu Pro Ser Gly Val
65                  70                  75                  80

Pro Ser Arg Phe Lys Gly Ser Gly Ser Gly Thr Glu Tyr Ser Leu Thr
                85                  90                  95
```

Ile Ser Gly Val Glu Cys Ala Asp Ala Ala Thr Tyr Tyr Cys Gln Gln
            100                 105                 110

Ser Tyr Ser His Ile Asn Val Asp Asn Ile Phe Gly Gly Gly Thr Glu
        115                 120                 125

Val Val Val Lys
        130

<210> SEQ ID NO 30
<211> LENGTH: 133
<212> TYPE: PRT
<213> ORGANISM: Oryctolagus cuniculus

<400> SEQUENCE: 30

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Pro Ser Pro
            20                  25                  30

Val Ser Ala Pro Val Gly Gly Thr Val Thr Ile Asn Cys Gln Ser Ser
        35                  40                  45

Gln Asn Val Leu Ile Asn Asn Arg Leu Ala Trp Tyr Gln Gln Lys Pro
    50                  55                  60

Gly Gln Pro Pro Lys Leu Leu Ile Tyr Asp Ala Ser Lys Leu Ala Ser
65                  70                  75                  80

Gly Val Pro Ser Arg Phe Lys Gly Ser Gly Ser Gly Thr Gln Phe Thr
                85                  90                  95

Leu Thr Ile Ser Gly Val Gln Cys Asp Asp Ala Ala Thr Tyr Tyr Cys
            100                 105                 110

Gln Ala Gly Tyr Ser Ser Gly Asp Gly Asn Ala Phe Gly Gly Gly Thr
        115                 120                 125

Glu Val Val Val Lys
        130

<210> SEQ ID NO 31
<211> LENGTH: 132
<212> TYPE: PRT
<213> ORGANISM: Oryctolagus cuniculus

<400> SEQUENCE: 31

Met Asp Thr Arg Ala Pro Thr Gln Leu Leu Gly Leu Leu Leu Leu Trp
1               5                   10                  15

Leu Pro Gly Ala Arg Cys Ala Tyr Asp Met Thr Gln Thr Pro Ala Ser
            20                  25                  30

Val Glu Val Ala Val Gly Gly Thr Val Thr Ile Lys Cys Gln Ala Ser
        35                  40                  45

Gln Thr Ile Tyr Thr Tyr Leu Ala Trp Tyr Leu Gln Lys Pro Gly Gln
    50                  55                  60

Pro Pro Lys Leu Leu Ile Tyr Glu Ala Ser Lys Leu Ala Ser Gly Val
65                  70                  75                  80

Ser Ser Arg Phe Glu Gly Ser Gly Ser Gly Thr Gln Phe Thr Leu Thr
                85                  90                  95

Ile Ser Gly Val Gln Cys Asp Asp Ala Ala Thr Tyr Tyr Cys Gln Gln
            100                 105                 110

Gly Tyr Asn Ser Arg His Val Asp Asn Val Phe Gly Gly Gly Thr Glu
        115                 120                 125

Val Val Val Lys
        130

<210> SEQ ID NO 32
<211> LENGTH: 132
<212> TYPE: PRT
<213> ORGANISM: Oryctolagus cuniculus

<400> SEQUENCE: 32

Met Asp Thr Arg Ala Pro Thr Gln Leu Leu Gly Leu Leu Leu Leu Trp
1               5                   10                  15

Leu Pro Gly Ala Arg Cys Asp Val Val Met Thr Gln Thr Pro Ser Ser
            20                  25                  30

Thr Ser Ala Ala Val Gly Gly Thr Val Thr Ile Lys Cys Gln Ala Ser
        35                  40                  45

Glu Ser Ile Ser Ser Ser Leu Ala Trp Tyr Gln Gln Lys Pro Gly Gln
    50                  55                  60

Pro Pro Lys Leu Leu Ile Tyr Tyr Ala Ser Asp Leu Ala Ser Gly Val
65                  70                  75                  80

Pro Ser Arg Phe Ser Gly Ser Arg Ser Gly Thr Glu Tyr Thr Leu Thr
                85                  90                  95

Ile Ser Gly Val Gln Arg Glu Asp Ala Ala Thr Tyr Tyr Cys Leu Gly
            100                 105                 110

Gly Tyr Ala Thr Ala Ala Tyr Arg Thr Ala Phe Gly Gly Gly Thr Glu
        115                 120                 125

Leu Glu Ile Leu
    130

<210> SEQ ID NO 33
<211> LENGTH: 138
<212> TYPE: PRT
<213> ORGANISM: Oryctolagus cuniculus

<400> SEQUENCE: 33

Met Glu Thr Gly Leu Arg Trp Leu Leu Leu Val Ala Val Leu Lys Gly
1               5                   10                  15

Val Gln Cys Gln Gln Gln Leu Glu Glu Ser Gly Gly Gly Leu Val Lys
            20                  25                  30

Pro Glu Gly Ser Leu Thr Leu Thr Cys Lys Ala Asn Gly Phe Ser Phe
        35                  40                  45

Ser Ala Asn Tyr Tyr Met Cys Trp Val Arg Gln Ala Pro Gly Lys Gly
    50                  55                  60

Leu Glu Leu Ile Ala Cys Ile Tyr Ala Ser Ser Gly Ser Thr Trp Tyr
65                  70                  75                  80

Ala Ser Trp Ala Lys Gly Arg Phe Thr Ile Ser Lys Thr Ser Ser Leu
                85                  90                  95

Asn Thr Val Thr Leu Gln Met Thr Ser Leu Thr Val Ala Asp Thr Ala
            100                 105                 110

Thr Tyr Phe Cys Ala Arg Ser Gly Tyr Ala Ala Tyr Asp Leu Trp
        115                 120                 125

Gly Pro Gly Thr Leu Val Thr Val Ser Ser
    130                 135

<210> SEQ ID NO 34
<211> LENGTH: 139
<212> TYPE: PRT
<213> ORGANISM: Oryctolagus cuniculus

<400> SEQUENCE: 34

Met Glu Thr Gly Leu Arg Trp Leu Leu Leu Val Ala Val Leu Lys Gly

```
1               5                   10                  15
Val Gln Cys Gln Glu Gln Leu Glu Glu Ser Gly Gly Asp Leu Val Lys
            20                  25                  30

Pro Gly Ala Ser Leu Thr Leu Thr Cys Lys Ala Ser Gly Phe Asp Leu
        35                  40                  45

Ser Ser Thr Tyr Tyr Met Cys Trp Val Arg Gln Ala Pro Gly Lys Gly
    50                  55                  60

Leu Glu Trp Ile Gly Cys Ile Tyr Ala Thr Gly Thr Tyr Tyr Ala
65                  70                  75                  80

Ser Trp Ala Lys Gly Arg Phe Thr Ile Ser Lys Thr Ser Pro Thr Thr
                85                  90                  95

Val Thr Leu Gln Met Pro Ser Leu Thr Ala Ala Asp Thr Ala Thr Tyr
            100                 105                 110

Phe Cys Ala Arg Asp Ile Val Gly Asp Asn Ile Tyr Tyr Phe Asn Phe
        115                 120                 125

Trp Gly Pro Gly Thr Leu Val Thr Val Ser Ser
    130                 135
```

<210> SEQ ID NO 35
<211> LENGTH: 139
<212> TYPE: PRT
<213> ORGANISM: Oryctolagus cuniculus

<400> SEQUENCE: 35

```
Met Glu Thr Gly Leu Arg Trp Leu Leu Leu Val Ala Val Leu Lys Gly
1               5                   10                  15

Val Gln Cys Gln Glu Gln Leu Glu Glu Ser Gly Gly Asp Leu Val Lys
            20                  25                  30

Pro Glu Gly Ser Leu Thr Leu Thr Cys Thr Ala Ser Gly Phe Ser Phe
        35                  40                  45

Gly Ser Gly Tyr Tyr Met Cys Trp Val Arg Gln Ala Pro Gly Lys Gly
    50                  55                  60

Leu Glu Trp Ile Gly Cys Ile Tyr Val Gly His Asp Ser Leu Tyr Tyr
65                  70                  75                  80

Ala Gly Trp Ala Arg Gly Arg Phe Thr Ile Ser Lys Thr Ser Ser Thr
                85                  90                  95

Thr Val Thr Leu Gln Met Thr Ser Leu Thr Ala Ala Asp Thr Ala Thr
            100                 105                 110

Tyr Phe Cys Ala Arg Gly Ala Ser Ile Thr Asn Ser Tyr Phe Ser Leu
        115                 120                 125

Trp Gly Pro Gly Thr Leu Val Thr Val Ser Ser
    130                 135
```

<210> SEQ ID NO 36
<211> LENGTH: 142
<212> TYPE: PRT
<213> ORGANISM: Oryctolagus cuniculus

<400> SEQUENCE: 36

```
Met Glu Thr Gly Leu Arg Trp Leu Leu Leu Val Ala Val Leu Lys Gly
1               5                   10                  15

Val Gln Cys Gln Glu Gln Leu Val Glu Ser Gly Gly Gly Leu Val Lys
            20                  25                  30

Pro Gly Ala Ser Leu Ala Val Thr Cys Lys Ala Ser Gly Phe Ser Phe
        35                  40                  45

Ser Arg Gly Tyr Tyr Met Cys Trp Val Arg Gln Ala Pro Gly Lys Gly
```

```
                 50                  55                  60
Leu Glu Trp Ile Ala Cys Ile Gly Ala Gly Ser Gly Asn Thr Tyr Tyr
 65                  70                  75                  80

Ala Thr Trp Thr Lys Gly Arg Ala Thr Ile Ser Lys Thr Ser Trp Thr
                 85                  90                  95

Thr Val Ser Leu Glu Met Thr Ser Leu Thr Gly Ala Asp Thr Ala Thr
                100                 105                 110

Tyr Phe Cys Ala Arg Glu Asp Pro Gly Asn Asp Asp Tyr Gly Tyr Ala
                115                 120                 125

Asp Asn Leu Trp Gly Pro Gly Thr Leu Val Thr Val Ser Ser
                130                 135                 140

<210> SEQ ID NO 37
<211> LENGTH: 144
<212> TYPE: PRT
<213> ORGANISM: Oryctolagus cuniculus

<400> SEQUENCE: 37

Met Glu Thr Gly Leu Arg Trp Leu Leu Leu Val Ala Val Leu Lys Gly
 1               5                  10                  15

Val Gln Cys Gln Ser Leu Glu Glu Ser Gly Gly Asp Leu Val Lys Pro
                 20                  25                  30

Gly Ala Ser Leu Thr Leu Thr Cys Thr Ala Ser Gly Phe Ser Phe Ser
                 35                  40                  45

Asp Ser Phe Trp Ile Ala Trp Val Arg Gln Ala Pro Gly Lys Gly Leu
                 50                  55                  60

Glu Trp Ile Gly Cys Ile His Ala Leu Ser Gly Ser Thr Tyr Tyr
 65                  70                  75                  80

Ala Asn Trp Ala Arg Gly Arg Phe Thr Ile Ser Lys Thr Ser Ser Thr
                 85                  90                  95

Thr Val Thr Leu Gln Met Asn Ser Leu Thr Ala Ala Asp Thr Ala Thr
                100                 105                 110

Tyr Phe Cys Ala Arg Ser Tyr Ala Gly Tyr Ala Asp Tyr Asn Val Ala
                115                 120                 125

Thr Gly Leu Asn Leu Trp Gly Pro Gly Thr Leu Val Thr Val Ser Ser
                130                 135                 140

<210> SEQ ID NO 38
<211> LENGTH: 139
<212> TYPE: PRT
<213> ORGANISM: Oryctolagus cuniculus

<400> SEQUENCE: 38

Met Glu Thr Gly Leu Arg Trp Leu Leu Leu Val Ala Val Leu Lys Gly
 1               5                  10                  15

Val Gln Cys Gln Glu Gln Leu Glu Glu Ser Gly Gly Asp Leu Val Lys
                 20                  25                  30

Pro Glu Gly Ser Leu Thr Leu Thr Cys Thr Ala Ser Gly Phe Ser Phe
                 35                  40                  45

Gly Ser Gly Tyr Tyr Met Cys Trp Val Arg Gln Ala Pro Gly Lys Gly
                 50                  55                  60

Leu Glu Trp Ile Gly Cys Ile Tyr Val Gly His Asp Ser Leu Tyr Tyr
 65                  70                  75                  80

Ala Gly Trp Ala Arg Gly Arg Phe Thr Ile Ser Lys Thr Ser Ser Thr
                 85                  90                  95

Thr Val Thr Leu Gln Met Thr Ser Leu Thr Ala Ala Asp Thr Ala Thr
```

```
            100                 105                 110
Tyr Phe Cys Ala Arg Gly Ala Ser Ile Thr Asn Ser Tyr Phe Ser Leu
            115                 120                 125

Trp Gly Pro Gly Thr Leu Val Thr Val Ser Ser
            130                 135

<210> SEQ ID NO 39
<211> LENGTH: 139
<212> TYPE: PRT
<213> ORGANISM: Oryctolagus cuniculus

<400> SEQUENCE: 39

Met Glu Thr Gly Leu Arg Trp Leu Leu Leu Val Ala Val Leu Lys Gly
1               5                   10                  15

Val Gln Cys Gln Glu Gln Leu Val Glu Ser Gly Gly Asp Leu Val Gln
            20                  25                  30

Pro Glu Gly Ser Leu Thr Leu Thr Ser Thr Ala Ser Gly Phe Ser Leu
            35                  40                  45

Ser Ser Ser Tyr Phe Met Cys Trp Val Arg Gln Ala Pro Gly Lys Gly
    50                  55                  60

Leu Glu Trp Ile Ala Cys Ile Ser Ala Gly Ser Ser Gly His Thr Tyr
65                  70                  75                  80

Tyr Ala Ser Trp Ala Lys Gly Arg Phe Thr Val Ser Lys Thr Ser Ser
                85                  90                  95

Thr Thr Val Thr Leu Gln Met Thr Ser Leu Thr Ala Ala Asp Thr Ala
            100                 105                 110

Thr Tyr Phe Cys Ala Arg Ala Ser Ala Asp Val Gly Asp Tyr Ser Leu
            115                 120                 125

Trp Gly Pro Gly Thr Leu Val Thr Val Ser Ser
            130                 135

<210> SEQ ID NO 40
<211> LENGTH: 144
<212> TYPE: PRT
<213> ORGANISM: Oryctolagus cuniculus

<400> SEQUENCE: 40

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Asp Leu Val Lys Pro
            20                  25                  30

Gly Ala Ser Leu Thr Leu Thr Cys Thr Ala Ser Gly Phe Ser Phe Ser
            35                  40                  45

Asp Ser Phe Trp Ile Ala Trp Val Arg Gln Ala Pro Gly Lys Gly Leu
    50                  55                  60

Glu Trp Ile Gly Cys Ile His Ala Leu Ser Ser Gly Ser Thr Tyr Tyr
65                  70                  75                  80

Ala Asn Trp Ala Arg Gly Arg Phe Thr Ile Ser Lys Thr Ser Ser Thr
                85                  90                  95

Thr Val Thr Leu Gln Met Asn Ser Leu Thr Ala Ala Asp Thr Ala Thr
            100                 105                 110

Tyr Phe Cys Ala Arg Ser Tyr Ala Gly Tyr Ala Asp Tyr Asn Val Ala
            115                 120                 125

Thr Gly Leu Asn Leu Trp Gly Pro Gly Thr Leu Val Thr Val Ser Ser
            130                 135                 140
```

<210> SEQ ID NO 41
<211> LENGTH: 144
<212> TYPE: PRT
<213> ORGANISM: Oryctolagus cuniculus

<400> SEQUENCE: 41

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Asp Leu Val Lys Pro
            20                  25                  30

Gly Ala Ser Leu Thr Leu Thr Cys Thr Ala Ser Gly Phe Ser Phe Ser
        35                  40                  45

Gly Thr Tyr Trp Ile Cys Trp Val Arg Gln Ala Pro Gly Lys Gly Leu
    50                  55                  60

Glu Trp Ile Ala Cys Ile Tyr Ala Gly Ala Ser Gly Asn Ser Tyr Tyr
65                  70                  75                  80

Ala Asn Trp Ala Gln Gly Arg Phe Ile Ile Ser Lys Arg Ser Ser Thr
                85                  90                  95

Ala Val Thr Leu Gln Met Thr Ser Leu Thr Ala Ala Asp Thr Ala Thr
            100                 105                 110

Tyr Phe Cys Ala Arg Ser Tyr Thr Gly Tyr Ala Asp Tyr Asn Val Ala
        115                 120                 125

Thr Gly Leu Asn Leu Trp Gly Pro Gly Thr Leu Val Thr Val Ser Ser
    130                 135                 140

<210> SEQ ID NO 42
<211> LENGTH: 134
<212> TYPE: PRT
<213> ORGANISM: Oryctolagus cuniculus

<400> SEQUENCE: 42

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Ile Thr Pro
            20                  25                  30

Gly Thr Pro Leu Thr Leu Thr Cys Thr Val Ser Gly Phe Ser Leu Ser
        35                  40                  45

Ser Tyr Ala Val Asn Trp Val Arg Gln Ala Pro Gly Lys Gly Leu Glu
    50                  55                  60

Tyr Ile Gly Leu Ile Ala Thr Gly Gly Gly Thr Phe Tyr Thr Asn Trp
65                  70                  75                  80

Ala Arg Gly Arg Leu Thr Ile Ser Lys Thr Ser Thr Thr Val Asp Leu
                85                  90                  95

Lys Met Pro Ser Pro Gln Thr Glu Asp Thr Ala Thr Tyr Phe Cys Val
            100                 105                 110

Arg Gly Tyr Pro Gly Ser Ser Asp Phe Asn Ile Trp Gly Pro Gly Thr
        115                 120                 125

Leu Val Thr Val Ser Ser
    130

<210> SEQ ID NO 43
<211> LENGTH: 135
<212> TYPE: PRT
<213> ORGANISM: Oryctolagus cuniculus

<400> SEQUENCE: 43

Met Glu Thr Gly Leu Arg Trp Leu Leu Leu Val Ala Val Leu Lys Gly
1               5                   10                  15

```
Val Gln Cys Gln Ser Leu Glu Glu Ser Gly Gly Arg Leu Val Thr Pro
            20                  25                  30
Gly Thr Pro Leu Thr Leu Thr Cys Thr Val Ser Gly Phe Ser Leu Ser
            35                  40                  45
Thr Tyr Asp Met Thr Trp Val Arg Gln Ala Pro Gly Lys Gly Leu Glu
 50                  55                  60
Trp Leu Gly Leu Ile Asn Thr Ile Gly Ser Ala Tyr Tyr Ala Ser Trp
 65                  70                  75                  80
Ala Ser Gly Arg Phe Thr Ile Ser Lys Thr Ser Thr Ser Val Thr Leu
                85                  90                  95
Lys Met Thr Ser Pro Thr Thr Glu Asp Thr Ala Thr Tyr Phe Cys Val
                100                 105                 110
Arg Gly Val Pro Gly Tyr Ser Ser Phe Asn Ile Trp Gly Pro Gly
                115                 120                 125
Thr Leu Val Thr Val Ser Ser
    130                 135
```

<210> SEQ ID NO 44
<211> LENGTH: 134
<212> TYPE: PRT
<213> ORGANISM: Oryctolagus cuniculus

<400> SEQUENCE: 44

```
Met Glu Thr Gly Leu Arg Trp Leu Leu Leu Val Ala Val Leu Lys Gly
 1               5                  10                  15
Val Gln Ser Gln Ser Val Glu Glu Ser Gly Gly Arg Leu Ile Thr Pro
            20                  25                  30
Gly Thr Pro Leu Thr Leu Thr Cys Thr Ile Ser Gly Phe Ser Leu Ser
            35                  40                  45
Ser Tyr Ala Val Asp Trp Val Arg Gln Ala Pro Gly Lys Gly Leu Glu
 50                  55                  60
Tyr Ile Gly Ile Ile Ala Thr Gly Gly Thr Tyr Tyr Thr Asn Trp
 65                  70                  75                  80
Ala Lys Gly Arg Phe Thr Ile Ser Lys Thr Ser Thr Thr Val Asp Leu
                85                  90                  95
Lys Met Thr Ser Pro Gln Pro Glu Asp Thr Ala Thr Tyr Phe Cys Val
                100                 105                 110
Arg Gly Tyr Pro Gly Ser Ser Asp Phe Asn Ile Trp Gly Pro Gly Thr
                115                 120                 125
Leu Val Thr Val Ser Ser
    130
```

<210> SEQ ID NO 45
<211> LENGTH: 134
<212> TYPE: PRT
<213> ORGANISM: Oryctolagus cuniculus

<400> SEQUENCE: 45

```
Met Asp Thr Arg Ala Pro Thr Gln Leu Leu Gly Leu Leu Leu Leu Trp
 1               5                  10                  15
Leu Pro Gly Ala Thr Phe Ala Ala Val Leu Thr Gln Thr Pro Ser Pro
            20                  25                  30
Val Ser Ala Ala Val Gly Gly Thr Val Ser Ile Ser Cys Gln Ser Ser
            35                  40                  45
Lys Ser Val Tyr Asn Asn Asn Trp Leu Ser Trp Tyr Gln Gln Lys Pro
 50                  55                  60
```

Gly Gln Pro Pro Lys Leu Leu Ile Tyr Arg Ala Ser Thr Leu Ala Ser
65                  70                  75                  80

Gly Val Pro Ser Arg Phe Arg Gly Ser Gly Ser Gly Thr Glu Phe Thr
                85                  90                  95

Leu Thr Ile Ser Asp Val Val Cys Asp Asp Ala Ala Thr Tyr Tyr Cys
            100                 105                 110

Ala Gly Tyr Glu Ser Val Asn Thr Asp Gly His Ala Phe Gly Gly Gly
        115                 120                 125

Thr Glu Val Val Val Lys
    130

<210> SEQ ID NO 46
<211> LENGTH: 132
<212> TYPE: PRT
<213> ORGANISM: Oryctolagus cuniculus

<400> SEQUENCE: 46

Met Asp Thr Arg Ala Pro Thr Gln Leu Leu Gly Leu Leu Leu Leu Trp
1               5                   10                  15

Leu Pro Gly Ala Arg Cys Ala Leu Val Met Thr Gln Thr Pro Ser Ser
            20                  25                  30

Val Ser Ala Ala Val Gly Gly Thr Val Thr Ile Asn Cys Gln Ala Ser
        35                  40                  45

Gln Thr Ile Ser Asn Glu Leu Ser Trp Tyr Gln Gln Lys Pro Gly Gln
    50                  55                  60

Pro Pro Lys Leu Leu Ile Tyr Leu Ala Ser Thr Leu Ala Ser Gly Val
65                  70                  75                  80

Pro Ser Arg Phe Lys Gly Ser Gly Ser Gly Thr Gln Phe Thr Leu Thr
                85                  90                  95

Ile Ser Asp Leu Glu Cys Ala Asp Ala Ala Thr Tyr Tyr Cys Gln Gln
            100                 105                 110

Gly Tyr Thr Tyr Ser Ser Val Asp Asn Val Phe Gly Gly Gly Thr Glu
        115                 120                 125

Val Val Val Lys
    130

<210> SEQ ID NO 47
<211> LENGTH: 131
<212> TYPE: PRT
<213> ORGANISM: Oryctolagus cuniculus

<400> SEQUENCE: 47

Met Asp Thr Arg Ala Pro Thr Gln Leu Leu Gly Leu Leu Leu Leu Trp
1               5                   10                  15

Leu Pro Gly Val Thr Phe Ala Ile Glu Met Thr Gln Thr Pro Phe Ser
            20                  25                  30

Val Ser Glu Pro Val Gly Gly Thr Val Thr Ile Lys Cys Gln Ala Ser
        35                  40                  45

Glu Asp Ile Phe Ser Asn Leu Gly Trp Tyr Gln Gln Lys Pro Gly Gln
    50                  55                  60

Pro Pro Lys Leu Leu Ile Tyr Ala Ala Ser Asn Leu Glu Ser Gly Val
65                  70                  75                  80

Pro Ser Arg Phe Lys Gly Ser Gly Ser Gly Thr Asp Phe Thr Leu Thr
                85                  90                  95

Ile Asn Asp Leu Glu Cys Asp Asp Ala Ala Thr Tyr Tyr Cys Gln Ser
            100                 105                 110

Ala Tyr Tyr Ser Ser Ser Tyr Leu Ala Phe Gly Gly Gly Thr Glu Val
            115                 120                 125

Val Val Lys
    130

<210> SEQ ID NO 48
<211> LENGTH: 135
<212> TYPE: PRT
<213> ORGANISM: Oryctolagus cuniculus

<400> SEQUENCE: 48

Met Asp Thr Arg Ala Pro Thr Gln Leu Leu Gly Leu Leu Leu Leu Trp
1               5                   10                  15

Leu Pro Gly Ala Arg Cys Ala Asp Ile Val Met Thr Gln Thr Pro Ser
            20                  25                  30

Ser Val Ser Ala Ala Val Gly Gly Thr Val Thr Ile Lys Cys Gln Ala
        35                  40                  45

Ser Glu Thr Ile Tyr Thr Leu Leu Ala Trp Tyr Gln Gln Lys Pro Gly
    50                  55                  60

Gln Pro Pro Lys Leu Leu Ile Tyr Arg Ala Ser Thr Leu Glu Ser Gly
65                  70                  75                  80

Val Pro Ser Arg Phe Gln Gly Ser Gly Ser Gly Thr Glu Phe Thr Leu
                85                  90                  95

Thr Ile Ser Asp Leu Glu Cys Ala Asp Ala Ala Thr Tyr Tyr Cys Gln
            100                 105                 110

Ser His Tyr Phe Asp Ser Ser Ser Gly Tyr Gly Asn Thr Phe Gly Gly
        115                 120                 125

Gly Thr Glu Val Val Val Lys
    130                 135

<210> SEQ ID NO 49
<211> LENGTH: 130
<212> TYPE: PRT
<213> ORGANISM: Oryctolagus cuniculus

<400> SEQUENCE: 49

Met Asp Thr Arg Ala Pro Thr Gln Leu Leu Gly Leu Leu Leu Leu Trp
1               5                   10                  15

Leu Pro Gly Ala Arg Cys Asp Val Val Met Thr Gln Thr Pro Ser Ser
            20                  25                  30

Ala Ser Ala Ala Val Gly Gly Thr Val Thr Ile Lys Cys Gln Ala Ser
        35                  40                  45

Gln Ser Ile Gly Ser Tyr Leu Ala Trp Tyr Gln Gln Lys Pro Gly Gln
    50                  55                  60

Arg Pro Lys Leu Leu Ile Tyr Ala Ala Ser Asn Leu Ala Ser Gly Val
65                  70                  75                  80

Pro Ser Arg Phe Lys Gly Ser Arg Ser Gly Thr Glu Tyr Thr Leu Thr
                85                  90                  95

Ile Ser Gly Val Gln Arg Glu Asp Ala Ala Thr Tyr Tyr Cys Leu Gly
            100                 105                 110

Ser Phe Thr Gly Ser Asp Thr Phe Gly Gly Gly Thr Glu Leu Glu
        115                 120                 125

Ile Leu
    130

<210> SEQ ID NO 50

```
<211> LENGTH: 131
<212> TYPE: PRT
<213> ORGANISM: Oryctolagus cuniculus

<400> SEQUENCE: 50

Met Asp Thr Arg Ala Pro Thr Gln Leu Leu Gly Leu Leu Leu Leu Trp
1               5                   10                  15

Leu Pro Gly Val Thr Phe Ala Ile Glu Met Thr Gln Thr Pro Phe Ser
            20                  25                  30

Val Ser Glu Pro Val Gly Gly Thr Val Thr Ile Lys Cys Gln Ala Ser
        35                  40                  45

Glu Asp Ile Phe Ser Asn Leu Gly Trp Tyr Gln Gln Lys Pro Gly Gln
    50                  55                  60

Pro Pro Lys Leu Leu Ile Tyr Ala Ala Ser Asn Leu Glu Ser Gly Val
65                  70                  75                  80

Pro Ser Arg Phe Lys Gly Ser Gly Ser Gly Thr Asp Phe Thr Leu Thr
                85                  90                  95

Ile Asn Asp Leu Glu Cys Asp Asp Ala Ala Thr Tyr Tyr Cys Gln Ser
            100                 105                 110

Ala Tyr Tyr Ser Ser Ser Tyr Leu Ala Phe Gly Gly Gly Thr Glu Val
        115                 120                 125

Val Val Lys
    130

<210> SEQ ID NO 51
<211> LENGTH: 130
<212> TYPE: PRT
<213> ORGANISM: Oryctolagus cuniculus

<400> SEQUENCE: 51

Met Asp Thr Arg Ala Pro Thr Gln Leu Leu Gly Leu Leu Leu Leu Trp
1               5                   10                  15

Leu Pro Gly Ala Arg Cys Asp Val Met Met Thr Gln Thr Pro Ala Ser
            20                  25                  30

Val Ser Ala Pro Val Gly Gly Thr Val Thr Ile Lys Cys Gln Ala Ser
        35                  40                  45

Gln Ser Ile Ser Thr Tyr Leu Ala Trp Tyr Gln Gln Lys Pro Gly Gln
    50                  55                  60

Pro Pro Lys Leu Leu Ile Tyr Tyr Ala Ser Thr Leu Ala Ser Gly Val
65                  70                  75                  80

Ser Ser Arg Phe Glu Gly Ser Arg Ser Val Thr Glu Tyr Thr Leu Thr
                85                  90                  95

Ile Ser Asp Leu Glu Cys Ala Asp Ala Ala Thr Tyr Tyr Cys Gln Ser
            100                 105                 110

Thr Tyr Tyr Gly Asn Gly His Pro Phe Gly Gly Gly Thr Glu Val Val
        115                 120                 125

Val Lys
    130

<210> SEQ ID NO 52
<211> LENGTH: 130
<212> TYPE: PRT
<213> ORGANISM: Oryctolagus cuniculus

<400> SEQUENCE: 52

Met Asp Thr Arg Ala Pro Thr Gln Leu Leu Gly Leu Leu Leu Leu Trp
1               5                   10                  15
```

```
Leu Pro Gly Ala Arg Cys Asp Val Val Met Thr Gln Thr Pro Ser Ser
            20                  25                  30

Ala Ser Ala Ala Val Gly Gly Thr Val Thr Ile Lys Cys Gln Ala Ser
        35                  40                  45

Gln Ser Ile Gly Ser Tyr Leu Ala Trp Tyr Gln Gln Lys Pro Gly Gln
    50                  55                  60

Arg Pro Lys Leu Leu Ile Tyr Ala Ala Ser Asn Leu Ala Ser Gly Val
65                  70                  75                  80

Pro Ser Arg Phe Lys Gly Ser Arg Ser Gly Thr Glu Tyr Thr Leu Thr
                85                  90                  95

Ile Ser Gly Val Gln Arg Glu Asp Ala Ala Thr Tyr Tyr Cys Leu Gly
            100                 105                 110

Ser Phe Thr Gly Ser Asp Thr Thr Phe Gly Gly Gly Thr Glu Leu Glu
        115                 120                 125

Ile Leu
    130

<210> SEQ ID NO 53
<211> LENGTH: 130
<212> TYPE: PRT
<213> ORGANISM: Oryctolagus cuniculus

<400> SEQUENCE: 53

Met Asp Thr Arg Ala Pro Thr Gln Leu Leu Gly Leu Leu Leu Leu Trp
1               5                   10                  15

Leu Pro Gly Ala Arg Cys Ala Leu Val Met Thr Gln Thr Pro Ser Ser
            20                  25                  30

Thr Ser Ala Ala Val Gly Gly Thr Val Thr Ile Lys Cys Gln Ala Ser
        35                  40                  45

Gln Ser Ile Gly Ser Tyr Leu Ala Trp Tyr Gln Gln Lys Pro Gly Gln
    50                  55                  60

Arg Pro Lys Leu Leu Ile Tyr Ala Ala Ser Asn Leu Ala Ser Gly Asp
65                  70                  75                  80

Pro Ser Arg Phe Ser Ala Ser Arg Ser Gly Thr Glu Tyr Thr Leu Thr
                85                  90                  95

Ile Ser Gly Val Gln Arg Glu Asp Ala Ala Thr Tyr Tyr Cys Leu Gly
            100                 105                 110

Ser Phe Thr Gly Ser Asp Thr Thr Phe Gly Gly Gly Thr Glu Leu Glu
        115                 120                 125

Ile Leu
    130

<210> SEQ ID NO 54
<211> LENGTH: 119
<212> TYPE: PRT
<213> ORGANISM: Oryctolagus cuniculus

<400> SEQUENCE: 54

Ala Leu Ala Pro Gly Ala Arg Cys Ala Val Val Leu Thr Gln Thr Pro
1               5                   10                  15

Ala Ser Val Ser Ala Ala Val Gly Gly Thr Val Ser Ile Ser Cys Gln
            20                  25                  30

Ser Ser Lys Ser Val Tyr Asn Lys His His Leu Ala Trp Leu Gln Gln
        35                  40                  45

Lys Pro Gly Gln Pro Pro Lys Leu Leu Ile Tyr Tyr Ala Ser Thr Leu
    50                  55                  60
```

Ala Ser Gly Val Pro Ser Arg Phe Arg Gly Ser Gly Ser Gly Thr Gln
65                  70                  75                  80

Phe Thr Leu Thr Ile Ser Asp Val Gln Cys Asp Asp Ala Ala Thr Tyr
                85                  90                  95

Tyr Cys Ala Gly Gly Tyr Pro Ser Asp Ser Asp Asn Thr Phe Gly Gly
            100                 105                 110

Gly Thr Glu Val Val Val Glu
        115

<210> SEQ ID NO 55
<211> LENGTH: 134
<212> TYPE: PRT
<213> ORGANISM: Oryctolagus cuniculus

<400> SEQUENCE: 55

Met Asp Thr Arg Ala Pro Thr Gln Leu Leu Gly Leu Leu Leu Leu Trp
1               5                   10                  15

Leu Pro Gly Ala Thr Phe Ala Ile Val Met Thr Gln Thr Pro Ser Ser
            20                  25                  30

Lys Ser Val Ala Val Gly Asp Thr Val Thr Ile Asn Cys Gln Ala Ser
        35                  40                  45

Glu Ser Val Asp Ser Asn Lys Arg Leu Ala Trp Tyr Gln Gln Lys Pro
50                  55                  60

Gly Gln Pro Pro Lys Leu Leu Ile Tyr Thr Ala Ser Thr Leu Ala Ser
65                  70                  75                  80

Gly Val Pro Ser Arg Phe Lys Gly Ser Gly Ser Gly Thr Glu Phe Thr
                85                  90                  95

Leu Thr Ile Ser Asp Val Val Cys Asp Ala Ala Thr Tyr Tyr Cys
            100                 105                 110

Ala Gly Tyr Lys Ala Thr Thr Thr Asp Ala Ser Ala Phe Gly Gly Gly
            115                 120                 125

Thr Glu Val Val Val Lys
    130

<210> SEQ ID NO 56
<211> LENGTH: 133
<212> TYPE: PRT
<213> ORGANISM: Oryctolagus cuniculus

<400> SEQUENCE: 56

Met Asp Thr Arg Ala Pro Thr Gln Leu Leu Gly Leu Leu Leu Leu Trp
1               5                   10                  15

Leu Pro Gly Ala Arg Cys Ala Val Val Leu Thr Gln Thr Pro Ala Ser
            20                  25                  30

Val Ser Ala Ala Val Gly Gly Thr Val Ser Ile Ser Cys Gln Ser Ser
        35                  40                  45

Lys Ser Val Tyr Asn Lys Asn His Leu Ala Trp Leu Gln Gln Lys Pro
50                  55                  60

Gly Gln Pro Pro Lys Leu Leu Ile Tyr Tyr Thr Ser Thr Pro Ala Ser
65                  70                  75                  80

Gly Val Pro Ser Arg Phe Arg Gly Ser Gly Ser Gly Thr Gln Leu Thr
                85                  90                  95

Leu Thr Ile Ser Asp Val Gln Cys Asp Asp Ala Ala Thr Tyr Tyr Cys
            100                 105                 110

Ala Gly Gly Tyr Asn Ser Asp Ser Asp Asn Thr Phe Gly Gly Gly Thr
            115                 120                 125

Glu Val Val Val Glu
    130

<210> SEQ ID NO 57
<211> LENGTH: 11
<212> TYPE: PRT
<213> ORGANISM: Oryctolagus cuniculus

<400> SEQUENCE: 57

Gly Phe Ser Phe Ser Ala Asn Tyr Tyr Met Cys
1               5                   10

<210> SEQ ID NO 58
<211> LENGTH: 11
<212> TYPE: PRT
<213> ORGANISM: Oryctolagus cuniculus

<400> SEQUENCE: 58

Gly Phe Ser Phe Ser Asp Ser Phe Trp Ile Ala
1               5                   10

<210> SEQ ID NO 59
<211> LENGTH: 11
<212> TYPE: PRT
<213> ORGANISM: Oryctolagus cuniculus

<400> SEQUENCE: 59

Gly Phe Asp Leu Ser Ser Thr Tyr Tyr Met Cys
1               5                   10

<210> SEQ ID NO 60
<211> LENGTH: 11
<212> TYPE: PRT
<213> ORGANISM: Oryctolagus cuniculus

<400> SEQUENCE: 60

Gly Phe Ser Phe Ser Ser Ser Tyr Ser Met Cys
1               5                   10

<210> SEQ ID NO 61
<211> LENGTH: 11
<212> TYPE: PRT
<213> ORGANISM: Oryctolagus cuniculus

<400> SEQUENCE: 61

Gly Phe Ser Phe Gly Ser Gly Tyr Tyr Met Cys
1               5                   10

<210> SEQ ID NO 62
<211> LENGTH: 10
<212> TYPE: PRT
<213> ORGANISM: Oryctolagus cuniculus

<400> SEQUENCE: 62

Arg Phe Ser Phe Ser Ser Thr Tyr Met Cys
1               5                   10

<210> SEQ ID NO 63
<211> LENGTH: 11
<212> TYPE: PRT
<213> ORGANISM: Oryctolagus cuniculus

<400> SEQUENCE: 63

Gly Phe Ser Phe Ser Arg Gly Tyr Tyr Met Cys
1               5                   10

<210> SEQ ID NO 64
<211> LENGTH: 11
<212> TYPE: PRT
<213> ORGANISM: Oryctolagus cuniculus

<400> SEQUENCE: 64

Gly Phe Ser Phe Ser Asp Ser Phe Trp Ile Ala
1               5                   10

<210> SEQ ID NO 65
<211> LENGTH: 10
<212> TYPE: PRT
<213> ORGANISM: Oryctolagus cuniculus

<400> SEQUENCE: 65

Gly Phe Ser Leu Asn Tyr Tyr Trp Pro Cys
1               5                   10

<210> SEQ ID NO 66
<211> LENGTH: 11
<212> TYPE: PRT
<213> ORGANISM: Oryctolagus cuniculus

<400> SEQUENCE: 66

Gly Ile Asp Phe Ser Ser Tyr Tyr Tyr Met Cys
1               5                   10

<210> SEQ ID NO 67
<211> LENGTH: 11
<212> TYPE: PRT
<213> ORGANISM: Oryctolagus cuniculus

<400> SEQUENCE: 67

Gly Phe Ser Phe Gly Ser Gly Tyr Tyr Met Cys
1               5                   10

<210> SEQ ID NO 68
<211> LENGTH: 11
<212> TYPE: PRT
<213> ORGANISM: Oryctolagus cuniculus

<400> SEQUENCE: 68

Gly Phe Ser Phe Ser Arg Gly Tyr Tyr Ile Cys
1               5                   10

<210> SEQ ID NO 69
<211> LENGTH: 11
<212> TYPE: PRT
<213> ORGANISM: Oryctolagus cuniculus

<400> SEQUENCE: 69

Gly Phe Ser Leu Ser Ser Ser Tyr Phe Met Cys
1               5                   10

<210> SEQ ID NO 70
<211> LENGTH: 11
<212> TYPE: PRT
<213> ORGANISM: Oryctolagus cuniculus

<400> SEQUENCE: 70

Gly Phe Ser Phe Ser Asp Ser Phe Trp Ile Ala
1               5                   10

```
<210> SEQ ID NO 71
<211> LENGTH: 11
<212> TYPE: PRT
<213> ORGANISM: Oryctolagus cuniculus

<400> SEQUENCE: 71

Gly Phe Ser Phe Ser Ser Ser Tyr Trp Ile Cys
1               5                   10

<210> SEQ ID NO 72
<211> LENGTH: 11
<212> TYPE: PRT
<213> ORGANISM: Oryctolagus cuniculus

<400> SEQUENCE: 72

Gly Phe Ser Phe Ser Gly Thr Tyr Trp Ile Cys
1               5                   10

<210> SEQ ID NO 73
<211> LENGTH: 11
<212> TYPE: PRT
<213> ORGANISM: Oryctolagus cuniculus

<400> SEQUENCE: 73

Gly Phe Ser Phe Ser Ser Thr Tyr Trp Ile Cys
1               5                   10

<210> SEQ ID NO 74
<211> LENGTH: 10
<212> TYPE: PRT
<213> ORGANISM: Oryctolagus cuniculus

<400> SEQUENCE: 74

Gly Phe Asp Leu Ser Ser Asn Ala Met Asn
1               5                   10

<210> SEQ ID NO 75
<211> LENGTH: 10
<212> TYPE: PRT
<213> ORGANISM: Oryctolagus cuniculus

<400> SEQUENCE: 75

Gly Phe Ser Leu Ser Ser Tyr Ala Val Asn
1               5                   10

<210> SEQ ID NO 76
<211> LENGTH: 10
<212> TYPE: PRT
<213> ORGANISM: Oryctolagus cuniculus

<400> SEQUENCE: 76

Gly Phe Ser Leu Ser Thr Tyr Asp Met Thr
1               5                   10

<210> SEQ ID NO 77
<211> LENGTH: 10
<212> TYPE: PRT
<213> ORGANISM: Oryctolagus cuniculus

<400> SEQUENCE: 77

Gly Phe Ser Leu Ser Ser Tyr Asp Met Asn
1               5                   10

<210> SEQ ID NO 78
<211> LENGTH: 10
```

```
<212> TYPE: PRT
<213> ORGANISM: Oryctolagus cuniculus

<400> SEQUENCE: 78

Gly Phe Ser Leu Ser Ser Tyr Ala Val Asp
1               5                   10

<210> SEQ ID NO 79
<211> LENGTH: 10
<212> TYPE: PRT
<213> ORGANISM: Oryctolagus cuniculus

<400> SEQUENCE: 79

Gly Phe Ser Leu Ser Asp Tyr Val Met Arg
1               5                   10

<210> SEQ ID NO 80
<211> LENGTH: 17
<212> TYPE: PRT
<213> ORGANISM: Oryctolagus cuniculus

<400> SEQUENCE: 80

Cys Ile Tyr Ala Ser Ser Gly Ser Thr Trp Tyr Ala Ser Trp Ala Lys
1               5                   10                  15

Gly

<210> SEQ ID NO 81
<211> LENGTH: 18
<212> TYPE: PRT
<213> ORGANISM: Oryctolagus cuniculus

<400> SEQUENCE: 81

Cys Ile His Ala Leu Ser Ser Gly Ser Thr Tyr Tyr Ala Asn Trp Ala
1               5                   10                  15

Arg Gly

<210> SEQ ID NO 82
<211> LENGTH: 16
<212> TYPE: PRT
<213> ORGANISM: Oryctolagus cuniculus

<400> SEQUENCE: 82

Cys Ile Tyr Ala Thr Gly Gly Thr Tyr Tyr Ala Ser Trp Ala Lys Gly
1               5                   10                  15

<210> SEQ ID NO 83
<211> LENGTH: 17
<212> TYPE: PRT
<213> ORGANISM: Oryctolagus cuniculus

<400> SEQUENCE: 83

Cys Ile Asp Thr Gly Arg Gly Tyr Thr Tyr His Ala Ser Gly Ala Lys
1               5                   10                  15

Gly

<210> SEQ ID NO 84
<211> LENGTH: 17
<212> TYPE: PRT
<213> ORGANISM: Oryctolagus cuniculus

<400> SEQUENCE: 84

Cys Ile Tyr Val Gly His Asp Ser Leu Tyr Tyr Ala Gly Trp Ala Arg
1               5                   10                  15
```

Gly

<210> SEQ ID NO 85
<211> LENGTH: 18
<212> TYPE: PRT
<213> ORGANISM: Oryctolagus cuniculus

<400> SEQUENCE: 85

Cys Thr Tyr Thr Gly Ser Ser Gly Gly Thr Tyr Tyr Ala Ser Trp Ala
1               5                   10                  15

Lys Gly

<210> SEQ ID NO 86
<211> LENGTH: 17
<212> TYPE: PRT
<213> ORGANISM: Oryctolagus cuniculus

<400> SEQUENCE: 86

Cys Ile Gly Ala Gly Ser Gly Asn Thr Tyr Tyr Ala Thr Trp Thr Lys
1               5                   10                  15

Gly

<210> SEQ ID NO 87
<211> LENGTH: 18
<212> TYPE: PRT
<213> ORGANISM: Oryctolagus cuniculus

<400> SEQUENCE: 87

Cys Ile His Ala Leu Ser Ser Gly Ser Thr Tyr Tyr Ala Asn Trp Ala
1               5                   10                  15

Arg Gly

<210> SEQ ID NO 88
<211> LENGTH: 18
<212> TYPE: PRT
<213> ORGANISM: Oryctolagus cuniculus

<400> SEQUENCE: 88

Cys Leu Asn Gly Gly Asp Ser Asp Thr Thr Val Tyr Ala Arg Trp Ala
1               5                   10                  15

Lys Gly

<210> SEQ ID NO 89
<211> LENGTH: 17
<212> TYPE: PRT
<213> ORGANISM: Oryctolagus cuniculus

<400> SEQUENCE: 89

Cys Ile Tyr Ala Gly Ser Gly Ser Thr Tyr Tyr Ala Ser Trp Ala Lys
1               5                   10                  15

Gly

<210> SEQ ID NO 90
<211> LENGTH: 17
<212> TYPE: PRT
<213> ORGANISM: Oryctolagus cuniculus

<400> SEQUENCE: 90

Cys Ile Tyr Val Gly His Asp Ser Leu Tyr Tyr Ala Gly Trp Ala Arg
1               5                   10                  15

Gly

<210> SEQ ID NO 91
<211> LENGTH: 17
<212> TYPE: PRT
<213> ORGANISM: Oryctolagus cuniculus

<400> SEQUENCE: 91

Cys Ile Gly Ala Gly Ser Gly Gly Thr Tyr Phe Ala Ser Trp Ala Lys
1               5                   10                  15

Gly

<210> SEQ ID NO 92
<211> LENGTH: 18
<212> TYPE: PRT
<213> ORGANISM: Oryctolagus cuniculus

<400> SEQUENCE: 92

Cys Ile Ser Ala Gly Ser Ser Gly His Thr Tyr Tyr Ala Ser Trp Ala
1               5                   10                  15

Lys Gly

<210> SEQ ID NO 93
<211> LENGTH: 18
<212> TYPE: PRT
<213> ORGANISM: Oryctolagus cuniculus

<400> SEQUENCE: 93

Cys Ile His Ala Leu Ser Ser Gly Ser Thr Tyr Tyr Ala Asn Trp Ala
1               5                   10                  15

Arg Gly

<210> SEQ ID NO 94
<211> LENGTH: 18
<212> TYPE: PRT
<213> ORGANISM: Oryctolagus cuniculus

<400> SEQUENCE: 94

Cys Ile Asn Thr Gly Ser Ser Val Thr Thr Val Tyr Ala Arg Trp Ala
1               5                   10                  15

Lys Gly

<210> SEQ ID NO 95
<211> LENGTH: 18
<212> TYPE: PRT
<213> ORGANISM: Oryctolagus cuniculus

<400> SEQUENCE: 95

Cys Ile Tyr Ala Gly Ala Ser Gly Asn Ser Tyr Tyr Ala Asn Trp Ala
1               5                   10                  15

Gln Gly

<210> SEQ ID NO 96
<211> LENGTH: 18
<212> TYPE: PRT
<213> ORGANISM: Oryctolagus cuniculus

<400> SEQUENCE: 96

Cys Ile Asn Ser Asp Asp Ser Gly Thr Asn Val Tyr Ala Asn Trp Ala
1               5                   10                  15

Lys Gly

<210> SEQ ID NO 97
<211> LENGTH: 16
<212> TYPE: PRT
<213> ORGANISM: Oryctolagus cuniculus

<400> SEQUENCE: 97

Tyr Ile Thr Ile Ser Gly Ser Ala Gly Tyr Ala Ser Trp Ala Lys Gly
1               5                   10                  15

<210> SEQ ID NO 98
<211> LENGTH: 16
<212> TYPE: PRT
<213> ORGANISM: Oryctolagus cuniculus

<400> SEQUENCE: 98

Leu Ile Ala Thr Gly Gly Gly Thr Phe Tyr Thr Asn Trp Ala Arg Gly
1               5                   10                  15

<210> SEQ ID NO 99
<211> LENGTH: 16
<212> TYPE: PRT
<213> ORGANISM: Oryctolagus cuniculus

<400> SEQUENCE: 99

Leu Ile Asn Thr Ile Gly Ser Ala Tyr Tyr Ala Ser Trp Ala Ser Gly
1               5                   10                  15

<210> SEQ ID NO 100
<211> LENGTH: 16
<212> TYPE: PRT
<213> ORGANISM: Oryctolagus cuniculus

<400> SEQUENCE: 100

Val Ile Trp Asn Asn Gly Glu Ile Phe Tyr Ala Ser Trp Ala Lys Gly
1               5                   10                  15

<210> SEQ ID NO 101
<211> LENGTH: 16
<212> TYPE: PRT
<213> ORGANISM: Oryctolagus cuniculus

<400> SEQUENCE: 101

Ile Ile Ala Thr Gly Gly Gly Thr Tyr Tyr Thr Asn Trp Ala Lys Gly
1               5                   10                  15

<210> SEQ ID NO 102
<211> LENGTH: 16
<212> TYPE: PRT
<213> ORGANISM: Oryctolagus cuniculus

<400> SEQUENCE: 102

Val Ile Ser Ser Ala Gly Asn Thr Tyr Tyr Ala Thr Trp Ala Lys Asp
1               5                   10                  15

<210> SEQ ID NO 103
<211> LENGTH: 9
<212> TYPE: PRT
<213> ORGANISM: Oryctolagus cuniculus

<400> SEQUENCE: 103

Ser Gly Gly Tyr Ala Ala Tyr Asp Leu
1               5

```
<210> SEQ ID NO 104
<211> LENGTH: 16
<212> TYPE: PRT
<213> ORGANISM: Oryctolagus cuniculus

<400> SEQUENCE: 104

Ser Tyr Ala Gly Tyr Ala Asp Tyr Asn Val Ala Thr Gly Leu Asn Leu
1               5                   10                  15

<210> SEQ ID NO 105
<211> LENGTH: 12
<212> TYPE: PRT
<213> ORGANISM: Oryctolagus cuniculus

<400> SEQUENCE: 105

Asp Ile Val Gly Asp Asn Ile Tyr Tyr Phe Asn Phe
1               5                   10

<210> SEQ ID NO 106
<211> LENGTH: 15
<212> TYPE: PRT
<213> ORGANISM: Oryctolagus cuniculus

<400> SEQUENCE: 106

Ser Ser Tyr Val Arg Tyr Asp Asn Arg Asn Tyr Gly Phe Asn Leu
1               5                   10                  15

<210> SEQ ID NO 107
<211> LENGTH: 11
<212> TYPE: PRT
<213> ORGANISM: Oryctolagus cuniculus

<400> SEQUENCE: 107

Gly Ala Ser Ile Thr Asn Ser Tyr Phe Ser Leu
1               5                   10

<210> SEQ ID NO 108
<211> LENGTH: 11
<212> TYPE: PRT
<213> ORGANISM: Oryctolagus cuniculus

<400> SEQUENCE: 108

Pro Asp Val Gly Phe Asp Phe Ala Ile Asn Phe
1               5                   10

<210> SEQ ID NO 109
<211> LENGTH: 14
<212> TYPE: PRT
<213> ORGANISM: Oryctolagus cuniculus

<400> SEQUENCE: 109

Glu Asp Pro Gly Asn Asp Asp Tyr Gly Tyr Ala Asp Asn Leu
1               5                   10

<210> SEQ ID NO 110
<211> LENGTH: 16
<212> TYPE: PRT
<213> ORGANISM: Oryctolagus cuniculus

<400> SEQUENCE: 110

Ser Tyr Ala Gly Tyr Ala Asp Tyr Asn Val Ala Thr Gly Leu Asn Leu
1               5                   10                  15

<210> SEQ ID NO 111
<211> LENGTH: 10
```

```
<212> TYPE: PRT
<213> ORGANISM: Oryctolagus cuniculus

<400> SEQUENCE: 111

Tyr Ile Ile Pro Gly Tyr His Phe Asn Leu
1               5                   10

<210> SEQ ID NO 112
<211> LENGTH: 11
<212> TYPE: PRT
<213> ORGANISM: Oryctolagus cuniculus

<400> SEQUENCE: 112

Ser Gly Tyr Asn Asp Gly Ser Tyr Tyr Asn Leu
1               5                   10

<210> SEQ ID NO 113
<211> LENGTH: 11
<212> TYPE: PRT
<213> ORGANISM: Oryctolagus cuniculus

<400> SEQUENCE: 113

Gly Ala Ser Ile Thr Asn Ser Tyr Phe Ser Leu
1               5                   10

<210> SEQ ID NO 114
<211> LENGTH: 14
<212> TYPE: PRT
<213> ORGANISM: Oryctolagus cuniculus

<400> SEQUENCE: 114

Glu Asp Ala Gly Asn Asp Asp Tyr Gly Tyr Ala Arg Asn Leu
1               5                   10

<210> SEQ ID NO 115
<211> LENGTH: 10
<212> TYPE: PRT
<213> ORGANISM: Oryctolagus cuniculus

<400> SEQUENCE: 115

Ala Ser Ala Asp Val Gly Asp Tyr Ser Leu
1               5                   10

<210> SEQ ID NO 116
<211> LENGTH: 16
<212> TYPE: PRT
<213> ORGANISM: Oryctolagus cuniculus

<400> SEQUENCE: 116

Ser Tyr Ala Gly Tyr Ala Asp Tyr Asn Val Ala Thr Gly Leu Asn Leu
1               5                   10                  15

<210> SEQ ID NO 117
<211> LENGTH: 10
<212> TYPE: PRT
<213> ORGANISM: Oryctolagus cuniculus

<400> SEQUENCE: 117

Tyr Ile Ile Pro Gly Tyr Asn Phe Asn Leu
1               5                   10

<210> SEQ ID NO 118
<211> LENGTH: 16
<212> TYPE: PRT
<213> ORGANISM: Oryctolagus cuniculus
```

<400> SEQUENCE: 118

Ser Tyr Thr Gly Tyr Ala Asp Tyr Asn Val Ala Thr Gly Leu Asn Leu
1               5                   10                  15

<210> SEQ ID NO 119
<211> LENGTH: 10
<212> TYPE: PRT
<213> ORGANISM: Oryctolagus cuniculus

<400> SEQUENCE: 119

Tyr Pro Ile Pro Gly Tyr His Phe Asn Leu
1               5                   10

<210> SEQ ID NO 120
<211> LENGTH: 7
<212> TYPE: PRT
<213> ORGANISM: Oryctolagus cuniculus

<400> SEQUENCE: 120

Gly Tyr Asn Thr Met Ala Ile
1               5

<210> SEQ ID NO 121
<211> LENGTH: 10
<212> TYPE: PRT
<213> ORGANISM: Oryctolagus cuniculus

<400> SEQUENCE: 121

Gly Tyr Pro Gly Ser Ser Asp Phe Asn Ile
1               5                   10

<210> SEQ ID NO 122
<211> LENGTH: 11
<212> TYPE: PRT
<213> ORGANISM: Oryctolagus cuniculus

<400> SEQUENCE: 122

Gly Val Pro Gly Tyr Ser Ser Ser Phe Asn Ile
1               5                   10

<210> SEQ ID NO 123
<211> LENGTH: 12
<212> TYPE: PRT
<213> ORGANISM: Oryctolagus cuniculus

<400> SEQUENCE: 123

Asp Ala Asp Gly Gly Val Val Ser Tyr Phe His Val
1               5                   10

<210> SEQ ID NO 124
<211> LENGTH: 10
<212> TYPE: PRT
<213> ORGANISM: Oryctolagus cuniculus

<400> SEQUENCE: 124

Gly Tyr Pro Gly Ser Ser Asp Phe Asn Ile
1               5                   10

<210> SEQ ID NO 125
<211> LENGTH: 12
<212> TYPE: PRT
<213> ORGANISM: Oryctolagus cuniculus

<400> SEQUENCE: 125

Ile Trp Arg Pro Asp Asp Pro Thr Asn Ser Asp Ile
1               5                   10

<210> SEQ ID NO 126
<211> LENGTH: 13
<212> TYPE: PRT
<213> ORGANISM: Oryctolagus cuniculus

<400> SEQUENCE: 126

Gln Ser Ser Lys Ser Val Tyr Asn Asn Asn Trp Leu Ser
1               5                   10

<210> SEQ ID NO 127
<211> LENGTH: 11
<212> TYPE: PRT
<213> ORGANISM: Oryctolagus cuniculus

<400> SEQUENCE: 127

Gln Ala Ser Gln Ser Ile Gly Ser Tyr Leu Ala
1               5                   10

<210> SEQ ID NO 128
<211> LENGTH: 11
<212> TYPE: PRT
<213> ORGANISM: Oryctolagus cuniculus

<400> SEQUENCE: 128

Gln Ala Ser Gln Thr Ile Ser Asn Glu Leu Ser
1               5                   10

<210> SEQ ID NO 129
<211> LENGTH: 11
<212> TYPE: PRT
<213> ORGANISM: Oryctolagus cuniculus

<400> SEQUENCE: 129

Gln Ala Ser Glu Ser Ile Ser Ser Trp Leu Ser
1               5                   10

<210> SEQ ID NO 130
<211> LENGTH: 11
<212> TYPE: PRT
<213> ORGANISM: Oryctolagus cuniculus

<400> SEQUENCE: 130

Gln Ala Ser Glu Asp Ile Phe Ser Asn Leu Gly
1               5                   10

<210> SEQ ID NO 131
<211> LENGTH: 11
<212> TYPE: PRT
<213> ORGANISM: Oryctolagus cuniculus

<400> SEQUENCE: 131

Gln Ala Ser Gln Ser Ile Ser Ser Arg Leu Ala
1               5                   10

<210> SEQ ID NO 132
<211> LENGTH: 11
<212> TYPE: PRT
<213> ORGANISM: Oryctolagus cuniculus

<400> SEQUENCE: 132

Gln Ala Ser Glu Thr Ile Tyr Thr Leu Leu Ala

```
1               5                   10
```

<210> SEQ ID NO 133
<211> LENGTH: 11
<212> TYPE: PRT
<213> ORGANISM: Oryctolagus cuniculus

<400> SEQUENCE: 133

```
Gln Ala Ser Gln Ser Ile Gly Ser Tyr Leu Ala
1               5                   10
```

<210> SEQ ID NO 134
<211> LENGTH: 11
<212> TYPE: PRT
<213> ORGANISM: Oryctolagus cuniculus

<400> SEQUENCE: 134

```
Gln Ala Ser Gln Ser Ile Ser Ser Tyr Leu Tyr
1               5                   10
```

<210> SEQ ID NO 135
<211> LENGTH: 11
<212> TYPE: PRT
<213> ORGANISM: Oryctolagus cuniculus

<400> SEQUENCE: 135

```
Gln Ala Ser Gln Ser Ile Tyr Thr Trp Leu Ala
1               5                   10
```

<210> SEQ ID NO 136
<211> LENGTH: 11
<212> TYPE: PRT
<213> ORGANISM: Oryctolagus cuniculus

<400> SEQUENCE: 136

```
Gln Ala Ser Glu Asp Ile Phe Ser Asn Leu Gly
1               5                   10
```

<210> SEQ ID NO 137
<211> LENGTH: 11
<212> TYPE: PRT
<213> ORGANISM: Oryctolagus cuniculus

<400> SEQUENCE: 137

```
Gln Ala Ser Glu Ser Ala Tyr Thr Leu Leu Ala
1               5                   10
```

<210> SEQ ID NO 138
<211> LENGTH: 11
<212> TYPE: PRT
<213> ORGANISM: Oryctolagus cuniculus

<400> SEQUENCE: 138

```
Gln Ala Ser Gln Ser Ile Ser Thr Tyr Leu Ala
1               5                   10
```

<210> SEQ ID NO 139
<211> LENGTH: 11
<212> TYPE: PRT
<213> ORGANISM: Oryctolagus cuniculus

<400> SEQUENCE: 139

```
Gln Ala Ser Gln Ser Ile Gly Ser Tyr Leu Ala
1               5                   10
```

<210> SEQ ID NO 140
<211> LENGTH: 11
<212> TYPE: PRT
<213> ORGANISM: Oryctolagus cuniculus

<400> SEQUENCE: 140

Gln Ala Ser Gln Ser Ile Ser Ser Tyr Leu Tyr
1               5                   10

<210> SEQ ID NO 141
<211> LENGTH: 11
<212> TYPE: PRT
<213> ORGANISM: Oryctolagus cuniculus

<400> SEQUENCE: 141

Gln Ala Ser Gln Ser Ile Gly Ser Tyr Leu Ala
1               5                   10

<210> SEQ ID NO 142
<211> LENGTH: 11
<212> TYPE: PRT
<213> ORGANISM: Oryctolagus cuniculus

<400> SEQUENCE: 142

Gln Ala Ser Gln Asn Ile Tyr Gly Tyr Leu Phe
1               5                   10

<210> SEQ ID NO 143
<211> LENGTH: 13
<212> TYPE: PRT
<213> ORGANISM: Oryctolagus cuniculus

<400> SEQUENCE: 143

Gln Ser Ser Gln Asn Val Leu Ile Asn Asn Arg Leu Ala
1               5                   10

<210> SEQ ID NO 144
<211> LENGTH: 13
<212> TYPE: PRT
<213> ORGANISM: Oryctolagus cuniculus

<400> SEQUENCE: 144

Gln Ser Ser Lys Ser Val Tyr Asn Lys His His Leu Ala
1               5                   10

<210> SEQ ID NO 145
<211> LENGTH: 13
<212> TYPE: PRT
<213> ORGANISM: Oryctolagus cuniculus

<400> SEQUENCE: 145

Gln Ala Ser Glu Ser Val Asp Ser Asn Lys Arg Leu Ala
1               5                   10

<210> SEQ ID NO 146
<211> LENGTH: 11
<212> TYPE: PRT
<213> ORGANISM: Oryctolagus cuniculus

<400> SEQUENCE: 146

Gln Ala Ser Gln Thr Ile Tyr Thr Tyr Leu Ala
1               5                   10

<210> SEQ ID NO 147

```
<211> LENGTH: 13
<212> TYPE: PRT
<213> ORGANISM: Oryctolagus cuniculus

<400> SEQUENCE: 147

Gln Ser Ser Lys Ser Val Tyr Asn Lys Asn His Leu Ala
1               5                   10

<210> SEQ ID NO 148
<211> LENGTH: 11
<212> TYPE: PRT
<213> ORGANISM: Oryctolagus cuniculus

<400> SEQUENCE: 148

Gln Ala Ser Glu Ser Ile Ser Ser Ser Leu Ala
1               5                   10

<210> SEQ ID NO 149
<211> LENGTH: 7
<212> TYPE: PRT
<213> ORGANISM: Oryctolagus cuniculus

<400> SEQUENCE: 149

Arg Ala Ser Thr Leu Ala Ser
1               5

<210> SEQ ID NO 150
<211> LENGTH: 7
<212> TYPE: PRT
<213> ORGANISM: Oryctolagus cuniculus

<400> SEQUENCE: 150

Ala Ala Ser Asn Leu Ala Ser
1               5

<210> SEQ ID NO 151
<211> LENGTH: 7
<212> TYPE: PRT
<213> ORGANISM: Oryctolagus cuniculus

<400> SEQUENCE: 151

Leu Ala Ser Thr Leu Ala Ser
1               5

<210> SEQ ID NO 152
<211> LENGTH: 7
<212> TYPE: PRT
<213> ORGANISM: Oryctolagus cuniculus

<400> SEQUENCE: 152

Tyr Thr Ser Asn Leu Ala Ser
1               5

<210> SEQ ID NO 153
<211> LENGTH: 7
<212> TYPE: PRT
<213> ORGANISM: Oryctolagus cuniculus

<400> SEQUENCE: 153

Ala Ala Ser Asn Leu Glu Ser
1               5

<210> SEQ ID NO 154
<211> LENGTH: 7
<212> TYPE: PRT
```

```
<213> ORGANISM: Oryctolagus cuniculus

<400> SEQUENCE: 154

Arg Ala Ser Thr Leu Ala Ser
1               5

<210> SEQ ID NO 155
<211> LENGTH: 7
<212> TYPE: PRT
<213> ORGANISM: Oryctolagus cuniculus

<400> SEQUENCE: 155

Arg Ala Ser Thr Leu Glu Ser
1               5

<210> SEQ ID NO 156
<211> LENGTH: 7
<212> TYPE: PRT
<213> ORGANISM: Oryctolagus cuniculus

<400> SEQUENCE: 156

Ala Ala Ser Asn Leu Ala Ser
1               5

<210> SEQ ID NO 157
<211> LENGTH: 7
<212> TYPE: PRT
<213> ORGANISM: Oryctolagus cuniculus

<400> SEQUENCE: 157

Gln Ala Ser Lys Leu Ala Ser
1               5

<210> SEQ ID NO 158
<211> LENGTH: 7
<212> TYPE: PRT
<213> ORGANISM: Oryctolagus cuniculus

<400> SEQUENCE: 158

Lys Ala Ser Thr Leu Ala Ser
1               5

<210> SEQ ID NO 159
<211> LENGTH: 7
<212> TYPE: PRT
<213> ORGANISM: Oryctolagus cuniculus

<400> SEQUENCE: 159

Ala Ala Ser Asn Leu Glu Ser
1               5

<210> SEQ ID NO 160
<211> LENGTH: 7
<212> TYPE: PRT
<213> ORGANISM: Oryctolagus cuniculus

<400> SEQUENCE: 160

Gly Ala Ser Ile Leu Glu Ser
1               5

<210> SEQ ID NO 161
<211> LENGTH: 7
<212> TYPE: PRT
<213> ORGANISM: Oryctolagus cuniculus
```

```
<400> SEQUENCE: 161

Tyr Ala Ser Thr Leu Ala Ser
1               5

<210> SEQ ID NO 162
<211> LENGTH: 7
<212> TYPE: PRT
<213> ORGANISM: Oryctolagus cuniculus

<400> SEQUENCE: 162

Ala Ala Ser Asn Leu Ala Ser
1               5

<210> SEQ ID NO 163
<211> LENGTH: 7
<212> TYPE: PRT
<213> ORGANISM: Oryctolagus cuniculus

<400> SEQUENCE: 163

Asp Ala Ser Lys Leu Ala Ser
1               5

<210> SEQ ID NO 164
<211> LENGTH: 7
<212> TYPE: PRT
<213> ORGANISM: Oryctolagus cuniculus

<400> SEQUENCE: 164

Ala Ala Ser Asn Leu Ala Ser
1               5

<210> SEQ ID NO 165
<211> LENGTH: 7
<212> TYPE: PRT
<213> ORGANISM: Oryctolagus cuniculus

<400> SEQUENCE: 165

Glu Ala Ser Lys Leu Pro Ser
1               5

<210> SEQ ID NO 166
<211> LENGTH: 7
<212> TYPE: PRT
<213> ORGANISM: Oryctolagus cuniculus

<400> SEQUENCE: 166

Asp Ala Ser Lys Leu Ala Ser
1               5

<210> SEQ ID NO 167
<211> LENGTH: 7
<212> TYPE: PRT
<213> ORGANISM: Oryctolagus cuniculus

<400> SEQUENCE: 167

Tyr Ala Ser Thr Leu Ala Ser
1               5

<210> SEQ ID NO 168
<211> LENGTH: 7
<212> TYPE: PRT
<213> ORGANISM: Oryctolagus cuniculus

<400> SEQUENCE: 168
```

Thr Ala Ser Thr Leu Ala Ser
1               5

<210> SEQ ID NO 169
<211> LENGTH: 7
<212> TYPE: PRT
<213> ORGANISM: Oryctolagus cuniculus

<400> SEQUENCE: 169

Glu Ala Ser Lys Leu Ala Ser
1               5

<210> SEQ ID NO 170
<211> LENGTH: 7
<212> TYPE: PRT
<213> ORGANISM: Oryctolagus cuniculus

<400> SEQUENCE: 170

Tyr Thr Ser Thr Pro Ala Ser
1               5

<210> SEQ ID NO 171
<211> LENGTH: 7
<212> TYPE: PRT
<213> ORGANISM: Oryctolagus cuniculus

<400> SEQUENCE: 171

Tyr Ala Ser Asp Leu Ala Ser
1               5

<210> SEQ ID NO 172
<211> LENGTH: 12
<212> TYPE: PRT
<213> ORGANISM: Oryctolagus cuniculus

<400> SEQUENCE: 172

Ala Gly Tyr Glu Ser Val Asn Thr Asp Gly His Ala
1               5                   10

<210> SEQ ID NO 173
<211> LENGTH: 10
<212> TYPE: PRT
<213> ORGANISM: Oryctolagus cuniculus

<400> SEQUENCE: 173

Leu Gly Ser Phe Thr Gly Ser Asp Thr Thr
1               5                   10

<210> SEQ ID NO 174
<211> LENGTH: 12
<212> TYPE: PRT
<213> ORGANISM: Oryctolagus cuniculus

<400> SEQUENCE: 174

Gln Gln Gly Tyr Thr Tyr Ser Ser Val Asp Asn Val
1               5                   10

<210> SEQ ID NO 175
<211> LENGTH: 13
<212> TYPE: PRT
<213> ORGANISM: Oryctolagus cuniculus

<400> SEQUENCE: 175

Gln Ser Asn Tyr Gly Ser Ser Ser Thr Tyr Tyr Gly
1               5                   10

<210> SEQ ID NO 176
<211> LENGTH: 11
<212> TYPE: PRT
<213> ORGANISM: Oryctolagus cuniculus

<400> SEQUENCE: 176

Gln Ser Ala Tyr Tyr Ser Ser Ser Tyr Leu Ala
1               5                   10

<210> SEQ ID NO 177
<211> LENGTH: 10
<212> TYPE: PRT
<213> ORGANISM: Oryctolagus cuniculus

<400> SEQUENCE: 177

Gln Cys Thr Gly Tyr Thr Ile Ser Trp Pro
1               5                   10

<210> SEQ ID NO 178
<211> LENGTH: 14
<212> TYPE: PRT
<213> ORGANISM: Oryctolagus cuniculus

<400> SEQUENCE: 178

Gln Ser His Tyr Phe Asp Ser Ser Ser Gly Tyr Gly Asn Thr
1               5                   10

<210> SEQ ID NO 179
<211> LENGTH: 10
<212> TYPE: PRT
<213> ORGANISM: Oryctolagus cuniculus

<400> SEQUENCE: 179

Leu Gly Ser Phe Thr Gly Ser Asp Thr Thr
1               5                   10

<210> SEQ ID NO 180
<211> LENGTH: 12
<212> TYPE: PRT
<213> ORGANISM: Oryctolagus cuniculus

<400> SEQUENCE: 180

Gln Gln Gly Tyr Ser His Ile Asn Val Asp Asn Ile
1               5                   10

<210> SEQ ID NO 181
<211> LENGTH: 12
<212> TYPE: PRT
<213> ORGANISM: Oryctolagus cuniculus

<400> SEQUENCE: 181

Gln Arg Tyr Ser Trp Asn Gly Ser Tyr Gly Val Ser
1               5                   10

<210> SEQ ID NO 182
<211> LENGTH: 11
<212> TYPE: PRT
<213> ORGANISM: Oryctolagus cuniculus

<400> SEQUENCE: 182

Gln Ser Ala Tyr Tyr Ser Ser Ser Tyr Leu Ala
1               5                   10

```
<210> SEQ ID NO 183
<211> LENGTH: 14
<212> TYPE: PRT
<213> ORGANISM: Oryctolagus cuniculus

<400> SEQUENCE: 183

Gln Ser His Tyr Phe Gly Ser Ser Ser Gly Tyr Ala Asn Thr
1               5                   10

<210> SEQ ID NO 184
<211> LENGTH: 10
<212> TYPE: PRT
<213> ORGANISM: Oryctolagus cuniculus

<400> SEQUENCE: 184

Gln Ser Thr Tyr Tyr Gly Asn Gly His Pro
1               5                   10

<210> SEQ ID NO 185
<211> LENGTH: 10
<212> TYPE: PRT
<213> ORGANISM: Oryctolagus cuniculus

<400> SEQUENCE: 185

Leu Gly Ser Phe Thr Gly Ser Asp Thr Thr
1               5                   10

<210> SEQ ID NO 186
<211> LENGTH: 12
<212> TYPE: PRT
<213> ORGANISM: Oryctolagus cuniculus

<400> SEQUENCE: 186

Gln Gln Gly Tyr Ser His Ile Asn Val Asp Asn Ile
1               5                   10

<210> SEQ ID NO 187
<211> LENGTH: 10
<212> TYPE: PRT
<213> ORGANISM: Oryctolagus cuniculus

<400> SEQUENCE: 187

Leu Gly Ser Phe Thr Gly Ser Asp Thr Thr
1               5                   10

<210> SEQ ID NO 188
<211> LENGTH: 12
<212> TYPE: PRT
<213> ORGANISM: Oryctolagus cuniculus

<400> SEQUENCE: 188

Gln Gln Ser Tyr Ser His Ile Asn Val Asp Asn Ile
1               5                   10

<210> SEQ ID NO 189
<211> LENGTH: 11
<212> TYPE: PRT
<213> ORGANISM: Oryctolagus cuniculus

<400> SEQUENCE: 189

Gln Ala Gly Tyr Ser Ser Gly Asp Gly Asn Ala
1               5                   10

<210> SEQ ID NO 190
<211> LENGTH: 11
```

-continued

```
<212> TYPE: PRT
<213> ORGANISM: Oryctolagus cuniculus

<400> SEQUENCE: 190

Ala Gly Gly Tyr Pro Ser Asp Ser Asp Asn Thr
1               5                   10

<210> SEQ ID NO 191
<211> LENGTH: 12
<212> TYPE: PRT
<213> ORGANISM: Oryctolagus cuniculus

<400> SEQUENCE: 191

Ala Gly Tyr Lys Ala Thr Thr Thr Asp Ala Ser Ala
1               5                   10

<210> SEQ ID NO 192
<211> LENGTH: 12
<212> TYPE: PRT
<213> ORGANISM: Oryctolagus cuniculus

<400> SEQUENCE: 192

Gln Gln Gly Tyr Asn Ser Arg His Val Asp Asn Val
1               5                   10

<210> SEQ ID NO 193
<211> LENGTH: 11
<212> TYPE: PRT
<213> ORGANISM: Oryctolagus cuniculus

<400> SEQUENCE: 193

Ala Gly Gly Tyr Asn Ser Asp Ser Asp Asn Thr
1               5                   10

<210> SEQ ID NO 194
<211> LENGTH: 12
<212> TYPE: PRT
<213> ORGANISM: Oryctolagus cuniculus

<400> SEQUENCE: 194

Leu Gly Gly Tyr Ala Thr Ala Ala Tyr Arg Thr Ala
1               5                   10

<210> SEQ ID NO 195
<211> LENGTH: 322
<212> TYPE: PRT
<213> ORGANISM: Homo sapiens

<400> SEQUENCE: 195

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
```

```
            100                 105                 110
Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Glu His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys

<210> SEQ ID NO 196
<211> LENGTH: 16
<212> TYPE: PRT
<213> ORGANISM: Homo sapiens

<400> SEQUENCE: 196

Thr Ser Glu Ala Cys Glu Ser Cys Val Leu His Arg Ser Cys Ser Pro
1               5                   10                  15

<210> SEQ ID NO 197
<211> LENGTH: 20
<212> TYPE: PRT
<213> ORGANISM: Homo sapiens

<400> SEQUENCE: 197

Pro Cys Pro Val Gly Phe Phe Ser Asn Val Ser Ser Ala Phe Glu Lys
1               5                   10                  15

Cys His Pro Trp
            20

<210> SEQ ID NO 198
<211> LENGTH: 173
<212> TYPE: PRT
<213> ORGANISM: Homo sapiens

<400> SEQUENCE: 198

Glu Pro Pro Thr Ala Cys Arg Glu Lys Gln Tyr Leu Ile Asn Ser Gln
1               5                   10                  15
```

```
Cys Cys Ser Leu Cys Gln Pro Gly Gln Lys Leu Val Ser Asp Cys Thr
            20                  25                  30

Glu Phe Thr Glu Thr Gly Cys Leu Pro Cys Gly Glu Ser Glu Phe Leu
        35                  40                  45

Asp Thr Trp Asn Arg Glu Thr His Cys His Gln His Lys Tyr Cys Asp
 50                  55                  60

Pro Asn Leu Gly Leu Arg Val Gln Gln Lys Gly Thr Ser Glu Thr Asp
 65                  70                  75                  80

Thr Ile Cys Thr Cys Glu Glu Gly Trp His Cys Thr Ser Glu Ala Cys
                85                  90                  95

Glu Ser Cys Val Leu His Arg Ser Cys Ser Pro Gly Phe Gly Val Lys
            100                 105                 110

Gln Ile Ala Thr Gly Val Ser Asp Thr Ile Cys Glu Pro Cys Pro Val
            115                 120                 125

Gly Phe Phe Ser Asn Val Ser Ser Ala Phe Glu Lys Cys His Pro Trp
        130                 135                 140

Thr Ser Cys Glu Thr Lys Asp Leu Val Val Gln Gln Ala Gly Thr Asn
145                 150                 155                 160

Lys Thr Asp Val Val Cys Gly Pro Gln Asp Arg Leu Arg
                165                 170

<210> SEQ ID NO 199
<211> LENGTH: 19
<212> TYPE: PRT
<213> ORGANISM: Homo sapiens

<400> SEQUENCE: 199

Thr Cys Glu Glu Gly Trp His Cys Thr Ser Glu Ala Cys Glu Ser Cys
1               5                   10                  15

Val Leu His

<210> SEQ ID NO 200
<211> LENGTH: 19
<212> TYPE: PRT
<213> ORGANISM: Homo sapiens

<400> SEQUENCE: 200

Thr Cys Glu Glu Gly Trp His Ser Thr Ser Glu Ala Ser Glu Ser Cys
1               5                   10                  15

Val Leu His

<210> SEQ ID NO 201
<211> LENGTH: 4
<212> TYPE: PRT
<213> ORGANISM: Homo sapiens

<400> SEQUENCE: 201

Ile Cys Glu Pro
1

<210> SEQ ID NO 202
<211> LENGTH: 11
<212> TYPE: PRT
<213> ORGANISM: Homo sapiens

<400> SEQUENCE: 202

Thr Ser Glu Ala Cys Glu Ser Cys Val Leu His
1               5                   10
```

```
<210> SEQ ID NO 203
<211> LENGTH: 14
<212> TYPE: PRT
<213> ORGANISM: Artificial Sequence
<220> FEATURE:
<223> OTHER INFORMATION: Peptide spacer sequence

<400> SEQUENCE: 203

Glu Gly Lys Ser Ser Gly Ser Gly Ser Glu Ser Lys Val Asp
1               5                   10

<210> SEQ ID NO 204
<211> LENGTH: 18
<212> TYPE: PRT
<213> ORGANISM: Artificial Sequence
<220> FEATURE:
<223> OTHER INFORMATION: Peptide spacer sequence

<400> SEQUENCE: 204

Lys Glu Ser Gly Ser Val Ser Ser Glu Gln Leu Ala Gln Phe Arg Ser
1               5                   10                  15

Leu Asp

<210> SEQ ID NO 205
<211> LENGTH: 5
<212> TYPE: PRT
<213> ORGANISM: Artificial Sequence
<220> FEATURE:
<223> OTHER INFORMATION: Peptide spacer sequence

<400> SEQUENCE: 205

Gly Gly Gly Gly Ser
1               5
```